(12) United States Patent
Vidyasagar et al.

(10) Patent No.: US 10,940,137 B2
(45) Date of Patent: *Mar. 9, 2021

(54) MATERIALS AND METHODS FOR IMPROVING GASTROINTESTINAL FUNCTION

(71) Applicant: University of Florida Research Foundation, Incorporated, Gainesville, FL (US)

(72) Inventors: Sadasivan Vidyasagar, Gainesville, FL (US); Paul Okunieff, Gainesville, FL (US); Lurong Zhang, Gainesville, FL (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/441,062

(22) Filed: Jun. 14, 2019

(65) Prior Publication Data

US 2019/0307724 A1 Oct. 10, 2019

Related U.S. Application Data

(63) Continuation of application No. 14/656,255, filed on Mar. 12, 2015, now Pat. No. 10,322,109, which is a continuation of application No. 13/245,430, filed on Sep. 26, 2011, now Pat. No. 8,993,522.

(60) Provisional application No. 61/386,317, filed on Sep. 24, 2010, provisional application No. 61/431,629, filed on Jan. 11, 2011.

(51) Int. Cl.
| | |
|---|---|
| *A61K 31/405* | (2006.01) |
| *A61K 9/00* | (2006.01) |
| *A61K 31/7004* | (2006.01) |
| *A61K 31/7016* | (2006.01) |
| *A61K 47/18* | (2017.01) |
| *A61P 1/12* | (2006.01) |
| *A61K 47/20* | (2006.01) |
| *A61K 31/197* | (2006.01) |
| *A61K 31/198* | (2006.01) |

(52) U.S. Cl.
CPC .......... *A61K 31/405* (2013.01); *A61K 9/0095* (2013.01); *A61K 31/197* (2013.01); *A61K 31/198* (2013.01); *A61K 31/7004* (2013.01); *A61K 31/7016* (2013.01); *A61K 47/183* (2013.01); *A61K 47/20* (2013.01); *A61P 1/12* (2018.01)

(58) Field of Classification Search
None
See application file for complete search history.

(56) References Cited

U.S. PATENT DOCUMENTS

| | | | |
|---|---|---|---|
| 4,959,350 A | 9/1990 | Frokjaer et al. | |
| 5,254,572 A | 10/1993 | Serfontein | |
| 5,290,538 A | 3/1994 | Bertermann | |
| 5,514,656 A | 5/1996 | Cope et al. | |
| 5,522,378 A | 6/1996 | Ritson et al. | |
| 5,775,320 A | 7/1998 | Patton et al. | |
| 5,780,451 A | 7/1998 | DeMichele et al. | |
| 5,934,272 A | 8/1999 | Lloyd et al. | |
| 5,960,792 A | 10/1999 | Lloyd et al. | |
| 5,976,574 A | 11/1999 | Gordon | |
| 5,985,248 A | 11/1999 | Gordon et al. | |
| 5,998,363 A | 12/1999 | Forse et al. | |
| 6,001,336 A | 12/1999 | Gordon | |
| 6,136,346 A | 10/2000 | Eljamal et al. | |
| 6,673,355 B1 | 1/2004 | Estes et al. | |
| 6,956,023 B1 | 10/2005 | Calhoun et al. | |
| 8,168,669 B2 | 5/2012 | Matsumoto et al. | |
| 8,557,301 B2 | 10/2013 | Dolhun | |
| 8,993,522 B2* | 3/2015 | Vidyasagar | A61K 31/197 514/13.2 |
| 10,322,109 B2* | 6/2019 | Vidyasagar | A61K 31/198 |
| 2002/0042086 A1 | 4/2002 | Schwarz et al. | |
| 2003/0105104 A1* | 6/2003 | Burzynski | A61K 31/195 514/251 |
| 2003/0143293 A1 | 7/2003 | Shushunov | |
| 2003/0153622 A1 | 8/2003 | Hozumi et al. | |
| 2004/0213838 A1 | 10/2004 | Mazer et al. | |
| 2006/0247312 A1 | 11/2006 | Whippie et al. | |
| 2007/0009502 A1 | 1/2007 | Lall et al. | |
| 2007/0010459 A1 | 1/2007 | Liu et al. | |
| 2007/0202058 A1 | 8/2007 | Calton | |
| 2007/0244079 A1 | 10/2007 | Yoneda et al. | |
| 2007/0264401 A1 | 11/2007 | Taormina et al. | |
| 2007/0270355 A1 | 11/2007 | Garcia et al. | |
| 2008/0027007 A1 | 1/2008 | Benner et al. | |
| 2009/0203626 A1 | 8/2009 | Brand et al. | |
| 2009/0238893 A1 | 9/2009 | Langord et al. | |
| 2009/0318556 A1 | 12/2009 | Idle et al. | |
| 2010/0172876 A1 | 7/2010 | Langford | |
| 2010/0330197 A1 | 12/2010 | Higashiguchi et al. | |
| 2012/0077748 A1 | 3/2012 | Vidyasagar et al. | |
| 2012/0321729 A1 | 12/2012 | Subbiah | |

FOREIGN PATENT DOCUMENTS

| | | | |
|---|---|---|---|
| CA | 2809489 A1 | 3/2012 | |
| CN | 1850118 A | 10/2006 | |
| CN | 101779750 A | 7/2010 | |
| CN | 103153298 A | 6/2013 | |
| CN | 109152852 A | 1/2019 | |

(Continued)

OTHER PUBLICATIONS

Tyson nutraceuticals—Valine (http://www.tysonnutraceuticals.com/L-Valine.htm, 2009) (Year: 2009).*

(Continued)

*Primary Examiner* — Sergio Coffa
(74) *Attorney, Agent, or Firm* — Greenberg Traurig, LLP

(57) ABSTRACT

The subject invention provides therapeutic compositions, and uses thereof for the treatment or amelioration of injury to small intestine mucosa. In preferred embodiments, the composition comprises one or more nutrients and/or electrolytes that acquire or retain considerable absorptive capacity.

25 Claims, 27 Drawing Sheets

(56) References Cited

FOREIGN PATENT DOCUMENTS

| | | |
|---|---|---|
| EP | 0626176 A2 | 11/1994 |
| EP | 0689835 A2 | 1/1996 |
| EP | 0810829 B1 | 4/2000 |
| EP | 1818053 A | 8/2007 |
| JP | H06-340544 A | 12/1994 |
| JP | H07-30583 A | 1/1995 |
| JP | H07-330583 A | 12/1995 |
| JP | H08-73351 A | 3/1996 |
| JP | H08-175987 A | 7/1996 |
| JP | 2003-530411 A1 | 10/2003 |
| JP | 2004-123642 A | 4/2004 |
| JP | 2005518361 A | 6/2005 |
| JP | 2006-511504 A | 4/2006 |
| JP | 2006-304775 A | 11/2006 |
| JP | 2007-068466 A | 3/2007 |
| JP | 2007308387 A | 11/2007 |
| JP | 2011105640 A | 6/2011 |
| KR | 1019940025481 | 12/1994 |
| KR | 0136072 B1 | 4/1998 |
| KR | 100136072 B1 | 4/1998 |
| KR | 20020089448 | 11/2002 |
| KR | 1020060130583 A | 12/2006 |
| KR | 10-2007-0103506 | 10/2007 |
| KR | 20100135720 A | 12/2010 |
| MX | 2013003282 A | 5/2013 |
| WO | 87/01589 | 3/1987 |
| WO | 96/32149 A1 | 10/1996 |
| WO | 97/00088 A2 | 1/1997 |
| WO | 97/00088 A3 | 1/1997 |
| WO | 97/41833 A1 | 11/1997 |
| WO | 98/29096 A1 | 7/1998 |
| WO | 00/36915 | 6/2000 |
| WO | 01/78532 A1 | 10/2001 |
| WO | 03045372 A1 | 6/2003 |
| WO | 2004/043451 A1 | 5/2004 |
| WO | 2009/020394 A1 | 2/2009 |
| WO | 2011/064297 A1 | 6/2011 |
| WO | 2011/127056 A2 | 10/2011 |
| WO | 2012/020357 A1 | 2/2012 |
| WO | 2012/040707 A2 | 3/2012 |
| WO | 2013/119917 A1 | 8/2013 |
| WO | 2013/151744 A9 | 10/2013 |
| WO | 2014/164736 A1 | 10/2014 |
| WO | 2018/067717 A1 | 4/2018 |

OTHER PUBLICATIONS

Vitaminstuff.com—Serine (http://www.vitaminstuff.com/amino-acid-serine.html, 2007) (Year: 2007).*
Tyson nutraceuticals—Aspartic acid (http://www.tysonnutraceuticals.com/L-Aspartic%20acid.htm, 2009) (Year: 2009).*
Vitaminstuff.com—Lysine (http://www.vitaminstuff.com/amino-acid-lysine.html, 2008) (Year: 2008).*
Tyson nutraceuticals—Isoleucine (http://www.tysonnutraceuticals.com/L-Isoleucine.htm, 2008) (Year: 2008).*
Vitaminstuff.com—Threonine (http://www.vitaminstuff.com/amino-acid-threonine.html, 2008) (Year: 2008).*
Naylor, J.M., et al., "Effect of Glutamine or Glycine Containing Oral Electrolyte Solutions on Mucosal Morphology, Clinical and Biochemical Findings, in Calves with Viral Induced Diarrhea", Can J Vet Res 1997; 61: 43-48.
Cho, Chung-Hyun, et al., "Designed angiopoietin-1 variant, COMP-Ang1, protects against radiation-induced endothelial cell apoptosis", PNAS, Apr. 13, 2004, vol. 101, No. 15, pp. 5553-5558.
Epperly, M., et al., "Prevention of late effects of irradiation lung damage by manganese superoxide dismustase gene therapy", Gene Theraphy (1998) 5, pp. 196-208.
Wheeler, M.D., et al., "Dietary glycine blunts lung inflammatory cell influx following acute endotoxin", American Journal Physiol. Lung Cell Mol. Physiol, 279: L390-L398, 2000.
Notice of Opposition to a European Patent, European Pat. No. 2968241 (Application No. 14779732.8), filed Jul. 29, 2019, 20 pages.
Aminosyn®PF (available since Aug. 30, 2006, http://dailymed.nlm.nih.com/dailymed/lookup.cfm?setid=e649dc50-a3ce-4151-f698-788b6d5c83d0).
Hepatic-AID® II (available since Mar. 21, 2010, http://www.hormelhealthlabs.com/2colTemplate_product.aspx?page=CO_Hepatic-Aid).
Premasol (available since Feb. 1, 2001, http://dailymed.nlm.nih.com/dailymed/lookup.cfm?setid=9afdcc3e-0d06-47f4-86ca-40da48b2b02b).
Lapid, About.com, Celiac Disease, Jun. 10, 2009.
D'Souza, "Glutamine supplements in the critically ill", Journal of the Royal Society of Medicine, 97:425-427, 2004.
Elia, "Enteral Nutritional Support and Use of Diabetes-Specific Formulas for Patients with Diabetes", Diabetes Care 28:2267-2279, 2005.
Benight, "The role of methionine metabolism in inflammatory bowel disease," FASEB Journal 23:919.6, 2009.
Keefe, "Chemotherapy for cancer causes apoptosis that precedes hypoplasia in crypts of the small intestine in humans", Gut 47:632-637, 2000.
Maughan and Murray, "Sports Drinks: Basic Science and Practical Aspects," CRC Press, Chapter 4, 2001.
Wright, et al., "Regulation of Na+/Glucose cotransporters", The Journal of Experimental Biology 200 (1997), pp. 287-293.
Puntheeranurak, et al., "Substrate specificity of sugar transport by rabbit SGLT1: Single-molecule atomic force microscopy versus transport studies", Biochemistry 2007, 46, pp. 2797-2804 (Dec. 18, 2006).
Puthawala, et al., "Inhibitiion of integrin αvβ6, an activator of latent transforming growth factor-β, prevents radiation-induced lung fibrosis", American Journal of Respiratory and Critical Care Medicine, vol. 177, 2008, pp. 82-90.
Rezvani, M., "Treatment of radiation-induced normal tissue lesions", Iran. J. Radiat. Res., 2003; 1(2), pp. 63-78.
Rhoads, et al., "Can a super oral rehydration solution stimulate intestinal repair in acute viral enteritis?", Journal Diarrhoeal Dis. Res. 1996, Sep. 1996, 14(3), pp. 175-181.
Vidyasagar, et al., "Three distinct mechanisms of HCO3 secretion in rat distal colon", American Jounral Physiol Cell Physiol, vol. 287, Sep. 2004, pp. C612-C621.
Wright, et al., "Surprising versatility of Na+Glucose contrasporters: SLC5", Physiology, vol. 19, Dec. 2004, pp. 370-376, www.physiologyonline.org.
Wright, Kevin, "Important clinical aspects of amphibian physiology", Proceedings of the North American Veterinary Conference, vol. 20, Jan. 7-11, 2006, pp. 1685-1688.
Yin, et al., "Glucose enhances rotavirus enterotoxin-induced intestinal chloride secretion", Pflugers Archiv—European Journal of Physiology, ISSN 0031-6768 1987, published online May 10, 2017.
Zachos, et al., "NHERF3 (PDZK1) contributes to basal and calcium inhibition of NHE3 activity in caco-2BBe cells", The Jounral of biological chemistry, vol. 284, No. 35, pp. 23708-23718 (Aug. 28, 2009).
Zachos, et al., Regulation of intestinal electroneutral sodium absorption and the brush border Na+/H+ exchanger (NHE3) byintracellular calcium, Ann NY Acad. Sci. May 2009; 1165, pp. 240-248.
Zhang, et al., "Acute inflammation alters bicarbonate transport in mouse ileum", Journal of Physiology 581.3 (2007), pp. 1221-1233.
Williams et al., Treatment for radiation-induced pulmonary late effects: spoiled for choice or looking in wrong direction?, Curr Drug Targets, Nov. 1, 2010; 11(11), pp. 1386-1394.
WHO Drug Information, vol. 16, No. 2, 2002, pp. 113-203.
Rhoads, D., Molecular physiology of sodium-glucose contransporters, Physiological Reviews, vol. 74, No. 4, Oct. 1994, pp. 993-1026.
Moriya, et al., "Activation of sodium-glucose contransporter 1 ameliorates hyperglycemia by mediating incretin secretion in mice", American Journal of Encodrinal Metab. 297, Oct. 6, 2009, pp. E1358-E1365.
Cessarone, et al., "Accelerated antioxidant bioavailability of OPC-3 bioflavonoids administered as isotonix solution", NutraMetrix Advanced Nutraceuticals, "The world's most advanced nutraceuticals," Phytother Res. Jun. 2009, vol. 23 (6), pp. 775-777.

(56) References Cited

OTHER PUBLICATIONS

Prabhakaran, et al., "Selective amino acid mixture decreases chronic lung complications in irradiated mice", University of Florida, Gainesville, Florida, American Journal Respir. Crit. Care Med., 187, 2013, pp. A1880.
Nalin, et al., "Oral rehydration and maintenance of children with rotavirus and bacterial diarrhoeas", Bulletin of the World Health Organization, 57(3), 1979, pp. 453-459.
"Hepatic-Aid® II Instant Drink", Hepatic-Aid® II—Hormel Health Labs, Jan. 23, 2014, pp. 1-2; http://www.hormelhealthlabs.com/2colTemplate_product.aspx?page=CO_Hepatic-Aid.
"Is there a difference? Osmolarity vs. Osmolality . . . ", Infusion Nurse Blog, Sep. 29, 2017, pp. 1-3; https://infusionnurse.org/2010/05/14osmolarity-vs-osmolality/.
Halaihel, et al., "Direct inhibitory effect of rotavirus NSP4(114-135) peptide on the Na+-D-Glucose symporter of rabbit intestinal brush border membrane", Journal of Virology, Oct. 2000, vol. 74, No. 20, p. 9464-9470.
Torres-Pinedo, et al., "Studies on infant diarrhea. I. A comparison of the effects of milk feeding and intravenous therapy upon the composition and volume of the stool and urine", Journal of Clinical Investigation, vol. 45, No. 4, 1966, pp. 469-480.
Morris, et al. "The rotaviral enterotoxin NSP4 elevates intestinal cell calcium and causes diarrhea in cystic fibrosis mice", Intestinal Disorders, Apr. 1998, p. A401.
Kirmura, et al., "The contribution of peptides and amino acids to the taste of foodstuffs", Journal AGR. Food. Chem., vol. 17, No. 4, Jul.-Aug. 1960, 00. 689-695.
Knickelbein et al., "Membrane distribution of sodium-hydrogen and chloride-bicarbonate exchangers in crypt and villus cell membranes from rabbit ileum", The Journal of Clinical Investigation 1988, 82(6), pp. 2158-2163; https://doi.org/10.1172/JCI113838.
Kunzelmann, et al., "First encounter: How pathogens compromise epithelial transport", Physiology, vol. 19, Oct. 2001, pp. 240-244.
Lo, et al., "Cysteine scanning mutagenesis of the segment between putative transmembrane helices IV and V of the high affinity Na+-F/Glucose cotransporter SGLT1", The Journal of Biological Chemistry, vol. 273, No. 45, Issue of Nov. 6, pp. 29341-29351.
Lorrot, et al. "How do the rotavirus NSP4 and bacterial enterotoxins lead differently to diarrhea?", Virology Journal, Mar. 21, 2007, vol. 4:31, 6 pages.
Matthew, J., "Non-glucose oral rehydration solution—does it make a good ting better?", Indian Pediatrics, vol. 46, Jun. 17, 2009, pp. 501-505.
Haider, et al., "Management of acute diarrhea in diabetic patients using oral rehydration solutions containing glucose, rice, orglycine", BMJ vol. 308, Mar. 5, 1994, pp. 624-626.
Anonymous, "3% FreAmine® III (Amino Acid Injection) with Electrolytes", B. Braun, Medical Inc. 2009, https//dailymed.nlm.nih.gov/dailymed/archives/fdaDrugInfo.crm?archiveid=49352, 7 pages.
Ball, et al., "Age-dependent diarrhea induced by a rotaviral nonstructural glyoprotein", Science, 272.5258, Apr. 5, 1996, p. 101; http://go.galegroup.com.lp.hscl.ufl.edu/ps.retrieve.do?sgHitCountType=None&sort=DA-SORT&inPS=true&prodId=ITOF&userGroupName=gain40375 . . . , 5 pages.
Berkey, et al., "Managing the adverse effects of radiation therapy", American Family Physician, Aug. 15, 2010, vol. 82, No. 4, 2010, pp. 381-388, www.aafp.org/afp.
Blaylock, Is glutamine supplementation helpful or harmful?, Advanced Nutritional Concepts, LLC, 3 pages.
Castaneda, et al., "Thioglycosides as inhibitors of hSGLT1 and hSGLT2: Potential therapeutic agents for the control of hyperglycemia in diabetes", Int. J. Med. Sci., 2007, vol. 4, pp. 131-139.
Chapman, et al., "Glucose absorption and gastric emptying in critical illness", Critical Care, vol. 13, No. 4, Aug. 27, 2009; http://ccforum.com/content/13/4/R140, 8 pages.
Chen, et al., "Thermodynamic determination of the Na+: Glucose coupling ratio for the humanSGLT1 cotransporter", Biophysical Journal, vol. 69, Dec. 1995, pp. 2405-2414.
Dyer, et al., "Glucose sensing in the intestinal epithelium", Eur. J. Biochem., 270, 203, pp. 3377-3388.
Elliott, et al., "Glucagon-like peptide-1 (7-36) amide and glucose-dependent insuliotropic polypeptide secretion in response to nutrient ingestion in man: acute post-prandial and 24-h secretion patters", Journal of Endocrinology (1993), 138, pp. 159-166.
International Search Report and Written Opinion dated Apr. 10, 2012, issued by the Korean Intellectual Property Office in application No. PCT/US2011/053265 filed Sep. 26, 2011.
International Search Report and Written Opinion dated Jun. 2, 2013, issued by the Korean Intellectual Property Office in application No. PCT/US2013/025294 filed Feb. 8, 2013.
International Search Report and Written Opinion dated Feb. 13, 2018, issued by the United States Patent and Trademark Office in application No. PCT/US17/55167 filed Oct. 4, 2017.
International Search Report and Written Opinion dated Aug. 27, 2014, issued by the Korean Intellectual Property Office in application No. PCT/US2014/023363 filed Mar. 11, 2014.
International Search Report and Written Opinion dated Jun. 28, 2013, issued by the Korean Intellectual Property Office in application No. PCT/US2013/031970 filed Mar. 15, 2013.
Tyson nutraceticals—Aspartic acid (http://www.tysonnutraceuticals.com/L-Aspartic%20acid.htm, 2009).
Vitaminstuff.com—Lysine (http://www.vitaminstuff.com/amino-acid-lysine.html, 2008).
Tyson nutraceticals—Isoleucine (http://www.tysonnutraceuticals.com/L-Isoleucine.htm).
Vitaminstuff.com—Threonine (http://www.vitaminstuff.com/amino-acid-threonine.html, 2007).
Tyson nutraceticals—Valine (http://www.tysonnutraceuticals.com/L-Valine.htm, 2009).
Vitaminstuff.com—Serine (http://www.vitaminstuff.com/amino-acid-serine.html, 2007).
JP H07-330583 machine translation, Dec. 19, 1995.
First Examination Report dated Feb. 19, 2016, for corresponding Australian Patent Application No. 2015207919.
Mercola (downloaded on Oct. 19, 2015 from URL:<http://articles.mercola.com/sites/articles/archive/2004/05/01/glutamine.aspx>, May 1, 2004).
Sanz, et al., Methionine restriction decreases mitochondrial oxygen radical generation and leak as well as oxidative damage to mitochondrial DNA and proteins (FASEB J., Jun. 2006; 20(8): 1064-73).
Maughan, Nutrition in exercise and sport (Sports Drinks: Basic Science and Practical Aspects).
Guitierrez, Claudia et al., "Does an L-glutamine-containing, Glucose-free, Oral Rehydration Solution Reduce Stool Output and Time to Rehydrate in Children with Acute Diarrhoea? A Double-blind Randomized Clinical Trail," J. Health Pop JL Nutr., 2007, 25(3):278-284.
Teich, J., et al., "Intestinal glucose transport in acute viral enteritis in piglets," Clinical Science, 1981, 61:29-34.
Aminosyn®—PF (available since Aug. 30, 2006, http://dailymed.nim.nih.com/dailymed/lookup.cfm?setid=e649dc50-a3ce-4151-f698-88b6d5c83d0).
Benight, Nancy Marie et al., "The role of methionine metabolism in inflammatory bowel disease," The FASEB Journal, Apr. 2009, 23:9Meeting Abstract Supplement):919.6.
D'Souza, Raymond et al., "Glutamine supplements in the critically ill," Journal o the Royal Society of Medicine, 2004, 97:425-427.
Elia, Marinos et al., "Enteral Nutritional Support and Use of Diabetes-Specific Formulas for Patients with Diabetes," Diabetes Care, 2005, 28(9):2267-2279.
Leiper, John B. "Gastric Emptying and Intestinal Absorption of Fluids, Carbohydrates, and Electrolytes" from Sports Drinks: Basic Science and Practical Aspects, 2001, Chapter 4, pp. 90-128.
Detrick, Lawrence E., et al., "Influence of X-Ray Irradiation on Glucose Transport in the Rat Intestine", Radiation Research Society, www.jstor.org, Oct. 6, 1954, 7 pgs.
Nalin, D.R., et al., "Effect of glycine and glucose on sodium and water absorption in patients with cholera", Gut, 1970, 11, pp. 768-772.
Notice of opposition to EP Patent No. EP2968241 dated Jul. 29, 2019 (20 pages).

* cited by examiner

Changing in glucose-stimulated current (Δ) after different radiation doses in Swiss mice

MATERIALS AND METHODS FOR IMPROVING GASTROINTESTINAL FUNCTION

CROSS-REFERENCE TO RELATED APPLICATIONS

This application is a continuation application of U.S. application Ser. No. 14/656,255, filed Mar. 12, 2015, which is a continuation application of U.S. application Ser. No. 13/245,430, filed Sep. 26, 2011, which claims the priority benefit of U.S. Provisional Application Ser. No. 61/386,317, filed Sep. 24, 2010, and U.S. Provisional Application Ser. No. 61/431,629, filed Jan. 11, 2011, all of which are incorporated herein by reference in their entireties.

GOVERNMENT SUPPORT

This invention was made with government support under Grant No. RC2-AI-087580 awarded by the National Institutes of Health (NIH). The government has certain rights in this invention.

BACKGROUND OF INVENTION

Radiation, a common therapy for malignancies in the abdomen and pelvis, can cause severe damage to the lining of the gastrointestinal (GI) tract, which is composed of rapidly dividing intestinal epithelial cells. Toxic effects of radiation on the gastrointestinal system cause symptoms such as nausea, vomiting, diarrhea, electrolyte imbalance and dehydration, and adversely affect patient recovery in the course of cancer therapy. Even at low doses, a continuous loss of the villous and brush border of the small bowel is observed within days after irradiation. While crypt cells can rapidly repopulate the region following mild to moderate doses of (irradiation) IR, they became lost at a logarithmic rate after irradiation at high doses.

Irradiation is particularly destructive to the villous epithelium, where nutrient and electrolyte absorption occurs. The villous epithelium undergoes a continuous cellular loss and regeneration process, in which a constant supply of immature enterocytes, originating from progenitor cells located within the lower poles of the crypts of Lieberkuhn, migrate out of the proliferative compartment at the base of the crypt to the top of the villous. During their short lifespan, these enterocytes gradually mature along the crypt-villous axis into villous cells. Radiation therapy to the abdomen and pelvis region destroys not only the existing villous cells, but also enterocytes from which new villous cells form, and thus, can deplete almost the entire villous epithelium even at moderate doses.

Due to the increasing use of high total radiation doses and cytotoxic agents, radiotherapy has been complicated by its acute GI toxicity. Damage to the GI tract not only results in malabsorption and loss of nutrients and fluids, but also disrupts intestinal barrier function. The leaky gut allows for easy entry of pathogens across the mucosal barrier, causing inflammation, bacteremia and endotoxemia. For instance, acute radiation enteritis, diarrhea and abdominal pain can develop within days post irradiation even at doses as low as 5-12 Gy (a conventional fractionated course of radiation uses 1.8-2 Gy per fraction), although GI toxicity usually occurs at higher doses. Chronic radiation enteritis can develop between 18 months and 6 years after radiotherapy, while it may develop even 15 years later[27-29].

Treatment options for radiation enteritis are limited. Conventional treatment regimes include the administration of antidiarrheals to prevent fluid loss, smectite as an adsorbant of bile salts, opioids to relieve stomach or rectal pain, and steroids to relieve inflammation. Clinical trials have also investigated the efficacy of *L. acidophilus,* smectite or sucralfate for diarrhea prophylaxis, but only a moderate reduction of acute GI symptoms was achieved[30].

A common approach in the therapy of radiation enteritis is using total parenteral nutrition (TPN) to provide intestinal rest. However, whether parenteral nutrition satisfies the nutritional needs of patients, or actually has therapeutic effects on radiation enteritis remains to be determined. Although TPN may correct nutrition imbalance in certain patients, severe radiation enteritis may still develop[37]. TPN also causes intestinal atrophy, usually within 48 hours of administration. TPN also weakens mechanical and immunological barriers[38].

The exact biological mechanisms that lead to mucosal atrophy during TPN, which have not been well established, are believed to involve both local nutrient-sensing cell signals[39] and humoral signals, such as gut hormones[40,41]. TPN has been shown to induce a rapid (<8 h) decrease in intestinal blood flow, which precedes villous atrophy and the suppression of protein synthesis at 24 h, and cell proliferation and survival at 48 h[42]. In contrast, oral feeding rapidly increases intestinal blood flow in neonatal and mature animals[43,44]. Similarly, in neonatal piglets, enteral feeding almost immediately (within 1-3 hours) increases portal blood flow (PBF) up to 50% above values in food-deprived piglets[45]. Thus, as shown in various studies, enteral feeding is far superior to parenteral feeding[7,8].

Currently, there is a lack of nutritional therapy that can effectively alleviate radiation enteritis. Although early studies suggested that elemental or specific exclusion diets may be beneficial in selected cases[2,31,32], the efficacy of this approach has not been subsequently confirmed. The current dietary therapy merely offers a means of nutritional support to malnourished patients with chronic radiation enteritis.

Animal studies demonstrate that glutamine protects both upper and lower GI tract mucosa from injury caused by chemotherapy or radiation therapy (RT)[33-35]. However, clinical trials fail to show that oral glutamine feeding can prevent or alleviate acute diarrhea in patients who have received pelvic radiation therapy[36]. Thus, a need exists for the development of improved feeding compositions for treatment of irradiation-induced GI injury. As will be clear from the disclosures that follow, these and other benefits are provided by the subject invention.

BRIEF SUMMARY

The subject invention provides therapeutic compositions and methods for improving small intestine function. The subject composition is useful for the treatment or amelioration of gastrointestinal injury associated with the loss of small intestine epithelial cells, particularly in the villous region and the brush border, and/or for the treatment or amelioration of diseases or conditions associated with the alteration of absorptive capacity in the small intestine.

Advantageously, the subject therapeutic composition can be tailored to the misbalanced absorptive state of the gastrointestinal system caused by the loss of small intestine epithelial cells and the alteration of transport protein function in the small intestine. In a preferred embodiment, the subject composition is formulated for oral administration.

In one embodiment, the therapeutic composition comprises, consisting essentially of, or consisting of, one or more free amino acids selected from lysine, glycine, threonine, valine, tyrosine, aspartic acid, isoleucine, tryptophan, asparagine, and serine; and optionally, therapeutically acceptable carriers, electrolytes, vitamins, buffering agents, and flavoring agents. The therapeutic composition is administered via an enteral route. In one embodiment, the total osmolarity of the composition is from about 230 mosm to 280 mosm, or preferably, about 250 to 260 mosm. In one embodiment, the composition has a pH from about 7.1 to 7.9, preferably, about 7.4.

In a specific embodiment, the composition of the subject invention does not comprise glucose, glutamine, methionine, and/or lactose.

Also provided are methods for treatment or amelioration of diseases or symptoms associated with the loss of small intestine epithelial cells, particularly in the villous region and brush border, and diseases or symptoms associated with the alteration of transport protein function in the small intestine epithelium. The method comprises administering, via an enteral route, to a subject in need of such treatment, an effective amount of the composition of the subject invention. Preferably, the subject composition is administered orally and reaches the intestine of the subject.

The subject invention also provides methods for preparing the therapeutic composition, and for screening for nutrients or electrolytes for inclusion into the subject therapeutic/dietary composition, by selecting nutrients or electrolytes that retain or acquire considerable absorptive capacity following the destruction of small intestine epithelial cells. These methods can be adapted for use in individual patients, thereby facilitating the development of compositions and methods specifically designed to meet the needs of an individual patient.

BRIEF DESCRIPTION OF DRAWINGS

FIG. 3A shows change in $I_{sc}$ in mice epithelial cells over time following irradiation at 3 Gy. Values represent mean±S.E.M. n=6 tissues. Maximal increase in $I_{sc}$ was seen on 6th day following irradiation. No significant difference was seen between 5th, 6th and 7th days. With time>7 days post-irradiation, there was a slight decrease in $I_{sc}$ as compared to that of day 5, 6 or 7. $I_{sc}$ values of day 5, 6, and 7 were similar.

DETAILED DISCLOSURE

Figure 1A:
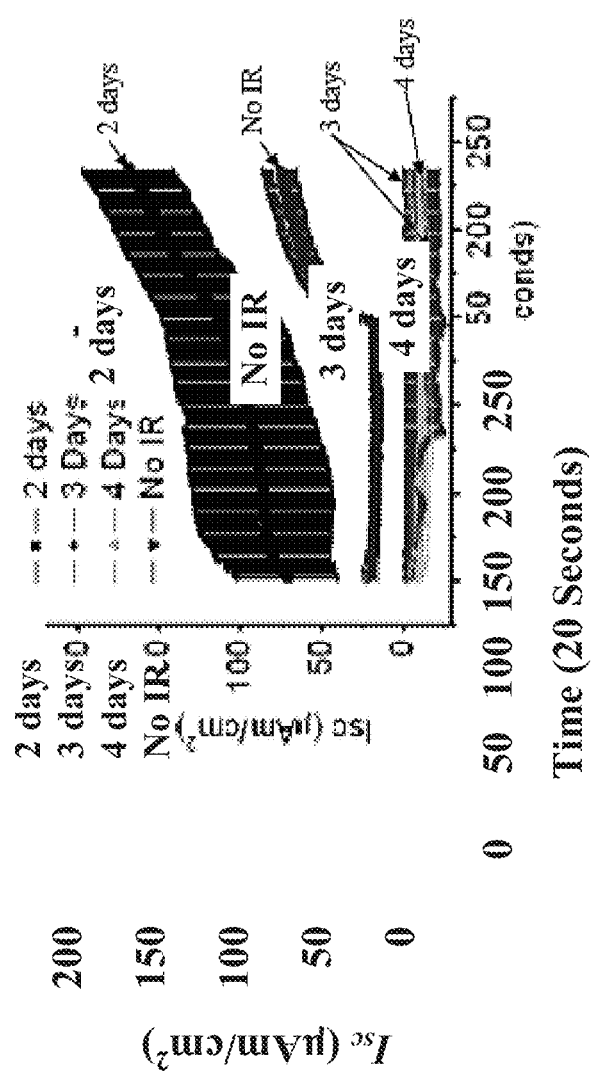
FIGS. 1A-1B show effect of irradiation (IR) on net anion secretion (1A) and conductance (1B). (1A). 12 Gy IR tissues were studied on day 1, 3 and 4. Maximal increase in $I_{sc}$ was seen on day 2. Arrow represents the time point when forskolin was added. (1B). Effect of increased doses of IR on net anion secretion. All the tissues were studied on day 6 and n=12. The results showed an IR dose-dependent increase in conductance.

The subject invention provides therapeutic compositions and methods for improving small intestine function. The composition is formulated for enteral administration. The compositions and methods of the subject invention are particularly useful for the treatment or amelioration of gastrointestinal injury associated with the loss of small intestine epithelial cells, particularly in the villous region and brush border, and/or for the treatment of diseases or conditions associated with the alteration of transport protein function in the small intestine epithelium.

Advantageously, the subject therapeutic composition is tailored to the misbalanced absorptive state of the gastrointestinal system caused by the loss of small intestine epithelial cells, particularly, in the small intestine villous region and brush border, as well as the alteration of transport protein function. Particularly, the subject invention can improve small intestine mucosal healing, restore small intestine function, enhance fluid retention, prevent or alleviate small intestine atrophy, and/or restore or enhance small intestine barrier function of a patient having injury to the small intestine mucosa.

In one embodiment, the therapeutic composition comprises, consists essentially of, or consists of one or more free amino acids selected from lysine, glycine, threonine, valine, tyrosine, aspartic acid, isoleucine, tryptophan, asparagine, and serine; and optionally, therapeutically acceptable carriers, electrolytes, vitamins, buffering agents, and flavoring agents. The therapeutic composition is administered via an enteral route. In one embodiment, the total osmolarity of the composition is from about 230 mosm to 280 mosm, or preferably, is about 250 to 260 mosm. In one embodiment, the composition has a pH from about 4.0 to 8.5, preferably 5.0 to 8.2, more preferably 6.0 to 8.0, more preferably, 7.1 to 7.9, and most preferably, about 7.4.

In a specific embodiment, the composition of the subject invention does not comprise glucose, glutamine, methionine, and/or lactose.

Also provided are methods for the treatment or amelioration of diseases or conditions associated with the loss of small intestine epithelial cells, particularly in the villous region and brush border, and diseases or conditions associated with the alteration of transport protein function in the small intestine epithelium. The method comprises administering via an enteral route, to a subject in need of such treatment, an effective amount of the composition of the subject invention.

The subject invention is based, at least in part, on the discovery that enteral feeding to subjects with only the nutrients that retain or acquire sufficient absorptive capacity following injury to the small intestine mucosa improves mucosal healing, restores small intestine function, enhances fluid retention, and alleviates an array of associated disease symptoms including, but not limited to, malabsorption, diarrhea, nausea, vomiting, electrolyte imbalance, and dehydration.

In accordance with the subject invention, it has been determined that, following radiation and chemotherapy, an alteration in transport protein function is observed with respect to, for example, glucose, glutamine, and lysine, and electrolytes such as $Na^+$, $HCO_3^-$, and $Cl^-$. In addition, radiation causes increased net anion secretion. The alterations of nutrient and electrolyte absorptive capacity occur immediately after radiation and chemotherapy, but it is possible for the absorptive capacity to recover towards normal (about 8-14 days post-irradiation in mice models).

Specifically, radiation causes an irradiation dose-dependent decrease in glucose absorption due to the reduced affinity of the sodium-dependent glucose transport system (SGLT-1) to glucose. Functional studies on glucose-stimulation showed that radiation caused a dose-dependent decrease in glucose-transport activity and decreased affinity of SGLT-1 for glucose.

It is known that the presence of unabsorbed nutrients or solutes in the intestinal lumen can lead to osmotic diarrhea. In accordance with the subject invention, oral feeding of an irradiated subject with glucose and/or glutamine has been found to cause osmotic diarrhea and reduced survival, while oral feeding of each, or a combination of, amino acids selected from lysine, glycine, threonine, valine, tyrosine, aspartic acid, isoleucine, tryptophan, asparagine, and/or serine, prolongs survival.

Therapeutic Composition for Improving Small Intestine Function

In one aspect, the subject invention provides therapeutic compositions for improving small intestine function. In one embodiment, the therapeutic composition comprises, consisting essentially of, or consisting of, one or more free amino acids selected from lysine, glycine, threonine, valine, tyrosine, aspartic acid, isoleucine, tryptophan, asparagine, and serine; and optionally, therapeutically acceptable carriers, electrolytes, vitamins, buffering agents, and flavoring agents. The therapeutic composition is administered via an enteral route.

Preferably, the composition is slightly alkaline and is hypotonic when compared to the osmotic pressure of small intestine epithelial cells (such as villous cells and crypt cells of the small intestine). Preferably, the subject composition comprises water. Preferably, the composition is formulated as an oral rehydration drink for improving small intestine function that is undermined due to the loss of, or injury to, villous epithelial cells.

In one embodiment, the total osmolarity of the composition is from about 230 mosm to 280 mosm, or any value therebetween. Preferably, the total osmolarity is from about 250 to 260 mosm. In another embodiment, the composition has a total osmolarity that is any value lower than 280 mosm.

In one embodiment, the composition has a pH from about 7.1 to 7.9, or any value therebetween. Preferably, the composition has a pH from about 7.3 to 7.5, more preferably, about 7.4.

In certain embodiments, each free amino acid can be present at a concentration from 4 mM to 40 mM, or any value therebetween, wherein the total osmolarity of the composition is from about 230 mosm to 280 mosm. Alternatively, if the amino acid concentration is calculated based on mg/l, each free amino acid can be present at a concentration from 300 mg/l to 8000 mg/L, or any value therebetween, wherein the total osmolarity of the composition is from about 240 mosm to 280 mosm.

In certain specific embodiments, the therapeutic composition comprises one or more free amino acids present at their respective concentrations as follows: lysine at a concentration of about 730 to 6575 mg/l, or any value therebetween; aspartic acid at a concentration of about 532 to 4792 mg/l, or any value therebetween; glycine at a concentration of about 300 to 2703 mg/l, or any value therebetween; isoleucine at a concentration of about 525 to 4722 mg/l, or any value therebetween; threonine at a concentration of about 476 to 4288 mg/l, or any value therebetween; tyrosine at a concentration of about 725 to 6523 mg/l, or any value therebetween; valine at a concentration of about 469 to 4217 mg/l, or any value therebetween; tryptophan at a concentration of about 817 to 7352 mg/l, or any value therebetween; asparagine at a concentration of about 528 to 4756 mg/l, or any value therebetween; and/or serine at a concentration of about 420 to 3784 mg/l, or any value therebetween; wherein the total osmolarity of the composition is from about 240 mosm to 280 mosm.

In one embodiment, the subject invention provides a drink comprising the following constituents lysine (11-21 mosm), aspartic acid (3-13 mosm), glycine (19-29 mosm), isoleucine (19-29 mosm), threonine (19-29 mosm), tyrosine (0.5-5 mosm), valine (19-29 mosm), tryptophan (5-20 mosm), asparagine (3-13 mosm), and serine (3-8 mosm), or a subset of these ingredients.

In one specific embodiment, the composition comprises lysine, glycine, threonine, valine, and tyrosine in a form of free amino acids. In a further specific embodiment, the composition comprises lysine, glycine, threonine, valine, tyrosine, aspartic acid, isoleucine, tryptophan, asparagine, and serine in a form of free amino acids.

In a further embodiment, the composition comprises one or more dipeptides that are made of the same or different amino acids selected from lysine, glycine, threonine, valine, tyrosine, aspartic acid, isoleucine, tryptophan, asparagine, or serine.

In one embodiment, the composition does not contain glutamine and/or methionine; and any di-, oligo-, or polypeptides or proteins that can be hydrolyzed into glutamine and/or methionine.

In an alternative embodiment, the composition may comprise free amino acid glutamine, and, optionally, one or more glutamine-containing dipeptides, wherein the total concentration of the free amino acid glutamine and the glutamine-containing dipeptide(s) is less than 300 mg/l, or any concentrations lower than 300 mg/l, such as 100 mg/l, 50 mg/l, 10 mg/l, 5 mg/l, 1 mg/l, 0.5 mg/l, or 0.01 mg/l.

In another alternative embodiment, the therapeutic composition may comprise free amino acid methionine, and, optionally, one or more methionine-containing dipeptides, wherein the total concentration of the free amino acid methionine and the methionine-containing dipeptide(s) is less than 300 mg/l, or any concentrations lower than 300 mg/l, such as 100 mg/l, 50 mg/l, 10 mg/l, 5 mg/l, 1 mg/l, 0.5 mg/l, or 0.01 mg/l.

In one embodiment, the therapeutic composition does not contain any saccharides, including any mono-, di-, oligo-, polysaccharides, and carbohydrates. In one specific embodiment, the therapeutic composition does not contain glucose, and/or any di-, oligo, polysaccharides, and carbohydrates that can be hydrolyzed into glucose. In a specific embodiment, the composition does not contain lactose. In another specific embodiment, the therapeutic composition does not contain fructose and/or galactose, and/or any di-, oligo, polysaccharides, and carbohydrates that can be hydrolyzed into fructose and/or galactose.

In an alternative embodiment, the therapeutic composition may comprise monosaccharide glucose, and, optionally, one or more glucose-containing disaccharides other than lactose, wherein the total concentration of the monosaccharide glucose and the glucose-containing disaccharide(s) is less than 3 g/l, or any concentrations lower than 3 g/l, such as 1 g/l, 500 mg/l, 300 mg/l, 100 mg/l, 50 mg/l, 10 mg/l, 5 mg/l, 1 mg/l, 0.5 mg/l, or 0.01 mg/l.

In certain embodiments, the therapeutic composition comprises one or more electrolytes selected from, for example, $Na^+$; $K^+$; $HCO_3^-$; $CO_3^{2-}$; $Ca^{2+}$; $Mg^{2+}$; $Fe^2$; $Cl^-$; phosphate ions, such as $H_2PO_4^-$, $HPO_4^{2-}$, and $PO_4^{3-}$; zinc; iodine; copper; iron; selenium; chromium; and molybdenum. In an alternative embodiment, the composition does not contain $HCO_3^-$ or $CO_3^{2-}$. In another alternative embodiment, the composition comprises $HCO_3^-$ and $CO_3^{2-}$ at a total concentration of less than 5 mg/l, or concentrations lower than 5 mg/l.

In a further embodiment, the therapeutic composition comprises one or more vitamins including, but not limited to, vitamin A, vitamin C, vitamin D (e.g., vitamin $D_1$, $D_2$, $D_3$, $D_4$, and/or $D_5$), vitamin E, vitamin $B_1$ (thiamine), vitamin $B_2$ (e.g., riboflavin), vitamin $B_3$ (e.g., niacin or niacinamide), vitamin $B_5$ (pantothenic acid), vitamin $B_6$ (pyridoxine), vitamin $B_7$ (biotin), vitamin $B_9$ (e.g., folate or folic acid), vitamin $B_{12}$ (cobalamin), and vitamin K (e.g., vitamin $K_1$, $K_2$, $K_3$, $K_4$, and $K_5$), and choline.

In certain embodiments, the composition does not contain one or more of the ingredients selected from oligo-, polysaccharides, and carbohydrates; oligo-, or polypeptides or proteins; lipids; small-, medium-, and/or long-chain fatty acids; and/or food containing one or more above-mentioned nutrients.

In one embodiment, phosphate ions, such as $H_2PO_4^-$, $HPO_4^{2-}$, and $PO_4^{3-}$, are used to buffer the composition of the subject invention. In one embodiment, the therapeutic composition uses $HCO_3^-$ or $CO_3^{2-}$ as a buffer. In another embodiment, the therapeutic composition does not use $HCO_3^-$ or $CO_3^{2-}$ as buffer.

The term "consisting essentially of," as used herein, limits the scope of the ingredients and steps to the specified materials or steps and those that do not materially affect the basic and novel characteristic(s) of the present invention, i.e., compositions and methods for treatment of injury to small intestine epithelium, particularly in the villous region and brush border. For instance, by using "consisting essentially of," the therapeutic composition does not contain any unspecified ingredients including, but not limited to, free amino acids, di-, oligo-, or polypeptides or proteins; and mono-, di-, oligo-, polysaccharides, and carbohydrates that have a direct beneficial or adverse therapeutic effect on treatment of injury to small intestine epithelium, particularly in the villous region and brush border. Also, by using the term "consisting essentially of," the compositing may comprise substances that do not have therapeutic effects on the treatment of injury to small intestine epithelium; such ingredients include carriers, excipients, adjuvants, flavoring agents, etc that do not affect the health or function of the injured small intestine epithelium, particularly in the villous region and brush border.

The term "oligopeptide," as used herein, refers to a peptide consisting of three to twenty amino acids. The term "oligosaccharides," as used herein, refers to a saccharide consisting of three to twenty monosaccharides.

In one embodiment, the composition of the subject invention comprises nutrients (such as free amino acids) and/or electrolytes that retain or acquire improved absorptive capacity in a subject having injury to small intestine epithelial cells, when compared to the absorptive capacity of normal controls who do not have injury to small intestine epithelial cells (such as villous cells, crypt cells, enterocytes, and intestinal projenitor cells).

In a further embodiment, the composition of the subject invention does not contain nutrients (such as amino acids) and/or electrolytes that are not absorbed, or have reduced absorption, in a subject having injury to small intestine epithelial cells, when compared to the absorptive capacity of normal controls who do not have injury to small intestine epithelial cells (such as villous cells, crypt cells, enterocytes, and intestinal projenitor cells). Advantageously, the compositions of the subject invention facilitate easy absorption of nutrients by the intestine to reduce undue energy expenditure, thereby providing intestinal rest in the immediate time period after mucosal injury.

Treatment Method for Improving Small Intestine Function

Another aspect of the subject invention provides methods for treatment or amelioration of diseases or conditions associated with the loss of, or injury to, small intestine epithelial cells, particularly in the villous region and brush border. In one embodiment, the loss of, or injury to, small intestine epithelial cells results in altered absorptive capacity for nutrients, electrolytes, and/or fluids. Advantageously, to patients with the loss of, or injury to, small intestine epithelial cells, particularly to patients with small intestine villous atrophy, the subject invention improves small intestine mucosal healing; improves small intestine function; enhances absorption of nutrients and fluid retention in the small intestine; prevents or alleviates small intestine atrophy; alleviates abdominal pain; prevents and/or treats diarrhea; restores or enhances small intestine barrier function; and/or reduces small intestine mucosal inflammation, bacteremia and/or endotoxemia.

Accordingly, the subject invention is particularly beneficial for improving gastrointestinal health of subjects that receive cytotoxic chemotherapeutic agents, pelvic or abdominal radiation, proton therapy, and abdominal surgery; subjects that suffer from infection or autoimmune diseases associated with acute or chronic inflammation in the small intestine; subjects that are routinely, or accidentally exposed to radiation, such as for example, astronauts and pilots who are routinely exposed to space radiation, and subjects exposed to radiation due to nuclear accident, acts of war, or terrorism.

In one embodiment, the method comprises administering, via an enteral route, to a patient or subject in need of such treatment, an effective amount of a composition of the invention. The composition can be administered to a patient or subject immediately before, during, and/or after injury to small intestine epithelial cells, and can be administered once or multiple times each day.

The term "subject" or "patient," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; domesticated animals such as dogs, cats; live stocks such as horses, cattle, pigs, sheep, goats, chickens; and animals such as mice, rats, guinea pigs, and hamsters.

In one specific embodiment, a subject in need of treatment is a patient with injury to small intestine mucosal epithelial cells, including the mucosa layer of duodenum, jejunum, and ileum. Particularly, a subject in need of treatment is a patient with injury to the villous region and brush border of the small intestine. For instance, the subject in need of treatment has villous atrophy (e.g., partial or complete wasting away of the villous region and brush border); has at least a 5% (such as at least 10%, 20%, 30%, or 50%) reduction in villous cells in the small intestine; has lost at least 5% (such as at least 10%, 20%, 30%, or 50%) villous height when compared to normal; has a loss of function of one or more transporters in the villous region and brush border of the small intestine, wherein the transporters include, but are not limited to, the SGLT-1 transporter, the AE2 transporter, the NHE1 transporter, and the NBCe1-A/B transporter, wherein the loss of transporter function is at least 5% (such as at least 10%, 20%, 30%, or 50%); and/or has a change in absorptive capacity of one or more nutrients in the small intestine, wherein the nutrients are selected from isoleucine, leucine, lysine, methionine, phenylalanine, threonine, tryptophan, valine, histidine, tyrosine, alanine, arginine, glutamine, aspartic acid, aspartate, cysteine, glycine, proline, serine, asparagine, glucose, fructose, and/or lactose, wherein the change in absorptive capacity is at least 5% (such as at least 10%, 20%, 30%, or 50%).

Changes in absorptive capacity of the small bowel can be determined by, for example, using an Ussing Chamber, as illustrated in the Materials and Methods section herein. For example, the changes in absorptive state can be determined by, for example, measuring a combination of indices including, for example, $K_m$, $V_{max}$, and $I_{sc}$. Injury to the villous and other regions of the small intestine can be determined by, for example, examination of biopsy samples of small intestine mucosa.

Diseases and therapeutic procedures that cause injury to small intestine mucosal epithelial cells, such as small intestine villous cells, can be readily determined by a skilled clinician. As is known in the medical profession, patients with certain diseases, such as inflammatory bowel disease (IBD), ulcerative colitis, duodenal ulcers, and Crohn's disease, suffer from chronic destruction of the small intestine mucosa. Radiation, chemo-, and proton therapy also cause injury to small intestine cells.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, or affecting the progression, severity, and/or scope of a disease or condition.

The term "amelioration" or any grammatical variation thereof (e.g., ameliorate, ameliorating, and amelioration etc.), as used herein, includes, but is not limited to, delaying the onset, or reducing the severity of a disease or condition (e.g., diarrhea, bacteremia and/or endotoxemia). Amelioration, as used herein, does not require the complete absence of symptoms.

The term "effective amount," as used herein, refers to an amount that is capable of treating or ameliorating a disease or condition or otherwise capable of producing an intended therapeutic effect.

In one specific embodiment, the subject invention provides a method for promoting intestinal health of a subject with injury to small intestine epithelial cells, wherein said method comprises: identifying a subject with injury to small intestine epithelial cells, or who is about to be inflicted with such an injury, and is in need of treatment or amelioration, and administering, via an enteral route, to the subject, an effective amount of a composition comprising, consisting essentially of, or consisting of one or more free amino acids selected from lysine, glycine, threonine, valine, tyrosine, aspartic acid, isoleucine, tryptophan, asparagine, and serine; water; and optionally, therapeutically acceptable carriers, electrolytes, vitamins, buffering agents, and flavoring agents, wherein the composition has a total osmolarity from 240 to 280 mosm and a pH of about 7.1 to 7.9.

In one embodiment, one or more of the following nutrients are not administered, via an enteral route, to a subject with (or about to have) injury to small intestine epithelial cells, wherein the nutrients are selected from glutamine, methionine, and any di-, oligo-, or polypeptides or proteins that can be hydrolyzed into glutamine and/or methionine; glucose and any di-, oligo, polysaccharides, and carbohydrates that can be hydrolyzed to glucose; and/or food that, upon digestion, requires absorption of any of the above-mentioned nutrients in the small intestine.

In a further embodiment, for a subject with (or about to have) injury to small intestine epithelial cells, none of the following nutrients are administered via an enteral route, wherein the nutrients are selected from saccharides, lipids, fatty acids, and/or food that, upon digestion, requires absorption of any of the above-mentioned nutrients in the small intestine. For patients that are exposed to radiation, or receive radiation, chemo-, and proton therapy, injury to small intestine epithelial cells typically lasts for at least 3, 7, 14, 21, 30 days, or any period between 1-30 days.

In a further embodiment, after any period between 1-30 days (such as after 3, 7, 14, 21, 30 days) since the subject is exposed to radiation, or receives radiation, chemo-, and/or proton therapy, one or more of the following nutrients are administered via an enteral route for enhancing mucosal healing, wherein the nutrients are selected from: glutamine, methionine, and any di-, oligo-, or polypeptides or proteins that can be hydrolyzed into glutamine and/or methionine; glucose and any di-, oligo, polysaccharides, and carbohydrates that can be hydrolyzed to glucose; and/or food that, upon digestion, requires absorption of any of the above-mentioned nutrients in the small intestine.

In a specific embodiment, the subject composition is administered orally and reaches the small intestine of the subject. Optionally, the method further comprises administering, via a parenteral route, required nutrients and electrolytes that are not administered in sufficient amounts via the enteral route.

In one embodiment, the subject invention is not used to provide significant amounts or all of the essential nutrition to a subject, but is to improve small intestine mucosal healing, restore small intestine function, enhance fluid retention, prevent or alleviate small intestine villous atrophy, prevent and/or treat diarrhea, and/or restore or enhance intestinal barrier function. In a specific embodiment, the composition of the drink is also based on improvement in the barrier function. Barrier function can be determined using multiple techniques including: a) an increase in conductance measurements on tissues mounted in a Ussing chamber, b) dilution potential used to measure relative permeability of Cl and Na (PCl/PNa) (only intact and functional barrier can maintain ion selectivity; when the barrier function is lost, the ion selective ratio is close to one), and c) measuring plasma endotoxin levels. When mucosal barrier function is lost the commensal gut bacteria can find their way into the systemic circulation, resulting is raised plasma endotoxin levels. Endotoxin levels can be measured in a patient's blood sample. Plasma endotoxin levels can also be used as an index to measure improvement with treatment.

The compositions of the subject invention can be used in the treatment or amelioration of any diseases or conditions associated with the loss, destruction, or reduction of small intestine epithelial cells, particularly the loss, destruction, or reduction in function or number of villous cells, enterocytes, and/or intestinal progenitor cells of the small intestine. The subject invention is particularly useful for the treatment or amelioration of any diseases or conditions associated with the loss, inactivation, or functional alteration of transport proteins in the small intestine epithelial cells, particularly transport proteins in the villous cells of the small intestine.

In one embodiment, the compositions and methods of the subject invention can be used in the treatment or amelioration of a disease or condition arising from, or associated with, a reduced affinity of sodium-dependent glucose transport system (SGLT-1) to glucose; a loss or reduced activity of $NH_2$-terminal electrogenic $Na+-HCO_3(-)$ cotransporter (NBCe1-A/B); a loss or reduced activity of apical $Cl^-$—$HCO_3^-$ exchange transporter (AE1); and/or an increased level or activity of CFTR and/or NKCC-1 transporter systems.

In a specifically preferred embodiment, the compositions and methods of the subject invention can be used in the treatment or amelioration of injury to the small intestine caused by radiation. In a specific embodiment, the subject invention can be used in the treatment or amelioration of injury to the small intestine caused by radiation therapy, particularly pelvic and abdominal radiation therapy. In a specific embodiment, the radiation therapy is for cancer treatment.

In addition, the subject invention can be used in the treatment or amelioration of injury to the small intestine caused by routine radiation exposure, such as exposure to space radiation in astronauts and pilots; radiation exposure, such as by a radioactive weapon and accidental nuclear release. Specifically, the subject invention can be used to treat or ameliorate acute and/or chronic radiation enteritis.

In certain specific embodiments, the compositions and methods of the subject invention can be used in the treatment or amelioration of injury to the small intestine, wherein the patient received radiation at 1, 2, 3, 4, 5, 6, 7, 8, 9, 10, 11, 12, 13, 14, 15, 16, 17, 18, 19, or 20 Gy. In another embodiment, the subject received radiation at a dose higher than 20 Gy.

Additionally, the subject invention can be used in the treatment or amelioration of injury to the small intestine caused by chemotherapeutic agents including, but not limited to, cisplatin, 5-fluorouracil (5-FU), hydroxyurea, etoposide, arabinoside, 6-mercaptopurine, 6-thioguanine, fludarabine, methothexate, steroids, and/or a combination thereof.

In addition, the subject invention can be used in the treatment or amelioration of injury to the small intestine caused by proton therapy.

In certain embodiments, the subject invention can be used in the treatment or amelioration of diseases involving injury to the small intestine including, but not limited to, inflammatory bowel disease (IBD), ulcerative colitis, duodenal ulcers, Crohn's disease, and/or coeliac disease (also known as celiac disease). The subject invention can be used in the treatment or amelioration of injury to the small intestine due to pathogenic infection, such as viral, bacterial, fungal or other microbial infection.

In one specific embodiment, the subject invention can be used in the treatment or amelioration of small intestine villous atrophy, i.e., partial or complete wasting away of the villous region and brush border, as well as diseases and conditions that arise from, associated with, and/or are caused by small intestinal villous atrophy.

In certain embodiments, the subject invention can be used in the treatment or amelioration of focal villous atrophy and/or diffuse villous atrophy; hyperplastic villous atrophy and/or hypoplastic villous atrophy; and/or villous atrophy with and without mucosal inflammation.

In certain embodiments, the subject invention can be used in the treatment or amelioration of hyperplastic villous atrophy (with crypt hyperplasia) and associated diseases and conditions including, but not limited to, coeliac disease (with gluten-sensitive enteropathy); chronic trauma; small bowel transplantion; urinary ileal conduits; intestinal mucosal inflammation; intestinal ulcers; intestinal anastomosis; glucagonoma; extensive small bowel resections; primary ileal villous atrophy; microscopic colitis atrophy; intestinal microvillous atrophy; and mitochondrial cytopathy (mitochondrial respiratory chain anomaly).

In certain embodiments, the subject invention can be used in the treatment or amelioration of hypoplastic villous atrophy (without crypt hyperplasia) and associated diseases and conditions including, but not limited to, malignancy; paneth cell deficiency; hypopituitarism; coeliac disease unresponsive to gluten-free diet; tropical sprue; radiation-associated ischemia; drug-induced villous atrophy, such as villous atrophy induced by neomycin and azathioprin.

In certain embodiments, the subject invention can be used in the treatment or amelioration of villous atrophy with mucosal inflammation as well as associated diseases and conditions including, but not limited to, coeliac disease; severe alimentary intolerance; congenital Crohn disease; autoimmune enteropathy; enterocolitis; and immunodeficiency syndromes.

In certain embodiments, the subject invention can be used in the treatment or amelioration of villous atrophy that are caused by diseases including, but not limited to, hepatitis; intestinal cancer; intestinal lymphoma; type 1 diabetes; allergy; eosinophillic gastroenteritis; viral gastroenteritis; and autoimmune enteropathy.

In certain embodiments, the subject invention can be used in the treatment or amelioration of villous atrophy associated with coeliac disease in the small bowel, including but not limited to, Marsh type 3a villous atrophy (>40 intraepithelial lymphocytes per 100 enterocytes; mild villous atrophy), Marsh type 3b villous atrophy (>40 intraepithelial lymphocytes per 100 enterocytes; marked villous atrophy), Marsh type 3c villous atrophy (>40 intraepithelial lymphocytes per 100 enterocytes; villous region absent o almost absent), (based on modified Marsh classification of coeliac disease and intestinal villous atrophy).

The subject invention can also be used to treat or ameliorate symptoms associated with injury to the small intestine including, but not limited to, malabsorption, diarrhea, nausea, vomiting, electrolyte imbalance, malabsorption, and dehydration.

Preparation of Therapeutic Composition for Improving Small Intestine Function

In another aspect, a method for preparing the therapeutic composition of the invention is provided. In one embodiment, the method comprises preparing a composition for promoting intestinal health of a subject with the loss of, or injury to, small intestine epithelial cells, wherein the composition comprises, consists essentially of, or consists of an effective amount of one or more ingredients, wherein the ingredients are absorbed by the small intestine of a subject with a loss of, or injury to, small intestine epithelial cells, wherein the composition has a total osmolarity from 230 mosm to 280 mosm, or any value therebetween (preferably about 250 mosm to 260 mosm), wherein the composition has a pH of about 7.1 to 7.9, or any value therebetween (preferably about 7.4), and wherein the composition is formulated for enteral administration.

In one embodiment, the ingredients are selected from free amino acids, dipeptides, monosaccharides, disaccharides, or a combination thereof, and, optionally, electrolytes, vitamins, flavoring agents, and/or carriers.

In one embodiment, the subject invention provides methods for screening for nutrients or electrolytes for inclusion into the subject therapeutic composition, by selecting nutrients or electrolytes that retain or acquire absorptive capacity following the destruction of small intestine epithelial cells in the villous and crypt regions.

The subject screening methods can be used for determining therapeutic nutrients and/or electrolytes that can be used in the treatment or amelioration of diseases or conditions associated with the loss, destruction, or reduction of small intestine epithelial cells, particularly the loss, destruction, or reduction of villous cells, enterocytes, and/or intestinal progenitor cells. In specific embodiments, the methods can be used to design compositions and methods to meet the needs of a specific patient or group of patients. In a specific embodiment, the subject composition is useful for the treatment or amelioration of injury to small intestine following radiation, chemo-, proton therapy, or due to acute or chronic inflammation in the small intestine.

In one embodiment, the subject screening method comprises:

a) contacting small intestine epithelial tissue having injury in the mucosa with a candidate nutrient or electrolyte;

b) determining a level of the ability of the small intestine epithelial tissue for absorbing said nutrient or electrolyte;

c) comparing said level to a predetermined level (such as in normal tissues); and d) selecting the candidate nutrient or electrolyte if the absorptive ability of the candidate nutrient or electrolyte is at least, for example, 50%, 60%, 70%, 80%, or 90% of the predetermined level.

In one embodiment, the subject screening method comprises:

a) administering, via an enteral route, a candidate nutrient or electrolyte to a subject with injury to the small intestine mocusa;

b) determining a level of intestinal absorptive capacity of said nutrient or electrolyte;

c) comparing said level to a predetermined level (such as in normal subjects); and d) selecting the candidate nutrient or electrolyte if the absorptive level of the candidate nutrient or electrolyte is at least, for example, 50%, 60%, 70%, 80%, or 90% of the predetermined level.

The level of absorptive capacity can be determined based on a combination of indices including, for example, $K_m$, $V_{max}$, and $I_{sc}$.

The predetermined reference value can be established by a person skilled in the art. For instance, the predetermined reference value can be established by measuring the levels of the absorptive capacity of said nutrient or electrolyte in normal small intestine epithelial tissues that do not have injury to the mucosa (such as villous cells, crypt cells, enterocytes, and intestinal progenitor cells). For another instance, the predetermined reference value can be established by measuring the levels of the intestinal absorptive capacity of said nutrient or electrolyte in a normal population who do not have injury to small intestine epithelial cells (such as villous cells, crypt cells, enterocytes, and intestinal projenitor cells).

In another embodiment, the subject screening method comprises:

a) determining function of small intestine tissue having injury in the mucosa;

b) contacting candidate nutrient or electrolyte with the small intestine tissue;

c) determining the function of the small intestine tissue after the small intestine tissue is contacted with the candidate nutrient or electrolyte; and d) selecting the candidate nutrient or electrolyte if said candidate nutrient or electrolyte improves small intestine function.

In another embodiment, the subject screening method comprises:

a) determining small intestine function of a subject with injury to small intestine mucosa;

b) administering, via an enteral route, a candidate nutrient or elecrtolyte to the subject;

c) determining the small intestine function of the subject after the candidate nutrient is administered; and d) selecting the candidate nutrient or electrolyte if said candidate nutrient or electrolyte improves small intestine function.

In certain embodiments, small intestine function is improved if the administration of the candidate nutrient or electrolyte decreases paracellular permeability, enhances small intestine barrier function. Also, small intestine function is improved if the enteral administration of the candidate nutrient or electrolyte prevents or treats diarrhea, and/or prolongs survival.

In certain embodiments, the nutrient and electrolyte that improves small intestine function of a subject with injury to small intestine mucosa can be selected using the methods as illustrated in the Examples, specifically, Examples 15-17.

Suitable candidate electrolytes include, for example, $Na^+$, $K^+$, $HCO_3^-$, $Cl^-$, $Mg^{2+}$, $Ca^{2+}$, $Fe^{2+}$ and/or $Zn^{2+}$.

Suitable candidate nutrients include essential and non-essential amino acids selected from, for example, isoleucine, leucine, lysine, methionine, phenylalanine, threonine, tryptophan, valine, histidine, tyrosine, selenocysteine, alanine, arginine, aspartate, cystein, glycine, proline, serine, asparagine, and pyrrolysine. Suitable candidate nutrients may also include fatty acids, saccharides (e.g., monosaccharides, disaccharides, and oligosaccharides), eletrolytes, and vitamins.

Candidate nutrients may also include non-natural amino acids, such as for example, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, and β-alanine.

In a further embodiment, the selection of nutrients and electrolytes also depends on, at least in part, the IR dosages received by the subject, radiation sources, the body part being irradiated, and/or the time that has elapsed after radiation; the type of chemotherapeutic agents, the dosage, and/or the time that has elapsed after chemotherapy; and the dosages of proton therapy received by the subject, and/or the time that has elapsed after proton therapy.

The subject screening assays can be performed utilizing a combination of techniques well known in the art, including but not limited to, Ussing chamber studies, cytology, immunohistochemistry, Western blots, enzyme-linked immunosorbent assay (ELISA), polymerase chain reaction (PCR), ion flux experiments, immunoprecipitation, immunofluorescence, radioimmunoassay, and immunocytochemistry.

Specifically, the ingredients can be chosen based on their ability to be absorbed by the small bowel mucosa of the patient, as determined by in-situ or isolated bowel preparations, using technologies such as Ussing Chambers to measure the absorptive capacity of the small intestine for such ingredient.

Formulations and Administration

The subject invention provides for therapeutic or pharmaceutical compositions comprising a therapeutically effective amount of the subject composition and, optionally, a pharmaceutically acceptable carrier. Such pharmaceutical carriers can be sterile liquids, such as water. The therapeutic composition can also comprise excipients, adjuvants, flavoring agents, etc that do not affect the health or function of the injured small intestine epithelium, particularly in the villous region and brush border. In an embodiment, the therapeutic composition and all ingredients contained therein are sterile.

The term "carrier" refers to a diluent, adjuvant, excipient, or vehicle with which the compound is administered. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the enteral mode of administration.

The invention also provides a pharmaceutical pack or kit comprising one or more containers filled with one or more of the ingredients, e.g., compound, carrier, or the pharmaceutical compositions of the invention.

In one embodiment, the pharmaceutical pack or kit further comprises instructions for administration, for example, with respect to effective therapeutic doses, and/or the timing of administration with reference to, for example, the elapse time from the exposure to radiation, chemotherapy, or proton therapy. In one embodiment, the therapeutic dose of the composition is determined based on the extent of injury to the small intestine mucosa. For instance, with regard to subjects that receive, or are about to receive radiation, the therapeutic dose of the composition is determined based on radiation sources, the body part being irradiated, and/or the time that has elapsed after radiation. With regard to subjects that receive, or are about to receive chemotherapy, the therapeutic dose of the composition is determined based on the type of chemotherapeutic agents, the dosage of chemotherapeutic agent, and/or the time that has elapsed after chemotherapy. With regard to subjects that receive, or are about to receive proton therapy, the therapeutic dose of the composition is determined based on the dosages of proton therapy received by the subject, and/or the time that has elapsed after proton therapy.

Materials and Methods

Experimental Animals

To study active $HCO_3^-$ secretion, 8-week-old, non-irradiated and irradiated, male BALB/c mice were obtained from the National Cancer Institute. Mice were randomly divided into groups, and abdomens were irradiated according to the gastrointestinal acute radiation syndrome (GI ARS) model with a Shepherd Mark-I, using a $^{137}Cs$ source delivering γ-irradiation at 1.84 Gy/min. Radiation was given as a single fraction. The GI ARS model will achieve maximum radiation damage to intestinal tissues, and mimics intestinal injury during radiation therapy of pelvic or abdominal tumors.

Changes in short circuit current ($I_{sc}$), both as a function of time following radiation and with increasing doses of radiation, were examined to determine the earliest time and the minimum radiation dose required to produce significant changes in $I_{sc}$. These studies were approved by the University of Rochester Animal Care and Use Committee.

Ion Flux Studies

Following exsanguinations, jejunal segment was obtained by excluding the distal 12 cm of small intestine adjacent to the caecum. This segment was washed and flushed in ice-cold Ringer's solution before the mucosa was stripped from the underlying muscular layers (Zhang, Ameen et al. 2007). The mucosa was mounted between the 2 halves of an Ussing-type Lucite chamber with an area of 0.30 $cm^2$ (P2304, Physiologic instruments, San Diego, Calif. 92128 USA), and electrical parameters were recorded using a voltage/current clamp device (VCC MC-8, Physiologic instruments, San Diego, Calif. 92128 USA) (Vidyasagar et al. 2005; Vidyasagar et al. 2004; Zhang et al. 2007; Vidyasagar and Ramakrishna 2002).

TABLE 1

Compositions of solutions

| Ionic composition | Regular ringer | $HCO_3^-$ free | $Na^+$ free solution | $Cl^-$-free solution | $HCO_3^-$ free (UB) | $HCO_3^-$-& $Cl^-$-free (UB) |
|---|---|---|---|---|---|---|
| $Na^+$ | 140 | 140 | — | 140 | 140 | 140 |
| $Cl^-$ | 119.8 | 119.8 | 119.8 | — | 119.8 | — |
| $K^+$ | 5.2 | 5.2 | 5.2 | 5.2 | 5.2 | 5.2 |
| $HCO_3^-$ | 25 | — | 25 | 25 | — | — |
| $HPO_4^-$ | 2.4 | 2.4 | 2.4 | 2.4 | — | — |
| $H_2PO_4^-$ | 0.4 | 0.4 | 0.4 | 0.4 | — | — |
| $Ca^{2+}$ | 1.2 | 1.2 | 1.2 | 1.2 | 1.2 | 1.2 |
| $Mg^{2+}$ | 1.2 | 1.2 | 1.2 | 1.2 | 1.2 | 1.2 |
| $SO_4^{2-}$ | — | — | — | 1.2 | 2.4 | 2.4 |
| Gluconate | — | — | — | — | — | — |
| Cyclamide | — | — | — | 1.2 | 0.4 | 5.2 |
| Isethionate | — | 25 | — | 115 | 25 | 140 |
| NMDG | — | — | 140 | — | — | — |
| HEPES | — | — | — | — | 0.1 | 0.1 |

Note:
Values are in mM. Ionic solutions were used for ion-substitution experiments. pH of all solutions were at 7.4. $H_2SO_4$ was used to adjust the pH to 7.4 in $Cl^-$-free solution, and in all others, HCl was used.
Abbreviations: UB, unbuffered solution
Intestinal preparations were bathed bilaterally in a regular Ringer's solution (Table 1), containing 8 mM of glutamine and gassed with a mixture of 95% oxygen ($O_2$) and 5% carbon dioxide ($CO_2$).

Measurement of $HCO_3^-$ Movement

A Bi-burette TIM 856 (Radiometer Analytical SAS, Villeurbanne, France) was used to measure $HCO_3^-$ secretion in stripped jejunal sheets (Vidyasagar et al. 2005; Vidyasagar et al. 2004; Zhang et al. 2007). Automated pumps maintained a constant pH for luminal solution through the addition of 0.01 μl of 0.025 M sulfuric acid ($H_2SO_4$). Standard-to-stat pH calibration was established by adding a known quantity of $H_2SO_4$ to a weak buffering solution, which contains an increasing concentration of $HCO_3^-$ to produce a linear titration curve.

Jejunal tissues were exposed to a buffered solution on the bath side (serosal side), while the luminal side was exposed to an $HCO_3^-$ free, low-buffered solution (0.1-mM HEPES (4-(2-hydroxyethyl)-1-piperazineethanesulfonic acid) buffer, pH 7.4). The $HCO_3^-$ secretion was equivalent to the amount of acid added to the luminal solution to maintain the pH at 7.4 (or the stat pH). All experiments were performed under voltage-clamp conditions. $HCO_3^-$-free solution was gassed with 100% $O_2$ and $HCO_3^-$-containing solution was gassed with 95% $O_2$ and 5% $CO_2$. The $HCO_3^-$ secretion was expressed as $\mu eq \cdot h^{-1} \cdot cm^{-2}$ (Vidyasagar et al. 2005; Vidyasagar et al. 2004; Zhang et al. 2007).

After the tissue was mounted, $HCO_3^-$ secretions were initially present in the absence of bath $HCO_3^-$, but rapidly fell towards 0 within 20-30 minutes. If bath $HCO_3^-$ was not present during the titration, the $HCO_3^-$ secretion remained close to 0. Presence of $HCO_3^-$ in the bath solution resulted in a rapid increase in $HCO_3^-$ secretions, which remained constant for at least 2 hours (Vidyasagar et al. 2005; Vidyasagar et al. 2004; Zhang et al. 2007). When inhibitors were added to the mucosal solution, the pH was adjusted and allowed to equilibrate for 30 minutes, until a steady rate of $HCO_3^-$ secretion was observed. When the inhibitor was added to the bath side, the tissue was also equilibrated for 30 minutes to achieve a steady rate of $HCO_3^-$ secretion (see Table 3).

All experiments were performed during the initial 1-hour steady-state period. 1 tissue from each animal was used for each experiment; only 1 experimental condition was studied with each tissue sample. All experiments were repeated for at least 4 times.

Immunohistochemistry

Frozen tissue slices from both non-irradiated and irradiated mice were immunofluorescence-stained using an anti-NBCe1-A/B antibody (Bevensee, Schmitt et al. 2000). NBCe1-A/B is a polyclonal antibody raised against the carboxy terminus, common to both sodium bicarbonate cotransporters (NBCe1-A and NBCe1-B). The immunostaining procedure was done on day 6 post-irradiation. Isolated tissues were washed in ice-cold regular Ringer's solution, embedded in frozen-section embedding medium, and placed in liquid nitrogen; 6-μm sections were made in cryostat.

Western Blot Studies

Jejunal lysates were prepared from mucosal scrapings of non-irradiated and irradiated mice. Tissues were analyzed for NKCC1(Santa Cruz Calif., USA), NBCe1-A/B (Mark Daniel Parker, Case Western Reserve University Medical School, Cleveland, Ohio), and cystic fibrosis transmembrane conductance regulator (CFTR) (Santa Cruz Calif., USA) protein expression by Western blots (Bevensee et al. 2000).

Mucosal scrapings were lysed in a triacylglycerol hydrolase buffer containing 25-mM HEPES; 10% glycerol; and 1% Triton X-100 (polyethylene glycol p-(1,1,3,3-tetramethylbutyl)-phenyl ether) containing a protease inhibitor mixture with (10-mM iodoacetamide, 1-mM phenylmethylsulphonyl fluoride, and 2-μg·$ml^{-1}$ leupeptin) at pH 7.4 (All chemicals were obtained from Sigma-Aldrich Co., USA unless otherwise stated). The protein concentration was determined using the Bradford assay. Equivalent loads of proteins from irradiated and non-irradiated samples were analyzed using sodium dodecyl sulfate-polyacrylamide gel electrophoresis (SDS-PAGE). NKCC1, NBCe1-A/B, and CFTR proteins were detected using affinity-purified polyclonal antibodies.

Statistics

Results are presented as mean±standard error of mean. Statistical analysis was performed in 2 steps: 1) overall difference was tested using analysis of variance (ANOVA) (or its non-parametric equivalent Kruskal-Wallis); and 2) Bonferroni-adjusted P-values were computed for all pairwise comparisons.

EXAMPLES

Following are examples which illustrate procedures for practicing the invention. These examples should not be construed as limiting. All percentages are by weight and all solvent mixture proportions are by volume unless otherwise noted.

Example 1

Irradiation Increases Net Anion Secretion

This Example shows that irradiation increases net anion secretion, and causes greater loss of villous epithelial cells as compared to crypt cells. Specifically, small intestine epithelial tissues were obtained from mice that received 12 Gy irradiation and anion secretion was examined using Ussing chamber studies. Transepithelial $I_{sc}$, an indicator of anion secretion, was measured on day 1, 2, 3, and 4.

As shown in FIG. 1A, maximal increase in transepithelial $I_{sc}$ was observed at 48 hr post irradiation, as compared to non-IR exposed tissues and IR-exposed tissues 24 and 72 hrs post irradiation (FIG. 1A). This significant increase in $I_{sc}$ at the end of 48 hrs indicates that irradiation disrupts the fine balance between absorption and secretion. In comparison, $I_{sc}$ recorded at the end of 48 hrs and 72 hrs is lower than that of non-IR mice tissues.

Histopathology sections also showed a greater loss of villous epithelial cells as compared to crypt cells due to irradiation. While histopathology sections taken before 48 hrs showed minimal villous damage and little or no crypt cell damage, histopathology sections taken on day 3 and 4 showed extensive damage in crypt and villous cells. Particularly, villous cells became almost completely depleted after day 3. The loss of crypt cells was also observed, as evidenced by a failure to stimulate anion secretion in response to a secretory stimulus at 72 and 96 hr post IR (FIG. 1A). At high doses of IR, there are insufficient crypt stem cells, which mature and differentiate to form villous epithelial cells.

Figure 1B:
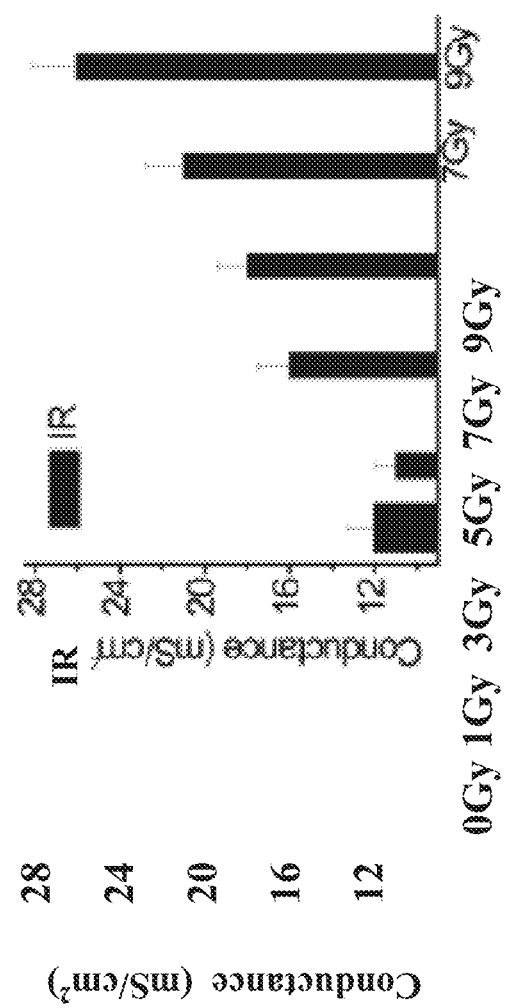
Figure 2A:
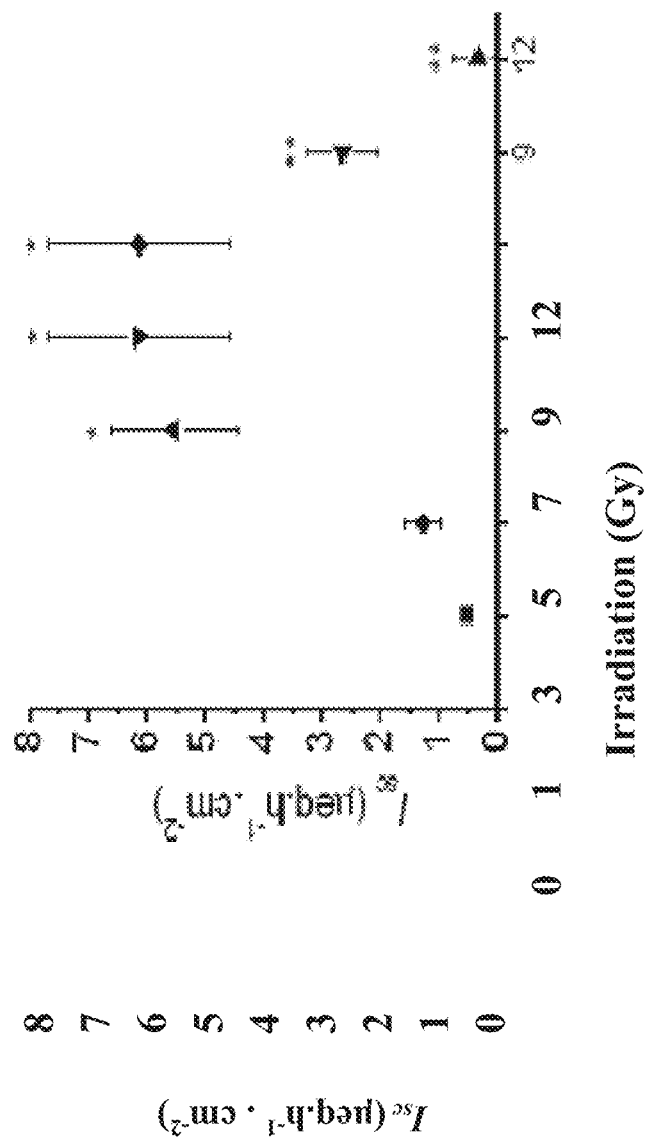
FIGS. 2A-2D show change in $I_{sc}$ with increasing dose of irradiation. All the values are derived from n=24 tissues. Experiments were performed on day 4 post-irradiation in regular Ringer solution on both sides of the chamber with a total osmolarity of 296 mosm. Histopathology sections showed minimal villous and crypt damage at 3 Gy, and extensive villous and crypt damage at 7 Gy as compared to 0 Gy.
Figure 2B:
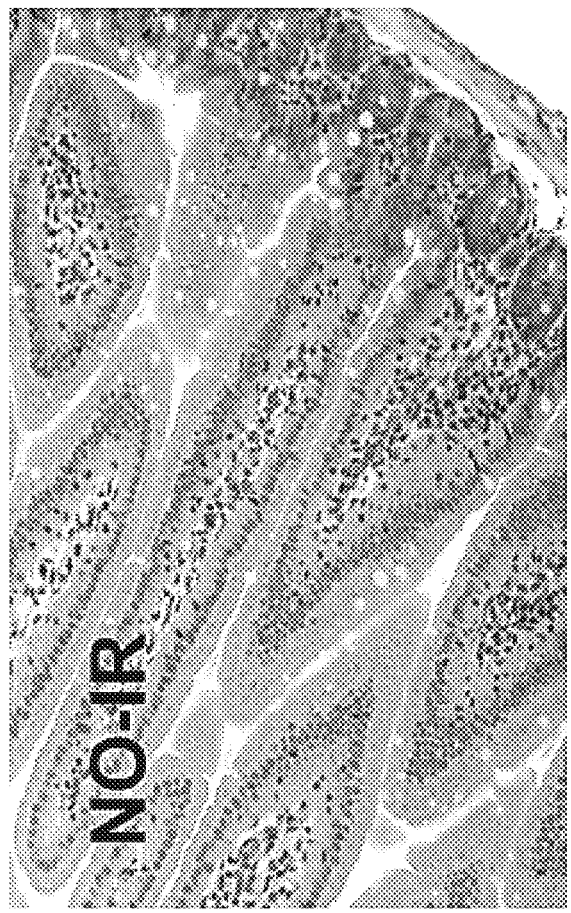
Figure 2C:
Figure 2D:
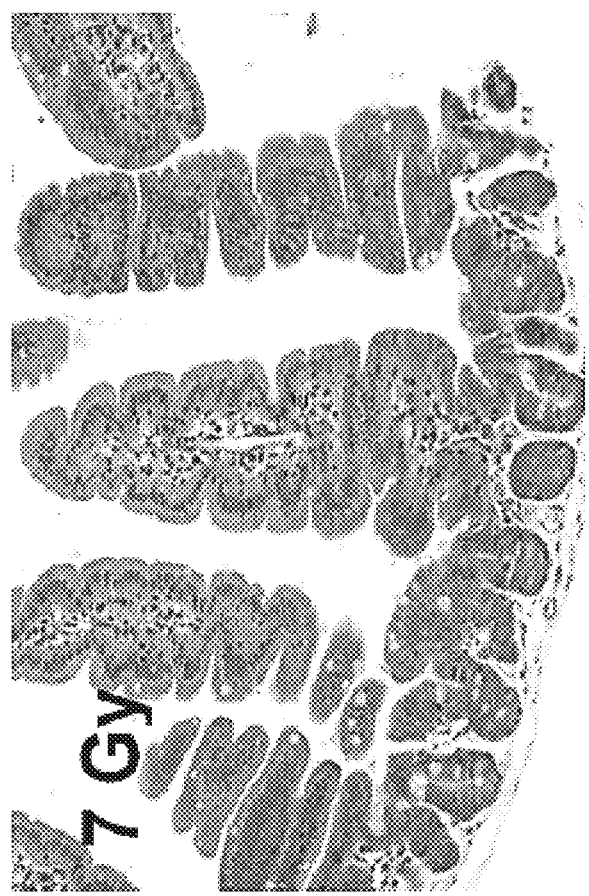

FIG. 1B shows that irradiation increased transepithelial conductance (FIG. 1B). Transepithelial conductance (S), a composite of transcellular and paracellular conductance, was measured by Ussing chamber experiments.

Based on Ohms law 1/S=R, the increase in transepithelial conductance indicates a reduction in transepithelial resistance (TER or R). Mice small intestine has low-epithelial resistance. The electrical resistance of the paracellular route is much lower than that of the transcellular resistance[65-67]. The paracellular route and the transcellular route are in parallel as shown by $1/TER=(1/R_{transcellular})+(1/R_{paracellular})$; hence, the measured TER largely reflects paracellular resistance.

Example 2

Irradiation Causes a Dose-Dependent Increase in Short Circuit Current ($I_{SC}$)

This Example reveals that irradiation causes a dose-dependent increase in short circuit current, indicating increased electrogenic anion secretion. Briefly, mice that received 0, 1, 3, 5, 7, 9 or 12 Gy irradiation were sacrificed on day 4. FIG. 2 showed significant increase in $I_{sc}$ in mice tissues irradiated at 3, 5 & 7 Gy, as compared to that of those irradiated at 0 and 1 Gy (.*.p<0.001). Compared to mice irradiated at 3, 5 and 7 Gy, decreased $I_{sc}$ was observed in mice tissues irradiated at 9 & 12 Gy (*.*.p<0.01, FIG. 2). Irradiation at between 1 and 3 Gy resulted in the highest increase in $I_{sc}$ and minimal histopathological changes.

Figure 3A:
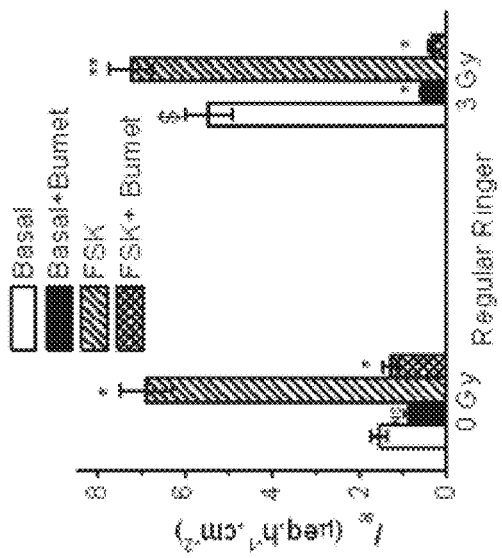

In addition, irradiation causes changes in $I_{sc}$ over time. Of mice sacrificed on 0, 1, 2, 3, 4, 5, 6 or 7 days, the highest increase in $I_{sc}$ was observed on day 5 and 6 post-IR (FIG. 3A). To determine the maximal increase in $I_{sc}$ as a function of time, mice were irradiated at 3 Gy and sacrificed on 0, 1, 2, 3, 4, 5, 6, 7, 9, 11, and 14 days to record electrical parameters. Kruskal-Wallis (P<0.001). Post-hoc analysis showed the maximal increase in $I_{sc}$ on day 6 post-irradiation.

As shown in FIG. 3A, $I_{sc}$ recorded on post-irradiation days 1 and 2 showed little statistical differences. However, $I_{sc}$ recorded on time>2 days post-irradiation showed significant differences when compared to day 0 (.*.P<0.01). Among $I_{sc}$ recorded on days 4, 5, 6, and 7, little significant difference was observed. $I_{sc}$ recorded on days 9 and 10 post-irradiation was also not significantly different from that recorded on day 7 post-irradiation (*.*. $P=_{NS}$). Although $I_{sc}$ showed a significant decrease beyond day 6, it continued to stay at an elevated level on day 14 and even 2 years post-irradiation in mice who received IR at 3-Gy (4.8±0.5 µeq·h$^{-1}$·cm$^{-2}$). FIG. 3A shows that maximal increase in $I_{sc}$ occurred on day 6 in mice irradiated at 3 Gy.

The observed increase in $I_{sc}$ post irradiation is largely due to a net increase in electrogenic anion secretion. There are three possible mechanisms for $I_{sc}$ increase: 1) increased electrogenic anion secretion (e.g., Cl$^-$ and/or HCO$_3^-$); 2) increased electrogenic Na$^+$ absorption; or 3) increased electrogenic K$^+$ absorption. It is unlikely that irradiation causes increased electrogenic Na$^+$ absorptive process in mouse small intestine. In addition, as irradiation causes diarrhea, which results in K$^+$ loss and not K$^+$ absorption, the increase in $I_{sc}$ cannot be due to increased K$^+$ absorption.

Example 3

Decrease in NA$^+$ and CL$^-$ Absorption

This Example shows that irradiation decreases Na$^+$ and Cl$^-$ absorption. As shown in Table 2, Ussing chamber flux studies using $^{22}$Na-substitution revealed that there is a net absorption of Na$^-$ in non-IR (0 Gy) mice (Table 2), as the mucosal to serosal flux ($J_{ms}$) outperforms serosa to mucosa flux ($J_{sm}$). Irradiation decreases $J_{ms}$ in a dose-dependent manner, and results in decreased net Na$^+$ absorption ($J_{Net}$Na). $J_{sm}$ far exceeds $J_{ms}$ at doses 7 and 9 Gy, causing net secretion. In addition, mice stool samples became loose or poorly formed at high dose irradiation, further evidencing decreased absorption and increased secretion of electrolytes. Similarly, net Cl$^-$ absorption also decreased as IR doses increased. Net Cl$^-$ secretion was observed at 9 Gy. Decrease in Cl$^-$ absorption was due to decrease in $J_{ms}$Cl$^-$.

TABLE 2

Unidirectional and net flux of Na$^+$ and Cl$^-$ ($J_{Net} = J_{ms} - J_{sm}$)

| | IR | | |
|---|---|---|---|
| Gy | Jms | Jsm | Jnet |
| Na Flux | | | |
| 0 | 16.4 ± 0.9 | 7.1 ± 0.8 | 9.8 ± 0.8 |
| 1 | 15.6 ± 1 | 7.1 ± 1.1 | 8.6 ± 0.9 |
| 3 | 6.8 ± 0.7 | 3.5 ± 0.3 | 2.6 ± 0.5 |
| 5 | 5.2 ± 0.6 | 4.8 ± 0.4 | 0.4 ± 0.2 |
| 7 | 4.8 ± 0.4 | 5.4 ± 0.4 | −0.6 ± 0.3 |
| 9 | 4.3 ± 0.7 | 4.7 ± 0.6 | −0.4 ± 0.2 |
| Cl Flux | | | |
| 0 | 17.3 ± 1.1 | 7.1 ± 0.6 | 10.2 ± 0.8 |
| 1 | 12.8 ± 0.9 | 7.6 ± 1.3 | 5.2 ± 0.9 |
| 3 | 16.8 ± 0.7 | 9.3 ± 0.8 | 7.5 ± 0.8 |
| 5 | 14.2 ± 1.2 | 10.3 ± 0.9 | 3.9 ± 0.7 |
| 7 | 7.1 ± 0.5 | 6.9 ± 0.3 | 0.3 ± 0.2 |
| 9 | −9.2 ± 0.8 | 0.1 ± 0.1 | −9.3 ± 0.9 |

Example 4

Irradiation Causes Increased Paracellular Permeability

Figure 4A:
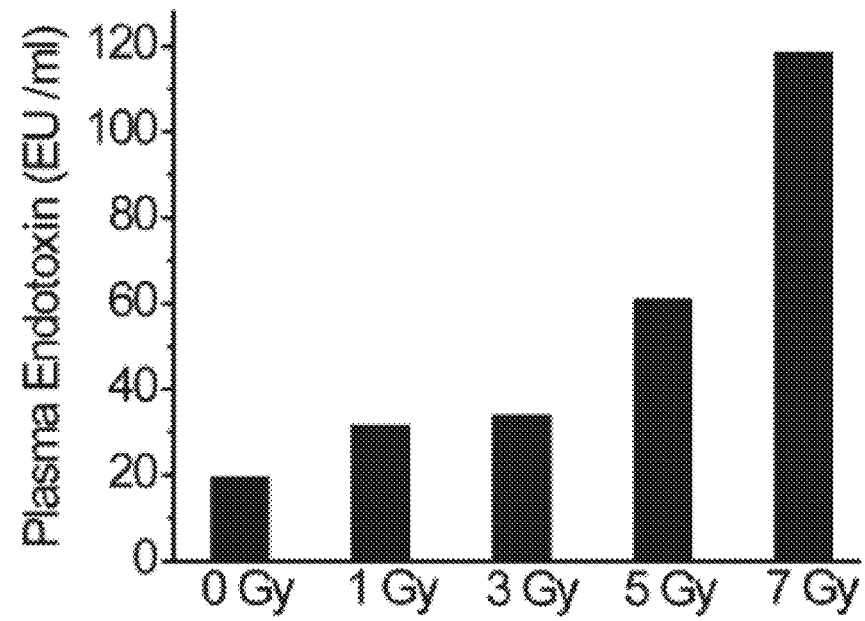
FIG. 4A shows changes in plasma endotoxin level following IR. Plasma endotoxin levels were measured on day 6, post-IR.

This Example shows that irradiation results in the loss of small intestine lining mucosa, leading to impaired small intestine barrier function. This increased small intestine permeability gives intestinal comensal bacteria, peptides and toxins easier access to systemic compartments, thereby causing endotoxemia. As shown in FIG. 4A, irradiation increases plasma endotoxin levels as measured by the tachypleus amebocyte lysate kit.

Irradiation also increased Cl$^-$ & Na$^+$ (PCl/PNa) permeability, as indicated by the changes of dilution potential determined in Ussing chamber studies. The use of dilution potential as the indicator of membrane permeability is based on the below principles. Specifically, an intact semi-permeable membrane, such as small intestine mucosa, maintains the electrochemical potential gradient artificially generated by bathing mucosal and serosal side solutions with different ionic strength. A leaky membrane that allows easy diffusion across the membrane, however, has diminished membrane electrochemical potential. Thus, the higher the permeability across the membrane, the lower the potential gradient is. A freely permeable membrane has a relative permeability of Cl$^-$ and Na$^+$ (PCl/PNa) at 1, which indicates a complete loss of selectivity.

Figure 4B:
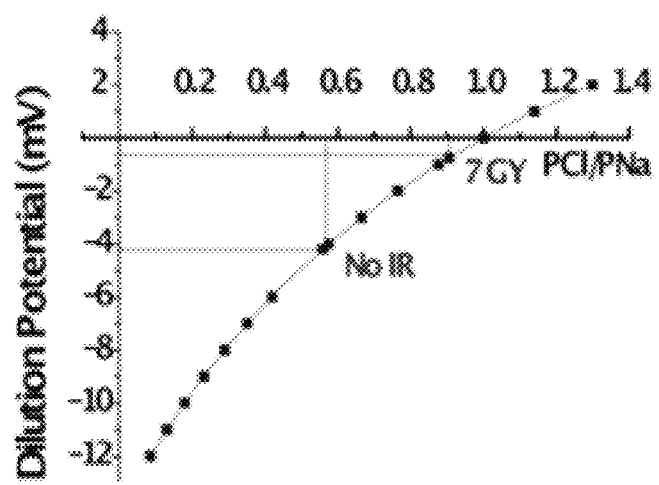
FIG. 4B shows changes in permeability ratio of Cl⁻ & Na⁺ plotted against changes in membrane voltage (Dilution potential). Irradiation at 7 Gy causes a complete loss of selectivity.

In non-IR mice, the membrane selectivity is preserved and Na$^+$ is more permeable than Cl$^-$ across the membrane. Irradiation decreased membrane dilution potential. Particularly, Na$^+$ and Cl$^-$ became equally permeable across the membrane at 7 Gy, indicating a significant loss of selectivity (FIG. 4B). The increase in electrolyte permeability due to irradiation is consistent with the increase in plasma endotoxin levels shown in FIG. 4A. Monitoring changes in membrane permeability can be used as a sensitive tool to monitor improvement in mucosal barrier function by the subject oral radiation diet.

Example 5

Increase in Levels of Inflammatory Mediators Due to Irradiation

Figure 5A:
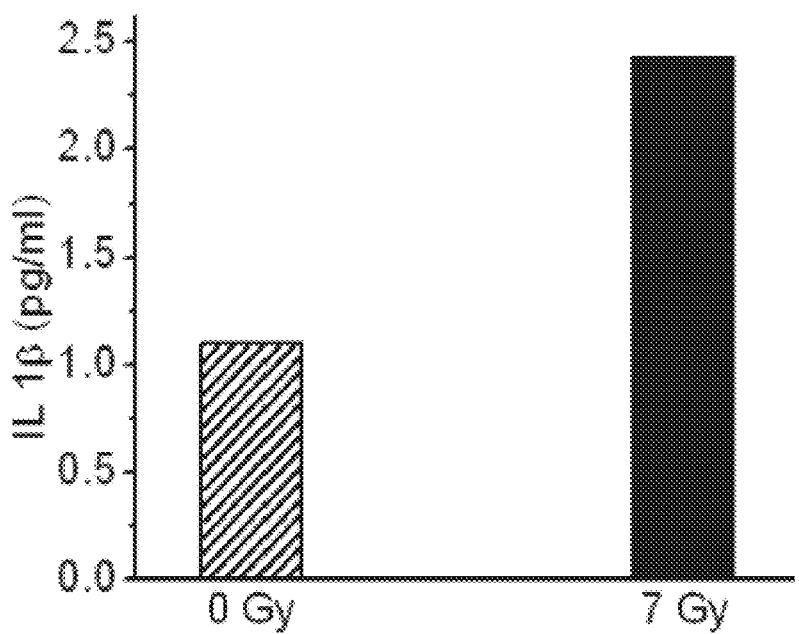
FIGS. 5A-5C show that irradiation increases levels of inflammatory mediators, including IL-1β, TNFα and MIP-α.
Figure 5B:
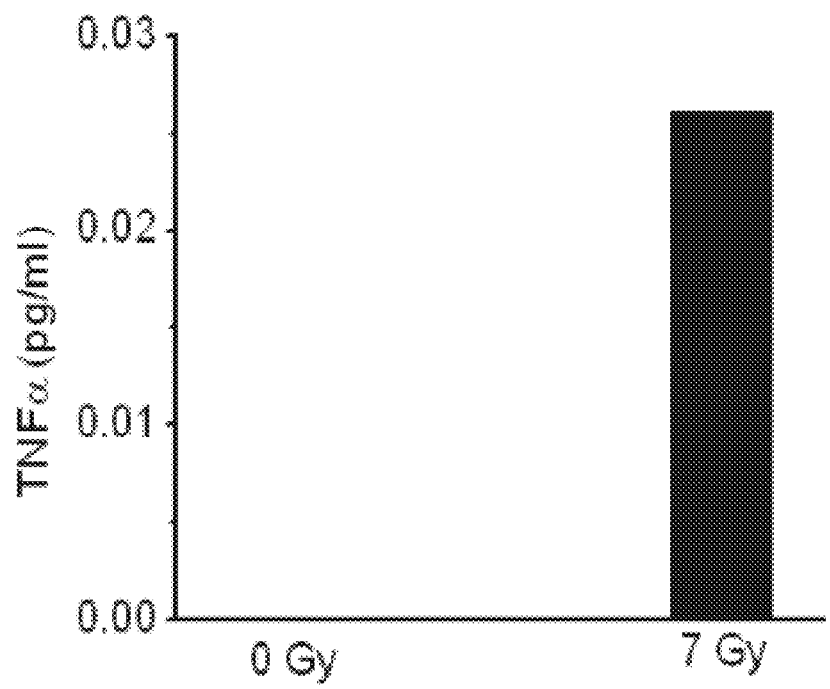
Figure 5C:
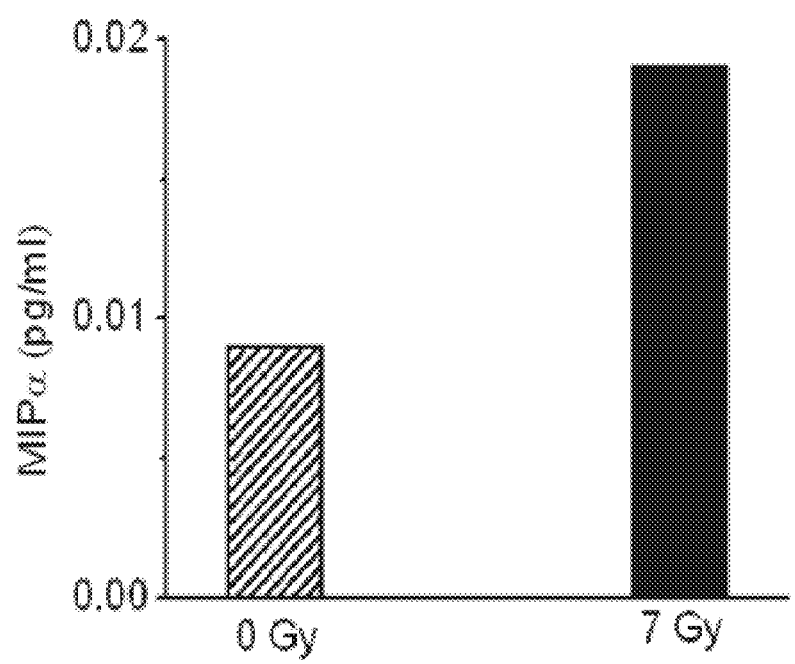
Figure 6A:
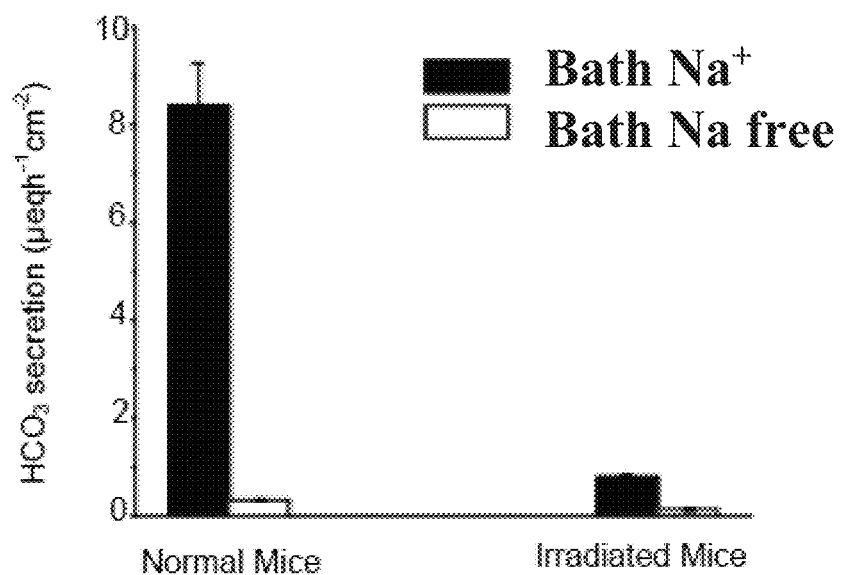
FIGS. 6A-6E show changes in $HCO_3^-$ secretion due to irradiation and immunostaining for $HCO_3^-$ secretory machinery. (6A) shows effects of irradiation on bath Na⁺ on $HCO_3^-$ secretion. Experiments were performed in A) in Cl-containing solutions with 140 mM Na⁺ or B) Cl⁻ containing solutions without Na⁺. Tissues were stimulated with forskolin. $HCO_3^-$ secretion was compared to that of between 0 Gy and 3 Gy irradiated mice. Significantly higher bath Na⁺— dependent $HCO_3^-$ secretion was observed in 0 Gy as compared to 3 Gy irradiated mice (p<0.001). Results are derived from n=6 tissues. Error bars represent S.E.M. (6B-6E) show immunostaining of jejunum tissues of mice received 0 Gy and 3 Gy irradiation, using NBCe1 a/b antibody.
Figure 6B:
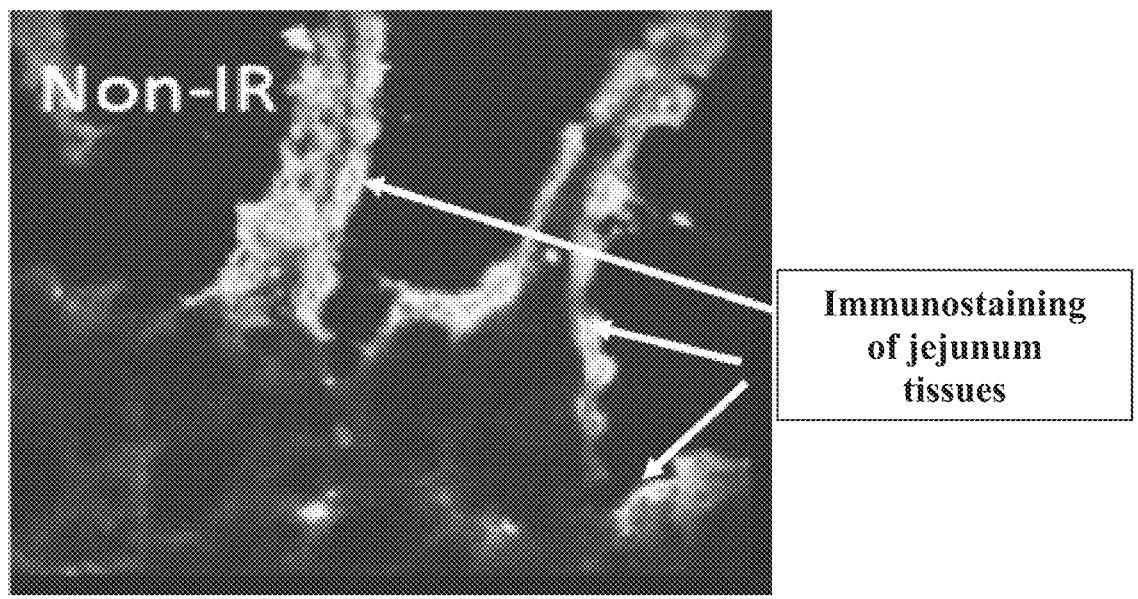
Figure 6C:
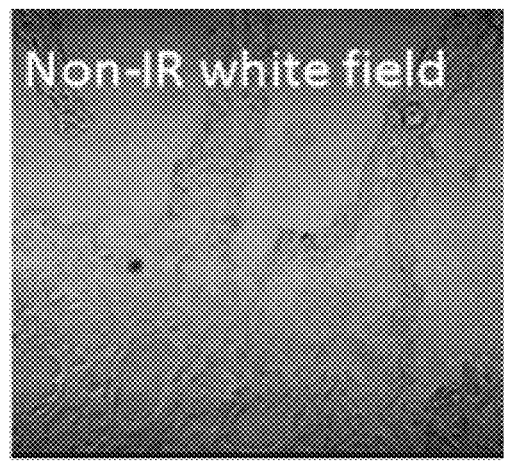
Figure 6D:
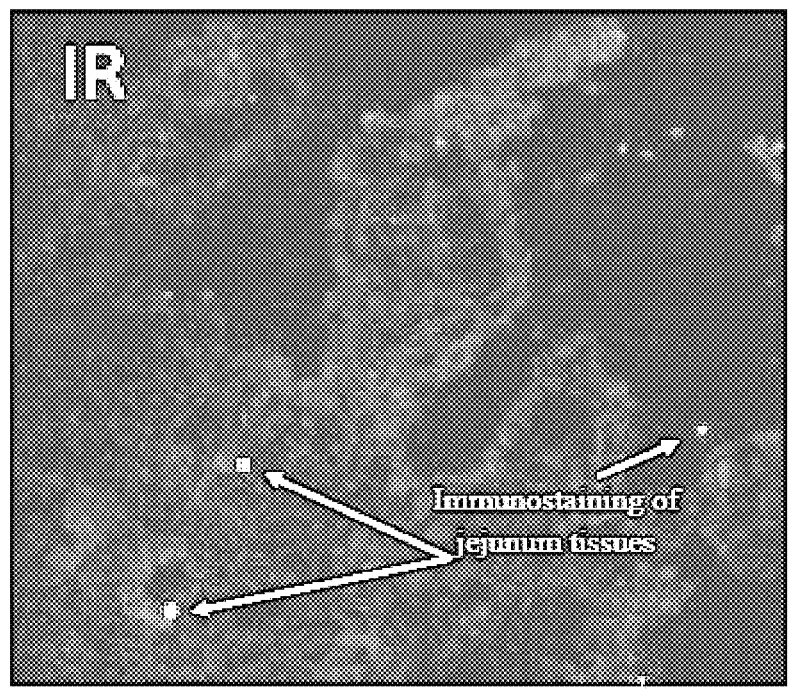
Figure 6E:
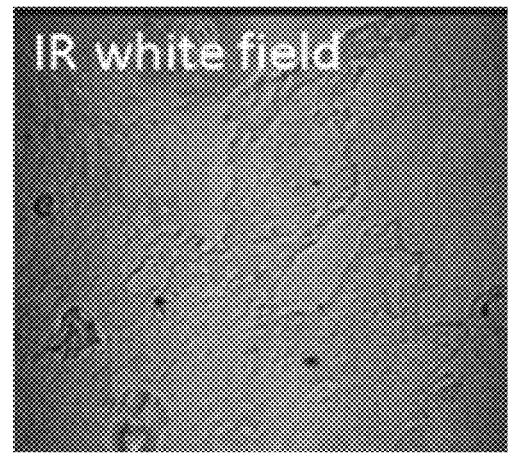

Levels of inflammatory mediators in IR-exposed and non-IR exposed mice were measured using LUMINEX multiplex bead array techniques. As shown in FIG. 5, irradiation increased the production of IL1-β, TNF-α and MIP-α (FIG. 5).

Example 6

Figure 3C:
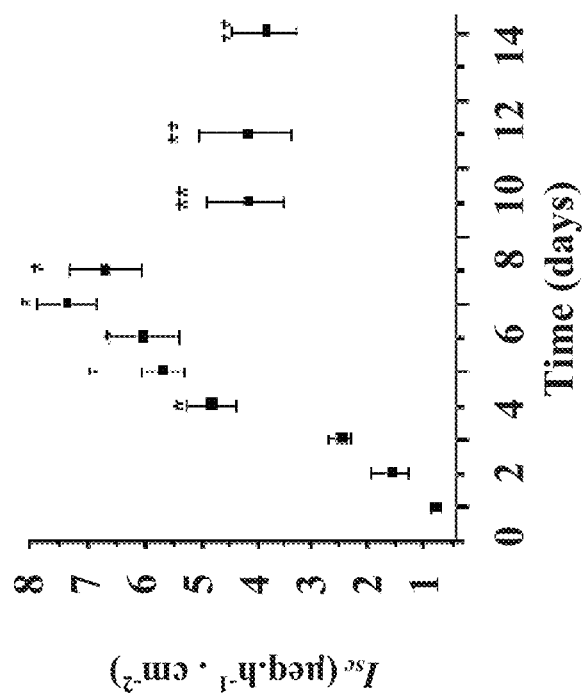
FIG. 3C shows the effect of bumetanide on basal and cAMP-stimulated $I_{sc}$ in non-irradiated and 3-Gy irradiated tissues.

Decreased in Anion Secretion Due to Irradiation is NKCC1-Dependent and CFTR-Dependent This Example shows that anion secretion under irradiation is NKCC1-dependent and CFTR-dependent. To determine the contribution of NKCC1 to basal $I_{sc}$, 100 µM bumetanide (Sigma-Aldrich Co., USA) was added to the bath solution. FIG. 3C showed a bumetanide-inhibitable current in irradiated tissues (5.5±0.5 µeq·h$^{-1}$·cm$^{-2}$ vs. 0.6±0.1 µeq·h$^{-1}$·cm$^{-2}$), but not in 0-Gy mice (1.6±0.2 µeq·h$^{-1}$·cm$^{-2}$ vs. 0.9±0.1 µeq·h$^{-1}$·cm$^{-2}$). In addition, cAMP-stimulation caused an increase in $I_{sc}$ in both 0-Gy (1.6±0.2 µeq·h$^{-1}$·cm$^{-2}$ vs. 6.9±0.6 µeq·h$^{-1}$·cm$^{-2}$, P<0.001) and 3-Gy irradiated mice (5.5±0.5 µeq·h$^{-1}$·cm$^{-2}$ vs. 7.3±0.5 µeq·h$^{-1}$·cm$^{-2}$, P<0.05).

In addition, forskolin (Sigma-Aldrich Co., USA)-stimulated $I_{sc}$ was abated by bumetanide in 3 Gy (7.3±0.5 µeq·h$^{-1}$·cm$^{-2}$ vs. 0.4±0.1 µeq·h$^{-1}$·cm$^{-2}$), but not in 0 Gy (6.9±0.6 µeq·h$^{-1}$·cm$^{-2}$ vs. 1.3±0.2 µeq·h$^{-1}$·cm$^{-2}$). This indicates greater NKCC1-independent anion secretion without irradiation (P<0.05).

Figure 3B:
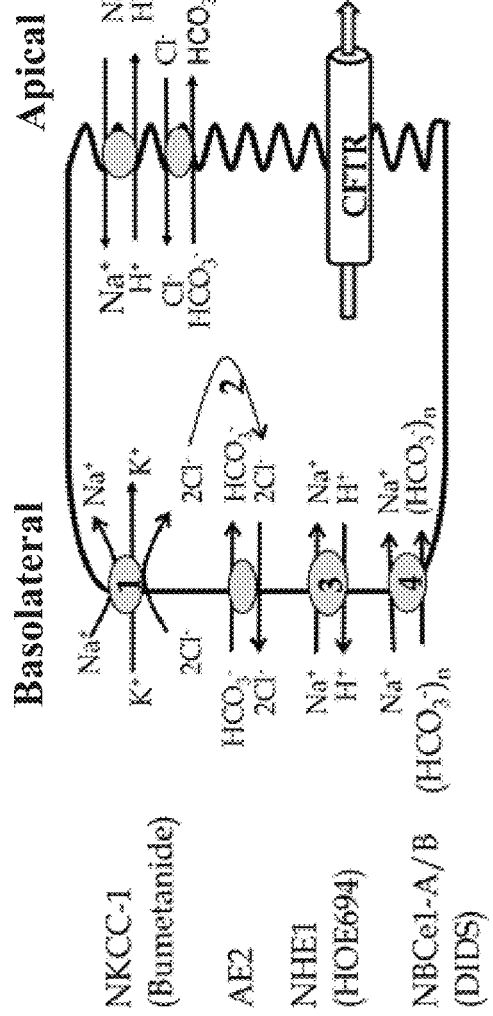
FIG. 3B shows ion transport of a small intestine epithelial cell.

The results also showed that anion secretion under irradiation is CFTR-dependent. To determine whether the bumetanide-insensitive portion of $I_{sc}$ occurs via an apical membrane anion channel, a non-specific anion channel blocker, 5-nitro-2-(3-phenylpropylamino)-benzoic acid (Sigma-Aldrich Co., USA) (10 µM NPPB), and a specific cystic fibrosis transmembrane conductance regulator (CFTR) blocker (100 µM glibenclamide, Sigma-Aldrich Co., USA) were applied. Bumetanide-insensitive $I_{sc}$ in 0-Gy mice was abolished by mucosal addition of a non-specific anion channel blocker (NPPB) (0.1±0.01 µeq·h$^{-1}$·cm$^{-2}$) and glibenclamide (0.1±0.01 µeq·h$^{-1}$·cm$^{-2}$). This indicates that anion secretion occurs via an anion channel or CFTR (FIG. 3B).

Example 7

Decrease in HCO$_3^-$ Secretion Due to Irradiation

Infective diarrhea, such as cholera, results in the loss of HCO$_3^-$-rich fluid in stool and leads to metabolic acidosis. This Example shows that, in contrast to infective diarrhea, IR induced increased Cl$^-$ secretion and decreased HCO$_3^-$ secretion.

To determine the contribution of Cl$^-$ to net anion secretion, a blocker for Cl$^-$ uptake into the cell (Na—K-2Cl cotransport blocker) was employed. Addition of 10 µM bumetanide abolished almost all of the $I_{sc}$ associated with IR, suggesting that IR-induced anion secretion is primarily due to increased Cl$^-$ secretion and such increase is NKCC1-dependent (FIGS. 3A-C).

pH stat experiments confirmed that IR reduced HCO$_3^-$ secretion (Table 3). HCO$_3^-$ secretion was abolished when Na$^+$ in the serosal bathing solution (bath) was replaced with an impermeable cation NMDG, indicating that transport of HCO$_3^-$ into the cell at basolateral membrane is bath Na$^+$ dependent. Similar experiments were repeated in 5 Gy, day 6 post IR mice. In the presence of bath Na$^+$, HCO$_3^-$ secretion was significantly lower.

Immunofluorescence staining of frozen tissue slices obtained from both non-IR and IR mice was performed using NBCe1a/b antibodies (FIGS. 6B-E). NBCe1a/b antibody-specific staining showed that NBCe1a/b was expressed in the villous epithelial cells, but not in the crypt cells. Immunostaining of tissues from IR mice showed that NBCe1a/b antibodies were not recognized either in the villous or in the crypt. Tissues from mice irradiated with 3 Gy (IR) failed to express NBCe1-A/B-specific staining pattern either in the villous or in the crypt. Decreased $HCO_3^-$ secretory function at high doses of IR is due to the loss of villous epithelial cells. Monitoring changes in $Na^+$ and $HCO_3^-$ secretion can be a sensitive tool to monitor improvement of mucosal barrier function by the subject oral radiation diet.

$HCO_3^-$ Secretion Under Irradiation is NKCC1-Independent

Figure 3D:
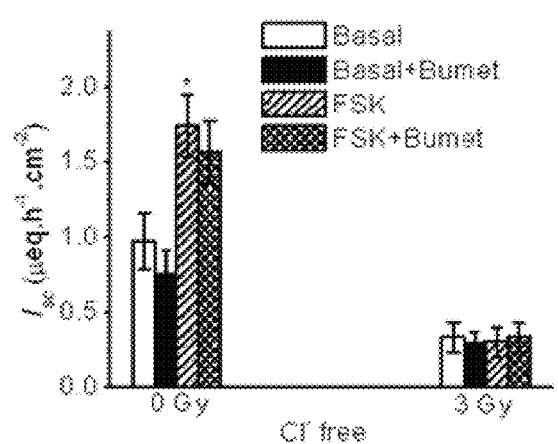
FIG. 3D shows the contribution of $HCO_3^-$ in net anion secretion. This was determined by replacing Cl⁻ in Ringer solution with equimolar amounts of isethionate. Forskolin stimulated an increase in $I_{sc}$ in 0 Gy (*. p<0.02) but not in 3 Gy tissues.

To determine if $HCO_3^-$ contributed to anion secretion, experiments were performed in the absence of bath $Cl^-$. An increase in $I_{sc}$ secondary to irradiation or forskolin-stimulation was considered to be contributed by $HCO_3^-$. The results showed that $HCO_3^-$ secretion under irradiation is not bath $Cl^-$-dependent; therefore, under irradiation, $HCO_3^-$ secretion does not involve the $Cl^-$—$HCO_3$ exchange transporter (AE1) in the apical membrane. In $Cl^-$-free solution, basal ($1.0\pm0.2$ $\mu eq \cdot h^{-1} \cdot cm^{-2}$ vs $0.3\pm0.1$ $\mu eq \cdot h^{-1} \cdot cm^{-2}$; P=ns) and forskolin-stimulated ($1.7\pm0.2$ $\mu eq \cdot h^{-1} \cdot cm^{-2}$ vs. $0.3\pm0.1$ $\mu eq \cdot h^{-1} \cdot cm^{-2}$; P<0.001) $I_{sc}$ was lower in 3-Gy irradiated mice (FIG. 3D). Forskolin-stimulated $I_{sc}$ was higher in 0 Gy than in 3 Gy (P<0.001), indicating a decrease in $HCO_3^-$ secretion due to irradiation.

To ascertain if NKCC1 mediated $HCO_3^-$ movement under basal and forskolin-stimulated conditions, bumetanide was added to the bath side of tissues equilibrated in $Cl^-$-free solution on both sides. The results showed that bumetanide did not inhibit basal and forskolin-stimulated increase in $I_{sc}$; this lack of inhibition indicates a NKCC1-independent mechanism for $HCO_3^-$ uptake at the basolateral membrane.

$HCO_3^-$ Secretion Under Irradiation is Lumen $Cl^-$-Independent

Figure 19A:
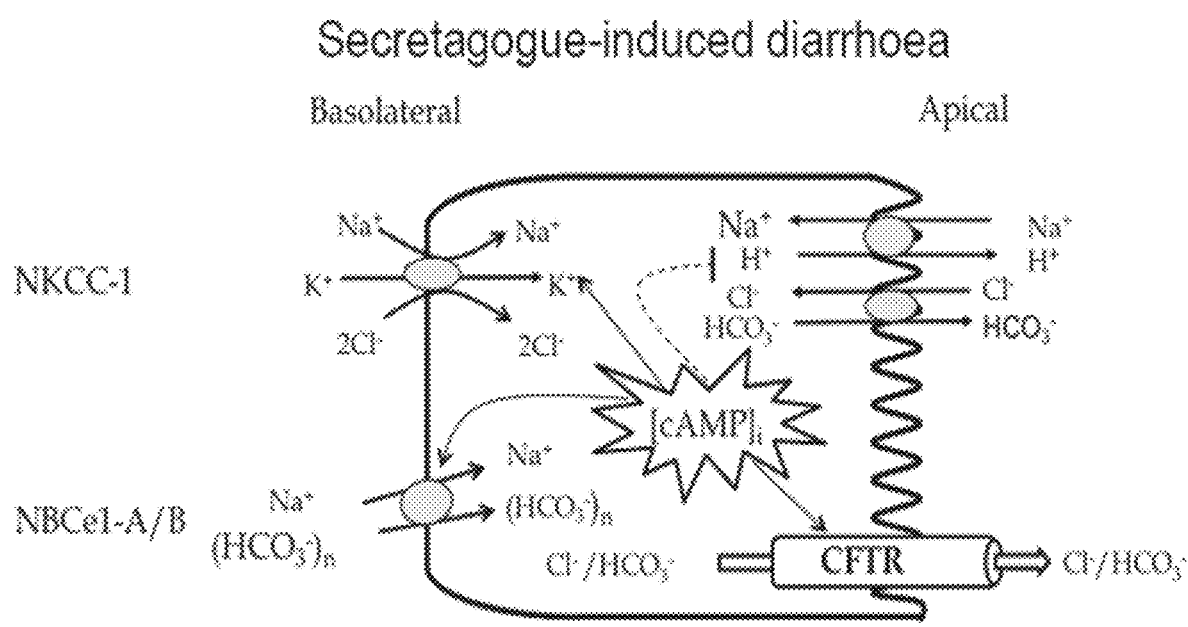
FIGS. 19A-19B show schematic models for cAMP-stimulated (19A) and irradiation-induced (19B) anion secretion.
Figure 19B:
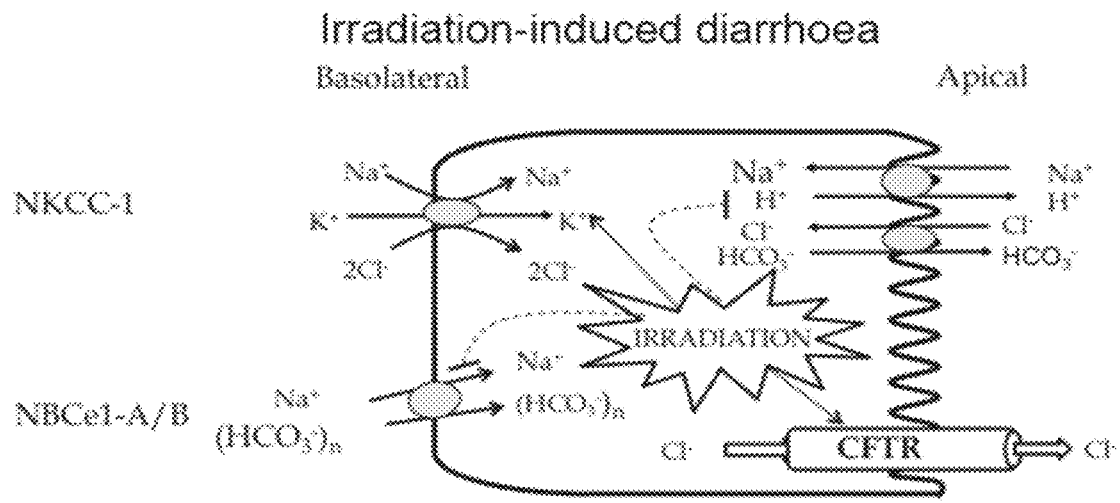

Direct measurement of $HCO_3^-$ secretion in irradiated mice showed reduced $HCO_3^-$ secretion compared to non-irradiated mice ($0.8\pm0.2$ $\mu eq \cdot h^{-1} \cdot cm^{-2}$ vs. $6.7\pm0.2$ $\mu eq \cdot h^{-1} \cdot cm^{-2}$). $HCO_3^-$ secretion in irradiated mice was unaltered by removal of lumen $Cl^-$ (Table 3). The mucosal addition of NPPB ($0.2\pm0.01$ $\mu eq \cdot h^{-1} \cdot cm^{-2}$) and glibenclamide ($0.11\pm0.1$ $\mu eq \cdot h^{-1} \cdot cm^{-2}$), but not DIDS, ended $HCO_3^-$ secretion in irradiated mice. This indicates that $HCO_3^-$ secretion is mediated by an anion channel (CFTR channel), not via $Cl^-$—$HCO_3^-$ exchange (FIG. 19B).

In comparison, $HCO_3^-$ secretion in non-irradiated mice is both lumen $Cl^-$-dependent and $Cl^-$-independent. Transepithelial electrical measurements indicated electrogenic $HCO_3^-$ secretion; however, this does not indicate whether $HCO_3^-$ secretion was channel-mediated and/or via electroneutral $Cl^-$—$HCO_3^-$ exchange.

pH-stat experiments were performed in the absence of lumen $Cl^-$ to study $Cl^-$—$HCO_3^-$ exchange in non-irradiated mice. In a lumen $Cl^-$-free solution, $HCO_3^-$ secretions were lower ($4.5\pm0.1$ $\mu eq \cdot h^{-1} \cdot cm^{-2}$, P<0.01). This indicates that basal $HCO_3^-$ secretion in non-irradiated mice is partly lumen $Cl^-$-dependent and partly $Cl^-$-independent (Table 3). The addition of 100 µM 4,4-diisothiocyano-2,2'-stilbene disulfonic acid (DIDS) (Sigma-Aldrich Co., USA) partially inhibited $HCO_3^-$ secretion (P<0.001), and such inhibition was similar to that observed with lumen $Cl^-$ removal.

Forskolin Stimulated Lumen $Cl^-$-Independent $HCO_3^-$ Secretion

For 0-Gy mice, addition of forskolin to the bath solution showed significant increases in basal $HCO_3^-$ secretion (P<0.001) that was not altered by lumen $Cl^-$ removal ($8.4\pm0.4$ $\mu eq \cdot h^{-1} \cdot cm^{-2}$ vs. $8.7\pm0.4$ $\mu eq \cdot h^{-1} \cdot cm^{-2}$; n=6). NPPB abolished forskolin-stimulated $HCO_3^-$ secretion ($0.2\pm0.01$ $\mu eq \cdot h^{-1} \cdot cm^{-2}$; n=6); this indicated a role for an anion channel in cAMP-stimulated $HCO_3^-$ secretion.

cAMP-Stimulated $HCO_3^-$ Secretion is NKCC1-Independent

To determine if cAMP-stimulated $HCO_3^-$ secretion required an apical CFTR channel, glibenclamide was added to the luminal side. Glibenclamide inhibited ($0.1\pm0.1$ $\mu eq \cdot h^{-1} \cdot cm^{-2}$) $HCO_3^-$ secretion (Table 3 and FIG. 19A), indicating that cAMP not only inhibits the basal $Cl^-$—$HCO_3^-$ exchange component of the net $HCO_3^-$ secretion, but also induces an apical anion channel-mediated $HCO_3^-$ secretion. Forskolin stimulation in irradiated mice showed little increase compared to basal $HCO_3^-$ secretion ($0.6\pm0.2$ $\mu eq \cdot h^{-1} \cdot cm^{-2}$ vs. $0.78\pm0.2$ $\mu eq \cdot h^{-1} \cdot cm^{-2}$). This also indicates a lumen $Cl^-$-independent $HCO_3^-$ secretion or the inhibition of $Cl^-$—$HCO_3^-$ exchange.

Transepithelial electrical measurements showed that decrease in $HCO_3^-$ movement was also NKCC1-independent. $HCO_3^-$ secretion, which was minimal in irradiated mice under both basal and forskolin-stimulated conditions, was unaffected by the addition of bumetanide (Table 3). Similarly, in non-irradiated mice, bumetanide did not alter forskolin-stimulated $HCO_3^-$ secretion, indicating that the cAMP-stimulated $HCO_3^-$ secretion is NKCC1-independent ($8.4\pm0.4$ $\mu eq \cdot h^{-1} \cdot cm^{-2}$ vs. $8.6\pm0.4$ $\mu eq \cdot h^{-1} \cdot cm^{-2}$) (Table 3 and FIG. 3B).

$HCO_3^-$ Secretion is Bath $Cl^-$-Independent

Transport processes requiring bath $Cl^-$ for basolateral $HCO_3^-$ uptake are shown in FIG. 3B. The results showed that bumetanide did not alter the cAMP-stimulated $HCO_3^-$ secretion. This indicated that $Cl^-$—$HCO_3^-$ exchange (AE2) transporter is inhibited under irradiation. Removal of bath $Cl^-$ can also inhibit NKCC1 and AE2-linked $HCO_3^-$ uptake (Table 3). Removal of $Cl^-$ from the bath solution did not alter $HCO_3^-$ secretion ($6.7\pm0.3$ $\mu eq \cdot h^{-1} \cdot cm^{-2}$ vs. $7.1\pm0.6$ $\mu eq \cdot h^{-1} \cdot cm^{-2}$).

$HCO_3^-$ Secretion is Bath $Na^+$-Dependent

Transport processes for the $Na^+$-coupled, basolateral, $HCO_3^-$ entry are shown in FIG. 3B. FIGS. 3C and 3D indicated that NKCC1 does not affect $HCO_3^-$ secretion. Addition of 1mM 3-methylsulphonyl-4-piperidinobenzoyl, guanidine hydrochloride (HOE694) to the bath side eliminated $HCO_3^-$ uptake via NHE1 coupled to $Cl^-$—$HCO_3^-$ exchange. Counillon, Scholz et al. (1993) also described that 1 mM 3-methylsulphonyl-4-piperidinobenzoyl, guanidine hydrochloride (HOE694) could inhibit $Na^+$—$H^+$ exchange (NHE1).

Figure 3E:
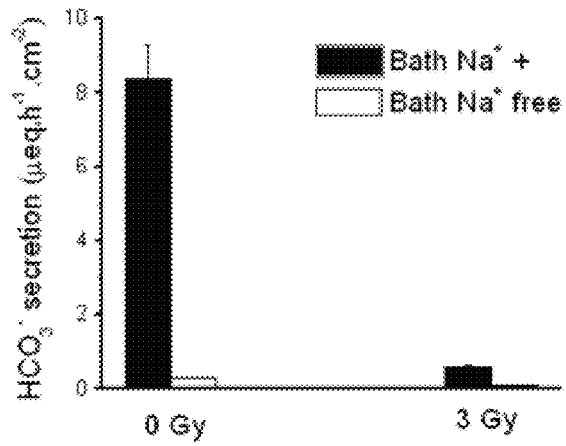
FIG. 3E shows effect of bath Na⁺ on $HCO_3^-$ secretion. All of the results shown in FIG. 3 are from n=6 tissues. Error bars represent SEM.

HOE694 did not inhibit cAMP-stimulated $HCO_3^-$ secretion ($8.4\pm0.4$ $\mu eq \cdot h^{-1} \cdot cm^{-2}$ vs. $7.2\pm0.9$ $\mu eq \cdot h^{-1} \cdot cm^{-2}$). Replacing bath $Na^+$ with N-methyl-D-glucamine (NMDG) abolished forskolin-stimulated $HCO_3^-$ secretion ($8.4\pm0.4$ $\mu eq \cdot h^{-1} \cdot cm^{-2}$ vs. $0.3\pm0.01$ $\mu eq \cdot h^{-1} \cdot cm^{-2}$) in non-irradiated mice, which indicates a $Na^+$-coupled $HCO_3^-$ cotransport (NBC) (FIG. 3E).

TABLE 3

HCO$_3^-$ secretion measured in the jejunum of non-irradiated (0 Gy) and irradiated (3 Gy) mice.

| Lumen solution | Cl$^-$ containing | Cl$^-$-free | 100 μM DIDS | 100 μM glibenclamide |
| --- | --- | --- | --- | --- |
| 0 Gy | 6.7 ± 0.3 | 4.5 ± 0.1$^‡$ | 4.4 ± 0.1$^‡$ | 0.5 ± 0.1 |
| 3 Gy | 0.8 ± 0.2* | 0.6 ± 0.1 *$^{ns}$ | 0.9 ± 0.2 *$^{ns}$ | 0.1 ± 0.1 $^{ns}$ |
| 0 Gy + forskolin | 8.4 ± 0.4 | 8.7 ± 0.4 | — | 0.1 ± 0.1 |
| 3 Gy + forskolin | 0.6 ± 0.2 | 0.9 ± 0.2 | — | — |
| 0 Gy + bumetanide | 8.6 ± 0.4 | 8.4 ± 0.4 | 7.7 ± 0.4 | 0.5 ± 0.1 |
| 3 Gy + bumetanide | 0.8 ± 0.14* | 0.8 ± 0.1 $^{ns}$ | 0.7 ± 0.12 $^{ns}$ | 0.2 ± 0.1 $^{ns}$ |

Note:
Values represent mean ± SEM n = 6 tissues.
*p < 0.001, comparison between 0 Gy and 3 Gy group.
$^‡$p < 0.001 comparison between presence groups. In bumetanide experiments in non-irradiated mice, the tissues were treated with 10 mM forskolin.
Abbreviations:
$^{ns}$, no significance between the groups;
4,4-diisothiocyano-2,2'-stilbene disulfonic acid, DIDS For active HCO$_3^-$ secretion at the apical membrane, there is a need for its basolateral uptake. Four known exchange mechanisms directly or indirectly involved with HCO$_3^-$ movement at the basolateral membrane are: 1) Na$^+$—K$^+$-2Cl$^-$ co-transport (Na$^-$—K$^+$-2HCO$_3^-$) as a possible transporter of HCO$_3^-$; 2) Cl$^-$ uptaken into the cell via NKCC1 is recycled via basolateral Cl$^-$—HCO$_3^-$ exchange (AE2), resulting in net HCO$_3^-$ uptake at the basolateral membrane; 3) Na$^+$—H$^+$ exchange extruding protons into intercellular space, resulting in decreased intracellular HCO$_3^-$ concentration, which then stimulates apical electroneutral HCO$_3^-$ exchange; and 4) Na$^+$ coupled HCO$_3^-$ cotransport. These transporters may function as electroneutral or electrogenic, depending on the number of HCO$_3^-$ molecules transported per molecule of Na$^-$ (FIG. 3B).

In non-irradiated mice, HCO$_3^-$ uptake occurs via a Na$^+$-coupled HCO$_3^-$ cotransporter (NBCe1-A/B) located at the basolateral surface. Apical exit occurs via an electroneutral Cl$^-$/HCO$_3^-$ exchange that is coupled to a Na$^+$—H$^+$ exchange and via CFTR (electrogenic anion secretion). An increase in intracellular cAMP, achieved by the addition of forskolin, results in increased Cl$^-$ and HCO$_3^-$ secretion with simultaneous inhibition of electroneutral Na$^+$ and Cl$^-$ absorption (Na$^+$—H$^-$ exchange coupled to Cl$^-$—HCO$_3^-$ exchange). Cl$^-$ uptake occurs via NKCC1, and HCO$_3^-$ uptake occurs via NBCe1-A/B; both Cl$^-$ and HCO$_3^-$ exit via CFTR at the apical surface.

In accordance with the subject invention, it has been discovered that irradiation inhibits electroneutral Na$^+$ and Cl$^-$ absorption. Irradiation also inhibits NBCe1-A/B, and such inhibition results in decreasing HCO$_3^-$ uptake at the basolateral membrane and finally its exit at the apical membrane. Thus, irradiation results in electrogenic Cl$^-$ secretion with selective inhibition of both electroneutral and electrogenic HCO$_3^-$ secretion (FIG. 19B).

Irradiation caused increased NKCC-1 protein expression and decreased NBCe1-A/B expression in the small intestine epithelium tissues. Irradiation also inhibits the apical Cl$^-$—HCO$_3^-$ exchange transporter (AE1). HCO$_3^-$ secretion in radiation diarrhea is Na$^+$-dependent, but lumen Cl$^-$ independent and NKCC-1-independent. Cl$^-$ transport under irradiation involves the basolateral NKCC1 transporter, instead of a Cl$^-$—HCO$_3^-$ exchange transporter (AE1).

As shown in FIG. 19B, irradiation also alters electrolyte (such as HCO$_3^-$ and Cl$^-$) transport in the gastrointestinal tract. Irradiated mice exhibited primarily Cl$^-$ secretion, and minimal HCO$_3^-$ secretion. It is postulated that minimal HCO$_3^-$ secretion due to irradiation is caused by the inhibition of HCO$_3^-$ absorption. In contrast, there is active Cl$^-$ as well as HCO$_3^-$ secretion in secretagogue-induced diarrhea.

Example 8

Irradiation Causes Reduced Glucose Absorption

Figure 7A:
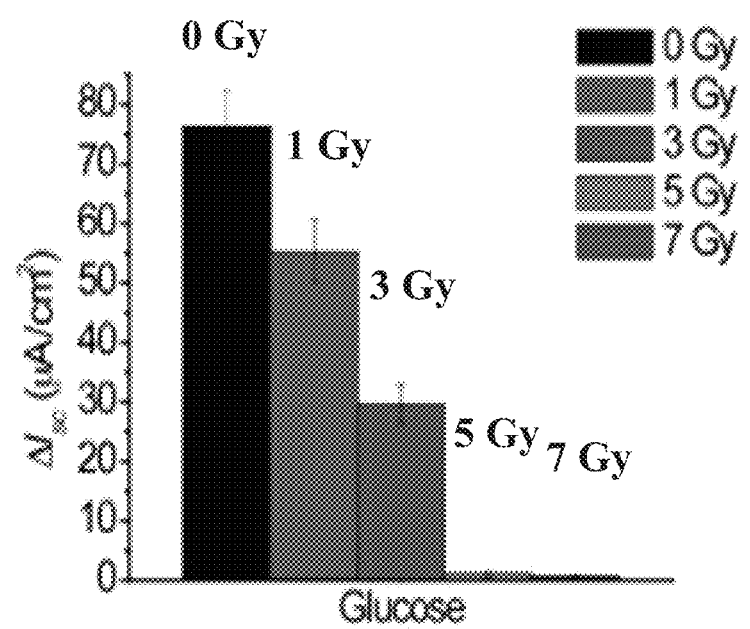
FIGS. 7A-7B show IR dose-dependent changes in glucose transport and kinetics. (7A) shows that irradiation resulted in a dose-dependent decrease in glucose-stimulated Na⁺ $I_{sc}$ measured in Ussing chamber. (7B) shows decreased SGLT1 affinity for glucose as irradiation doses increased.
Figure 7B:
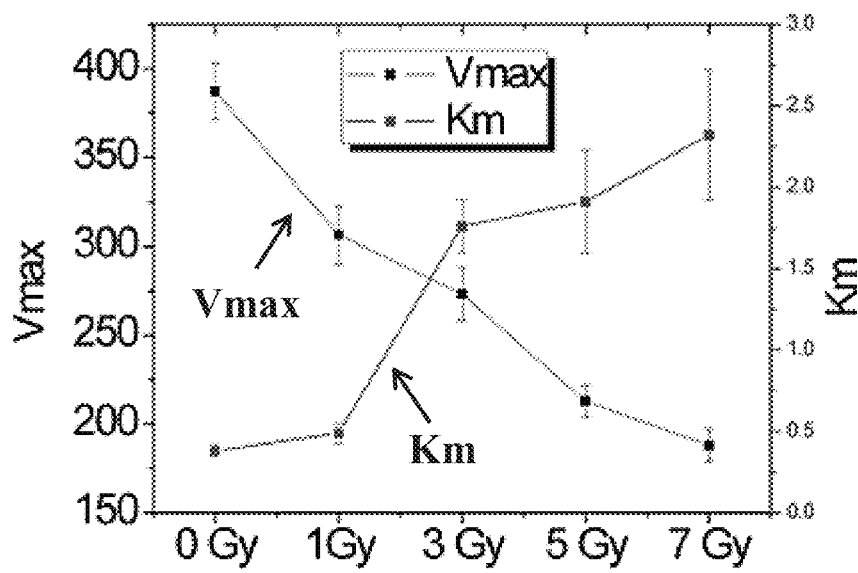
Figure 8:
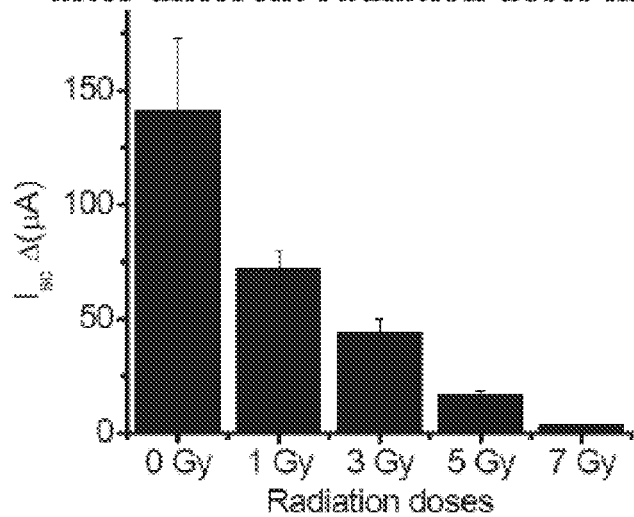
FIG. 8 shows that irradiation reduced glucose-stimulated current in a dose-dependent manner starting from irradiation at 1 Gy. Irradiation at 7 Gy almost completely inactivated glucose transport.
Figure 9A:
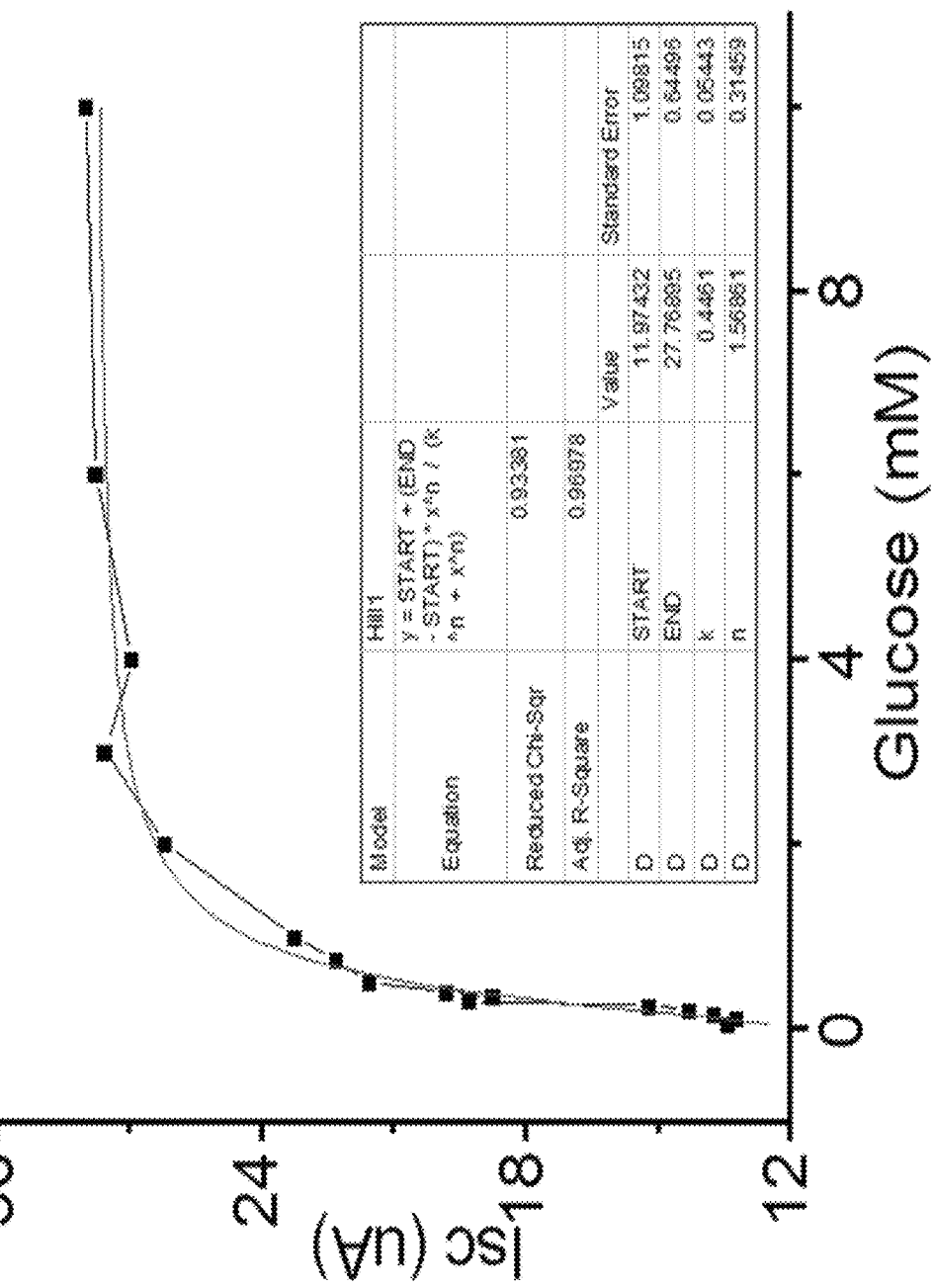
FIG. 9A displays short-circuit current, showing saturated kinetics with increase in glucose concentration. Particularly, glucose transport is saturated at a concentration of 4 mM.
Figure 9B:
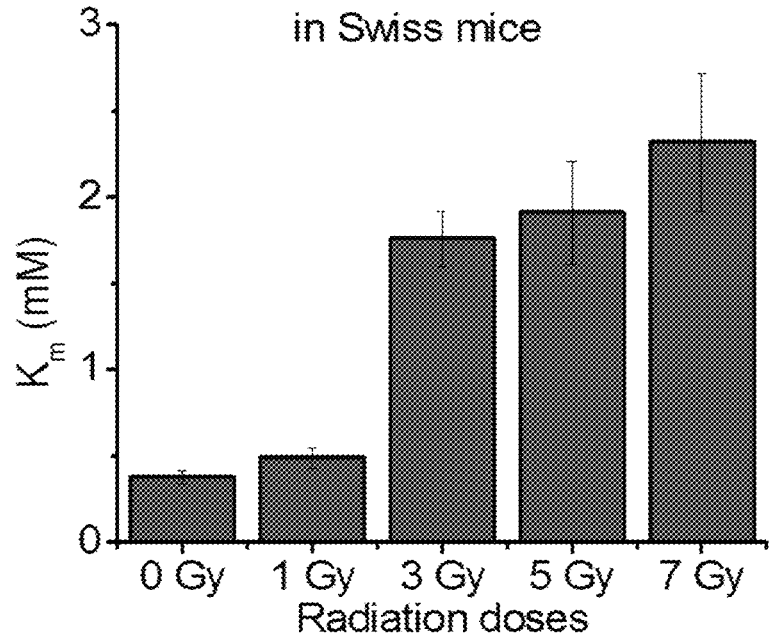
FIG. 9B shows irradiation dose-dependent increase in $K_m$ values. The maximal increase in $K_m$ was observed at 7 Gy. This indicates that irradiation caused decreased affinity of SGLT-1 to glucose.
Figure 10:
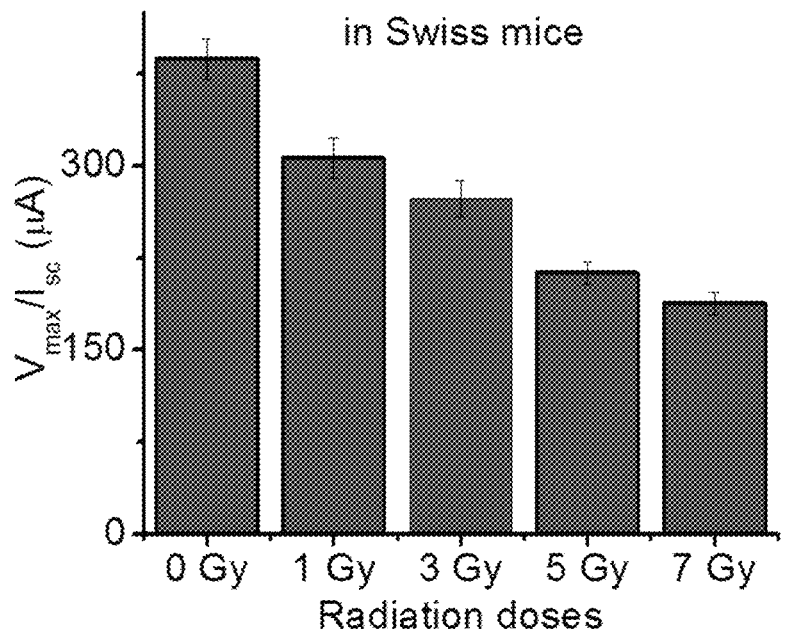
FIG. 10 shows that $V_{max}$ decreased as irradiation doses increased. The minimal decrease in $V_{max}$ was observed at 7 Gy. This indicates that irradiation causes a reduction of functional SGLT-1 for glucose transport.
Figure 11:
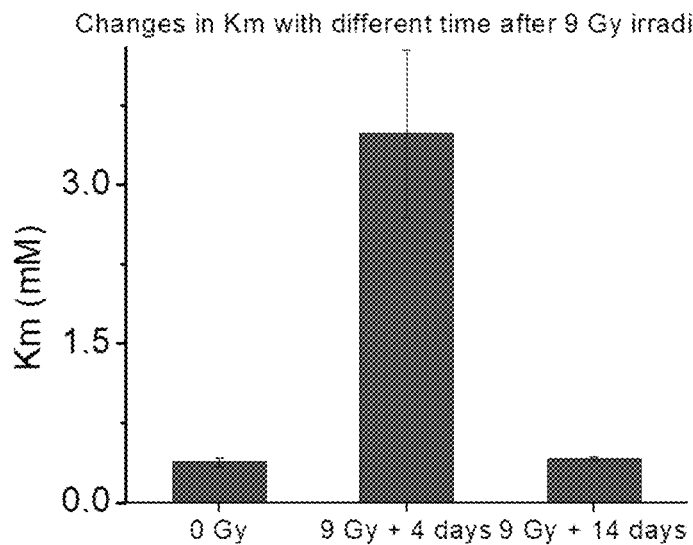
FIG. 11 shows changes in $K_m$ over time post irradiation. $K_m$ increased immediately after irradiation and returned to normal (control values) approximately 14 days post irradiation.
Figure 12A:
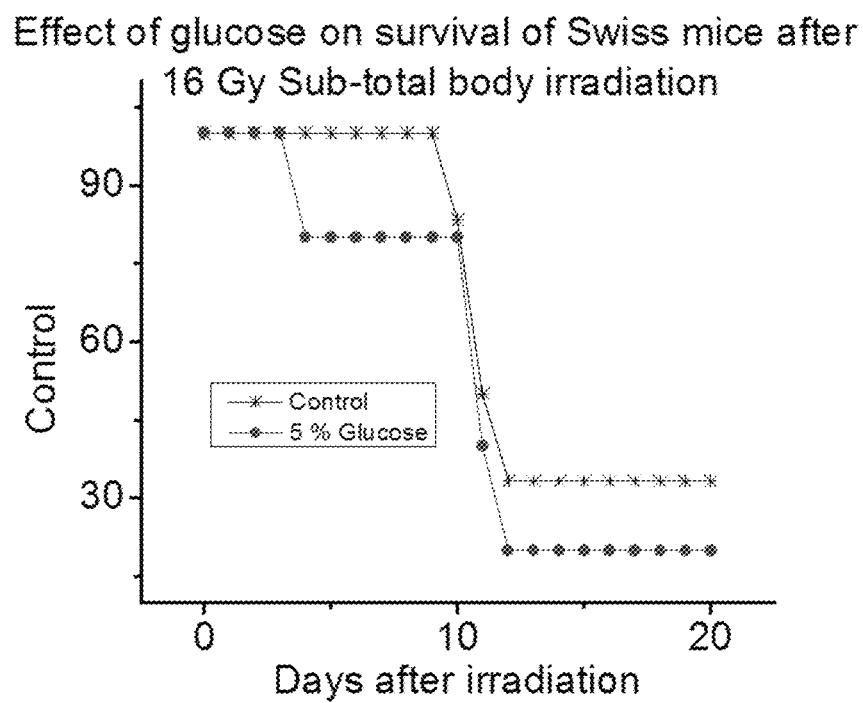
FIGS. 12A-12B show results of murine survival studies after 9-Gy and 15.6-Gy irradiation. Death of glucose-treated mice occur starting on days 5 and 7, while control mice did not die until 10 days after irradiation. On day 20, 30% of the control mice were alive, whereas none of the glucose-treated mice survived on day 20.
Figure 12B:
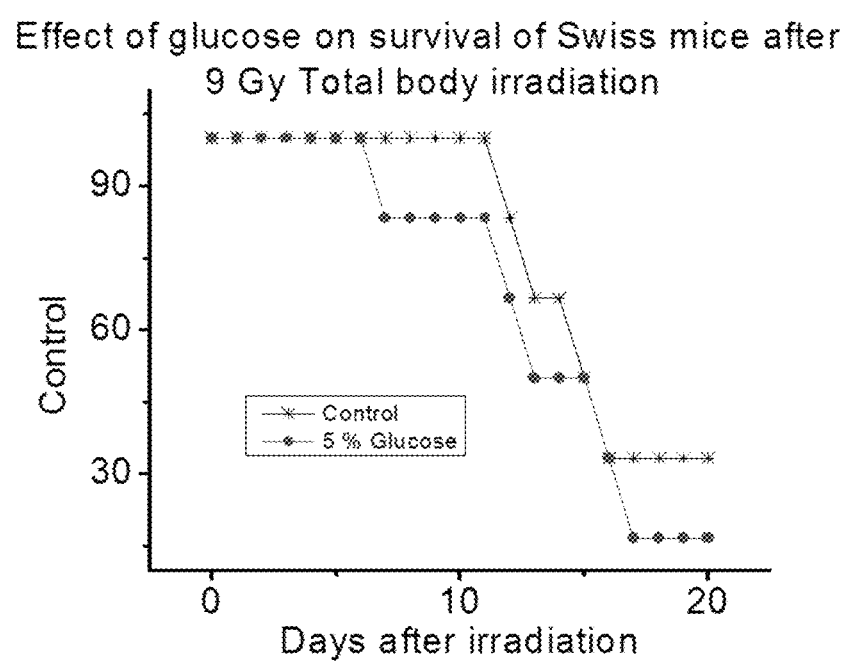
Figure 13:
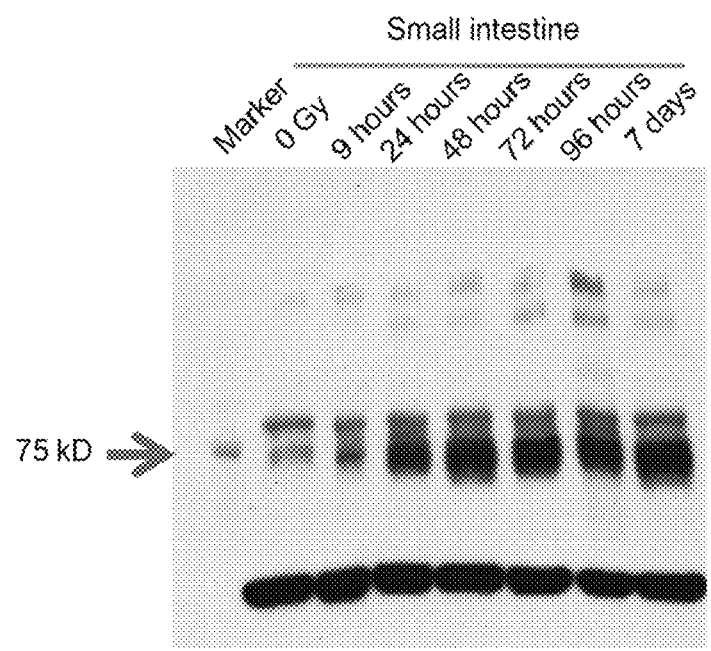
FIG. 13 shows Western blot analysis of SGLT-1 protein levels in whole-cell lysates. The results showed that irradiation increased SGLT-1 expression.
Figure 14:
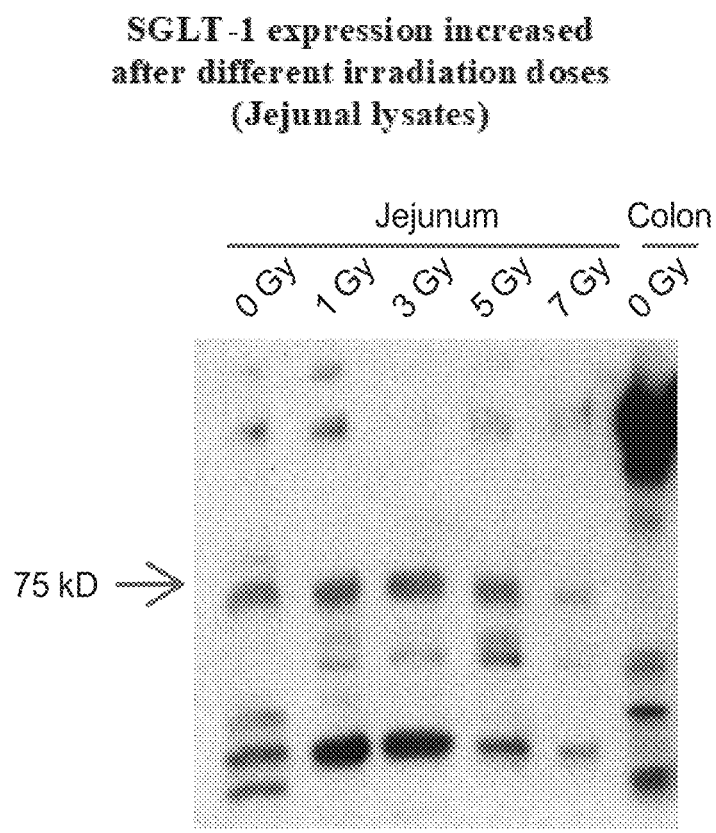
FIG. 14 shows Western blot analysis of SGLT-1 protein levels in brush-border membrane vesicles of jejunum tissues. Irradiation increased SGLT-1 protein levels in a dose-dependent manner. No SGLT-1 protein was detected in colonic tissues.

This Example shows that in IR-induced enteritis, there is a dose-dependent decrease in glucose absorption. In addition, the presence of unabsorbed glucose in the gut lumen can lead to osmotic diarrhea, further deteriorating the diarrheal conditions associated with IR. FIG. 7A shows that irradiation causes a dose-dependent decrease in I$_{sc}$. FIG. 7B shows that irradiation increases K$_m$ in glucose transport in a dose-dependent manner.

SGLT1 is a versatile transporter. SGLT1 maintains its function in infective diarrhea, such as cholera. The preservation of SGLT1 function in infective diarrhea has been used in oral rehydration therapy for Na$^+$ absorption.

To investigate SGLT-1 function and its effect on glucose absorption following irradiation, small intestine mucosa of Swiss mice was obtained on day 6 after IR exposure at 0, 1, 3, 5, or 7 Gy. Glucose-stimulated short-circuit current (I$_{sc}$) was measured in an Ussing chamber to study the SGLT1 transport function. Survival studies were carried out in 9-Gy TBI and 15.6-sub-TBI mice.

Specifically, 8-week-old Balb/c mice obtained from the National Institutes of Health (NIH) were subject to 137Cs sub-total body irradiation (Sub-TBI) (one leg was protected from irradiation) and total-body irradiation (TBI).

In animal survival studies, mice were separated into 2 groups: 9-Gy TBI and 15.6-Gy Sub-TBI. Control mice were treated with normal saline; others were treated with 5% glucose. Gavage was used during the experiment, and treatments were given on the first 5 days after irradiation and every other day until 10 days after irradiation.

A Multichannel Voltage/Current Clamp (Physiological Instruments, San Diego, Calif.) was employed in the Ussing chamber study. Mice jejunal sections, which were used for the mounting, were bathed in modified-regular Ringer's solution, and gassed with 95% O2 & 5% CO2 to measure short I$_{sc}$. All mice were sacrificed 6 days after irradiation. To investigate SGLT-1 kinetics, the substrate (glucose) concentration started at 0.05 mM and ended at 10 mM. Glucose was added at a rate starting from 0.05 mM and progressed to 0.1 mM, 0.5 mM, and 1 mM. The results were analyzed with Origin 8 software (OriginLab Corp., Northhampton, Mass.). I$_{sc}$ was plotted into the Y-axis, and glucose concentration was plotted into the X-axis. The curve was fitted into Hill's equation.

To prepare Jejunal whole-cell lysates, mucosal scrapings of normal and irradiated mice were lysed in triacylglycerol hydrolase buffer containing 25-mM HEPES, 10% glycerol, 1% Triton X-100, and a protease inhibitor mixture (10 mM iodoactamide, 1 mM phenylmethylsulphonyl fluoride, and 2 μg ml-1 leupeptin, pH 7.4).

To prepare brush-border membrane vesicle lysates, mucosal scrapings of normal and irradiated mice were homogenized in a 2-mM Tris-HCl (pH 7.1)/50-mM KCl/1M PMSF solution. The samples were spun down with a centrifuge at 8000 RPM and again at 13,000 RPM, respectively, and were then homogenized again with a turberculin syringe (27 G needle) and TEFLON homogenizer. The samples were then centrifuged at 4,000 RPM and again at 15,000 RPM. The sample was resuspended with a protease inhibitor mixture (10 mM iodoactamide, 1 mM phenylmethylsulphonyl fluoride, and 2 μg ml-1 leupeptin, pH 7.4) that contained regular Ringer's solution.

Both protein concentrations of jejunal whole-cell lysates and brush-border membrane vesicles were analyzed for SGLT-1 protein by Western blots. Equivalent loads of protein from irradiated and control samples were analyzed by sodium dodecyl sulfate polyacrylamide gel electrophoresis (SDS-PAGE). Proteins were transferred onto polyvinylidene fluoride (PVDF) membranes, and SGLT-1 proteins were detected using affinity-purified polyclonal antibodies.

The results, as shown in FIGS. 8-14, demonstrate that: 1) irradiation reduces glucose-stimulated $I_{sc}$ in a dose-dependent manner; 2) $K_m$ values for glucose were (mM) 0.38±0.04, 0.49±0.06, 1.76±0.16, 1.91±0.3, 2.32±0.4 in 0, 1, 3, 5, and 7 Gy, respectively; 3) $V_{max}$ values for glucose were 387.4±16.2, 306.6±16.4, 273.2±14.9, 212.9±9.14, 188.1±9.12 in 0, 1, 3, 5, and 7 Gy, respectively; 4) $K_m$ and $V_{max}$ values returned to normal levels approximately 14 days after IR; 5) withholding glucose intake for the first 10 days after irradiation increased survival; 6) Western blot analysis of the SGLT-1 brush-border membrane showed increased SGLT-1 protein levels as IR doses increased.

The increase in SGLT-1 $K_m$ indicates a decrease in SGLT-1 affinity for glucose due to irradiation. The decrease in $V_{max}$ indicates the loss of villous epithelial cells due to irradiation, as is also evidenced by the histopathological examinations. The increase in protein levels in mice tissues treated with IR, as shown in Western blot analysis, indicates that SGLT1 transporters are expressed but non-functional.

The results also demonstrate oral glucose feeding results in malabsorption of glucose and electrolytes, which leads to osmotic diarrhea and, thus, increases IR-induced GI toxicity. In contrast, withholding glucose from oral feeding for first 14 days after IR prevents or mitigates symptoms of diarrhea and increases overall survival.

Example 9

Irradiation Causes Reduced Glutamine Transport

Although glutamine is a non-essential amino acid, it is the primary nutrient of the enterocytes, and is present in high concentrations in plasma (26%) and in skeletal muscle (75%). Glutamine levels decrease in post-operative, trauma, or critical patients as the body's demand for glutamine increases. Thus, glutamine has been considered as important in the normal functioning of the digestive, renal, immune and neuronal systems.

Figure 15:
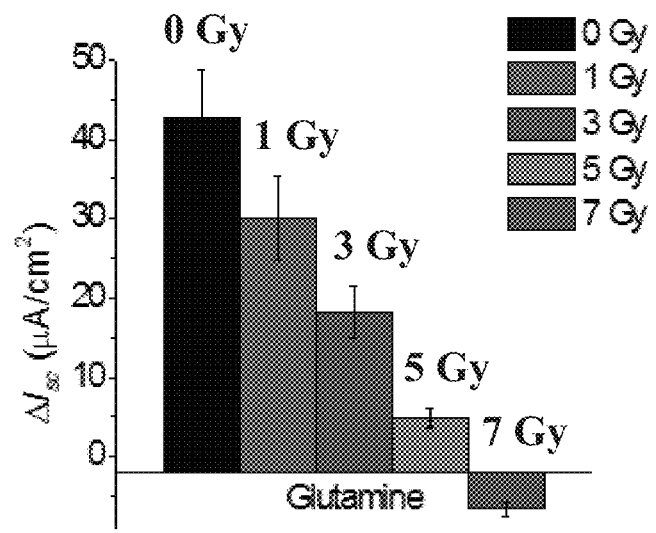
FIG. 15 shows that irradiation caused a dose-dependent increase in glutamine-stimulated $I_{sc}$.

This Example shows that irradiation causes a dose-dependent decrease in glutamine transport into the cells. At IR≥7 Gy, glutamine becomes largely present in the gut lumen, thereby leading to osmotic diarrhea. Saturation kinetics of glutamine transporter showed an IR dose-dependent increase in $K_m$ (FIG. 15), suggesting decreased affinity of glutamine transporters for glutamine.

Example 10

Irradiation Causes a Dose-Dependent Increase in Lysine Transport

Figure 16:
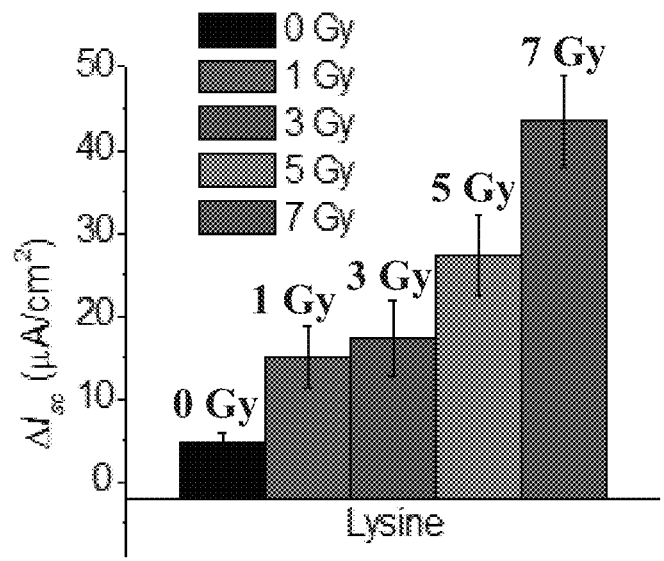
FIG. 16 shows that irradiation caused a dose-dependent decrease in lysine-stimulated $I_{sc}$.

Addition of lysine to the small intestine lumen side causes an increase in $L_{sc}$, suggesting electrogenic transport of lysine (FIG. 16). Tissues from non-IR mice showed a $K_m$ of 1.16±0.04 mM, while 3 Gy IR tissues had a $K_m$ of 0.27±0.01 mM. Unlike glucose and glutamine, the results showed that irradiation increased lysine-transporter affinity for lysine and, thus, increased lysine absorption.

Example 11

Effect of Oral Lysine Feeding on Survival of Mice

This Example shows that withholding non-absorbed nutrients from oral feeding while selectively feeding absorbed nutrients prevents or mitigates diarrhea and increases survival after irradiation.

Figure 17A:
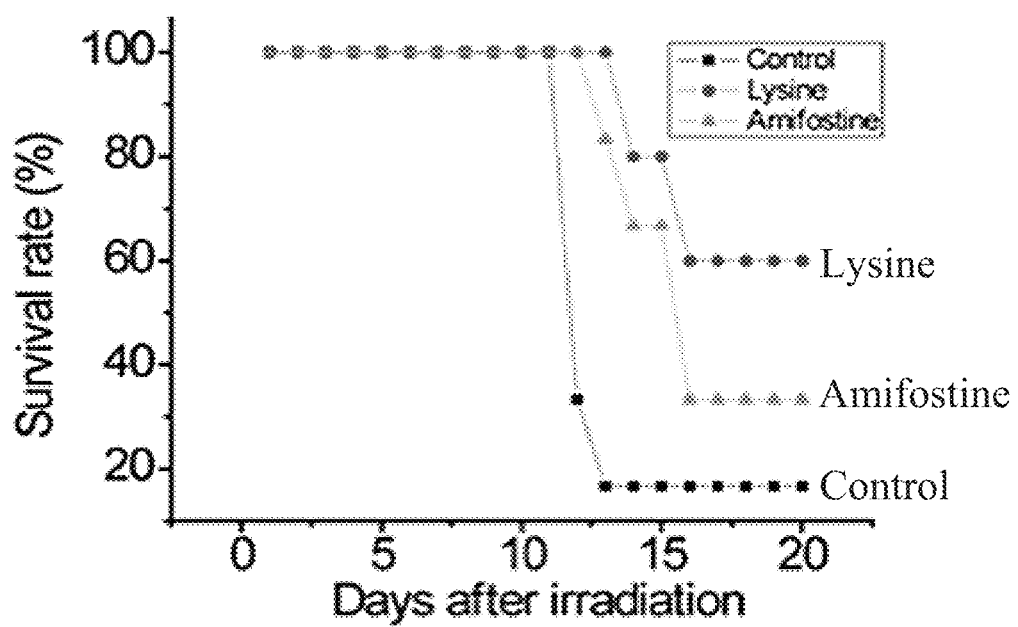
FIGS. 17A-17B show mice survival rate following lysine (17A) or glucose (17B) therapy after IR. Lysine administration resulted in increased survival, whereas glucose administration resulted in decreased survival.
Figure 17B:
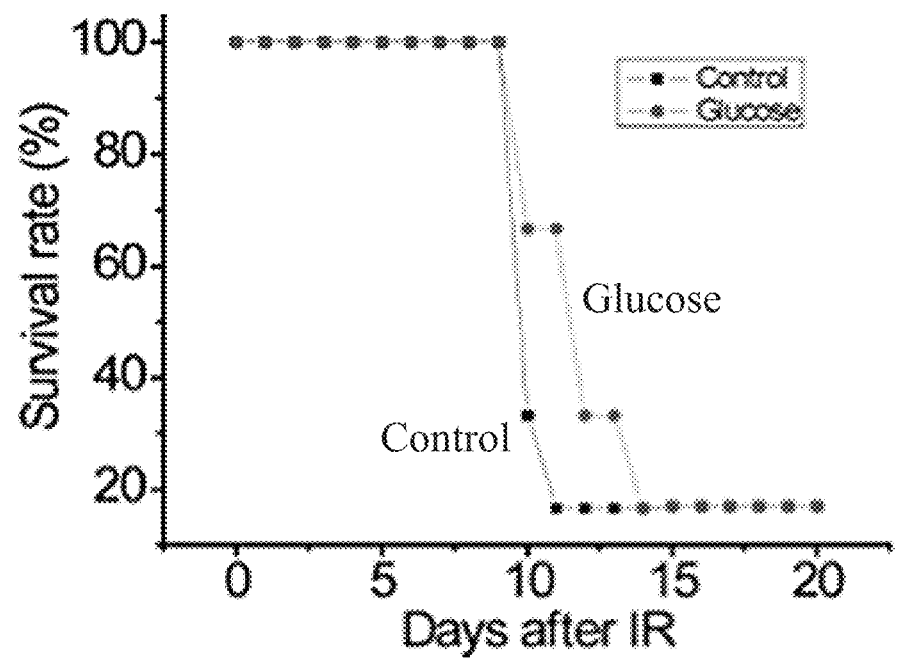

In the first series of experiments, glucose (10 mM i/m for 5 days and then every alternate day) was orally administered to IR mice. The results show that glucose administration decreased overall survival (FIG. 17B). In comparison, lysine (20 mg/mice/day) was orally administered to IR mice for 5 days and thereafter every other day as gastric lavage. Mice treated with lysine showed increased survival when compared to control groups (FIG. 17A). Thus, reducing or limiting oral intake of non-absorbed nutrients such as glucose with increased oral intake of absorbed nutrients such as lysine can prolong survival in irradiated patients.

Example 12

Changes in Ion Transport Protein Expression Levels Due to Irradiation

Figure 18A:
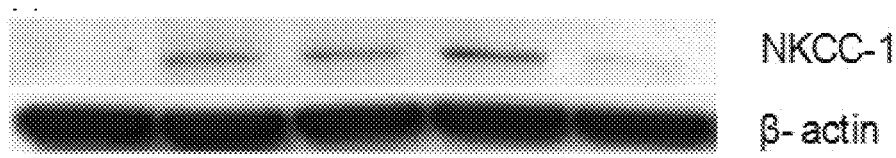
FIGS. 18A-18D show Western blot analyses for various transport proteins. Western blot analysis showing NKCC1 (18A), CFTR (18C) and NBCe1-A/B (18B) protein levels in jejunum of mice. From left to right, the lanes represent 0, 1, 3, 5 and 7 Gy. Irradiation increased NKCC1 protein levels from 1-5 Gy and such increase decreased at 7 Gy (18A). NBCe1-A/B protein levels significantly decreased following irradiation. CFTR (18C) protein levels in jejunum tissues significantly increased following irradiation at 3 Gy as compared to 0 Gy. Jejunum had the highest NBCe1-A/B protein levels compared to that in duodenum, ileum or colon (18D). Tissues were harvested for western blot on day 6 post-irradiation.
Figure 18B:
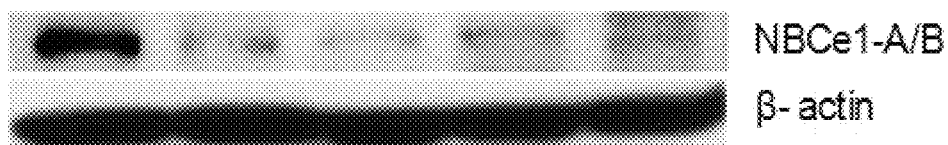
Figures 18C, 18D:
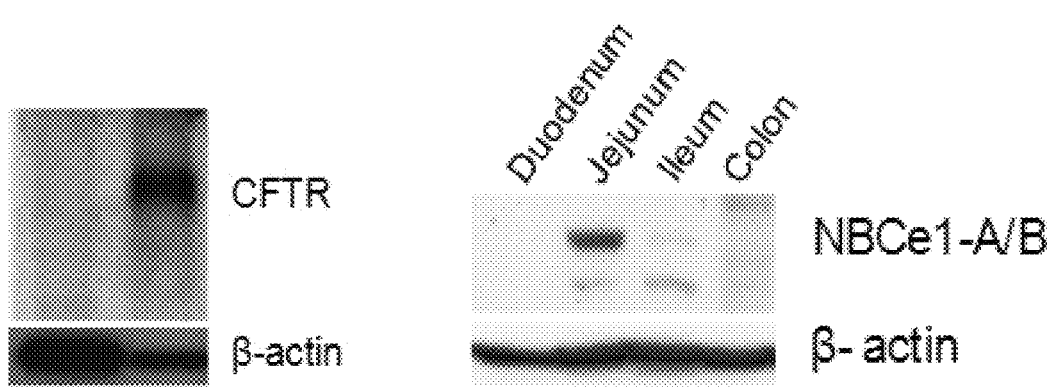

This Example illustrates changes in transport protein expression levels due to irradiation. Specifically, tissues were harvested for Western blot on day 6 post-irradiation. Western blot of ileal tissues, as shown in FIG. 18, revealed that irradiation from 1-5 Gy resulted in increased NKCC1 protein levels; while such increase in NKCC1 expression decreased in tissues received 7 Gy IR, as compared to tissues received 1-5 Gy IR (A).

NBCe1-A/B protein levels significantly decreased following irradiation, even at a dose as low as 1 Gy (B). CFTR protein levels in jejunum tissues significantly increased following 3 Gy irradiation, as compared to 0 Gy jejunum tissues (C). NBCe1-A/B specific antibodies showed increased expression levels in the jejunum compared to the duodenum, ileum, and colon in non-irradiated mice (D). Jejunum tissues had the highest NBCe1-A/B protein levels, as compared to that in duodenum, ileum or colon (D). The changes in levels of transport protein correspond to the observed functional changes following IR. The expression pattern of the transport proteins post-irradiation, as compared to that of non-IR tissues, can be used to monitor the effectiveness of the oral radiation diet.

Example 13

Changes in Nutrient and Electrolyte Absorptive Capacity in Mice with Injury to Small Intestine Mucosa A similar pattern of alterations in small intestine absorptive capacity is observed in C57BL/6 mice treated with radiation, chemotherapy, and suffering from inflammation in the small intestine. The radiation model is constructed as described in Examples 1-12.

In a chemotherapy model, all mice are injected with a single dose of 5-FU or cisplatin. In some mice, three days after the first injection, a second dose of 5-FU or cisplatin is injected. Following each injection, transepithelial Isc, an indicator of net anion secretion, is measured using an Ussing chamber, at time points as indicated in FIG. 20. For each measurement, a minimum of 32 tissues is examined.

Figure 20A:
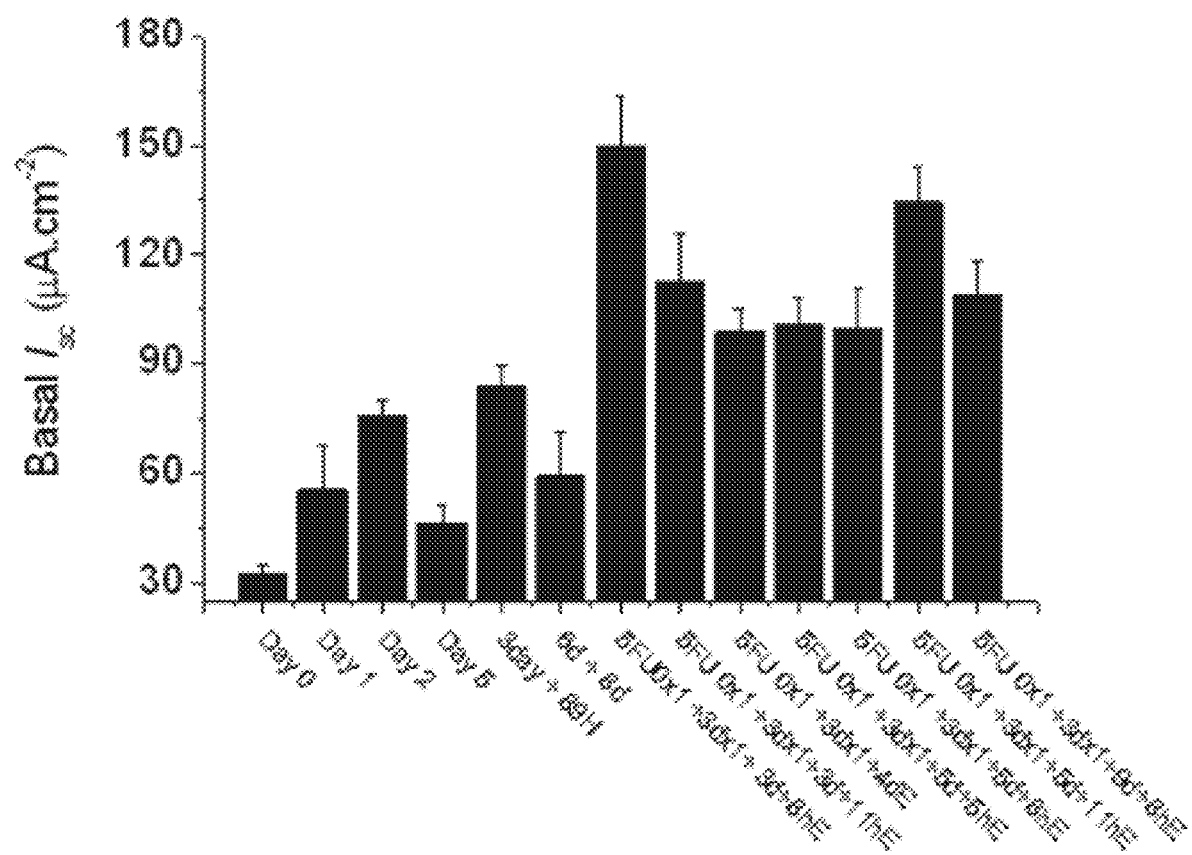
FIGS. 20A-20B show injury to small intestine mucosa in mice treated with 5-fluorouracil (5-FU) (20A) and cisplatin (20B). (20A) shows change in Isc in 5-FU-injected mice. (20B) shows change in Isc in cisplatin-injected mice.
Figure 20B:
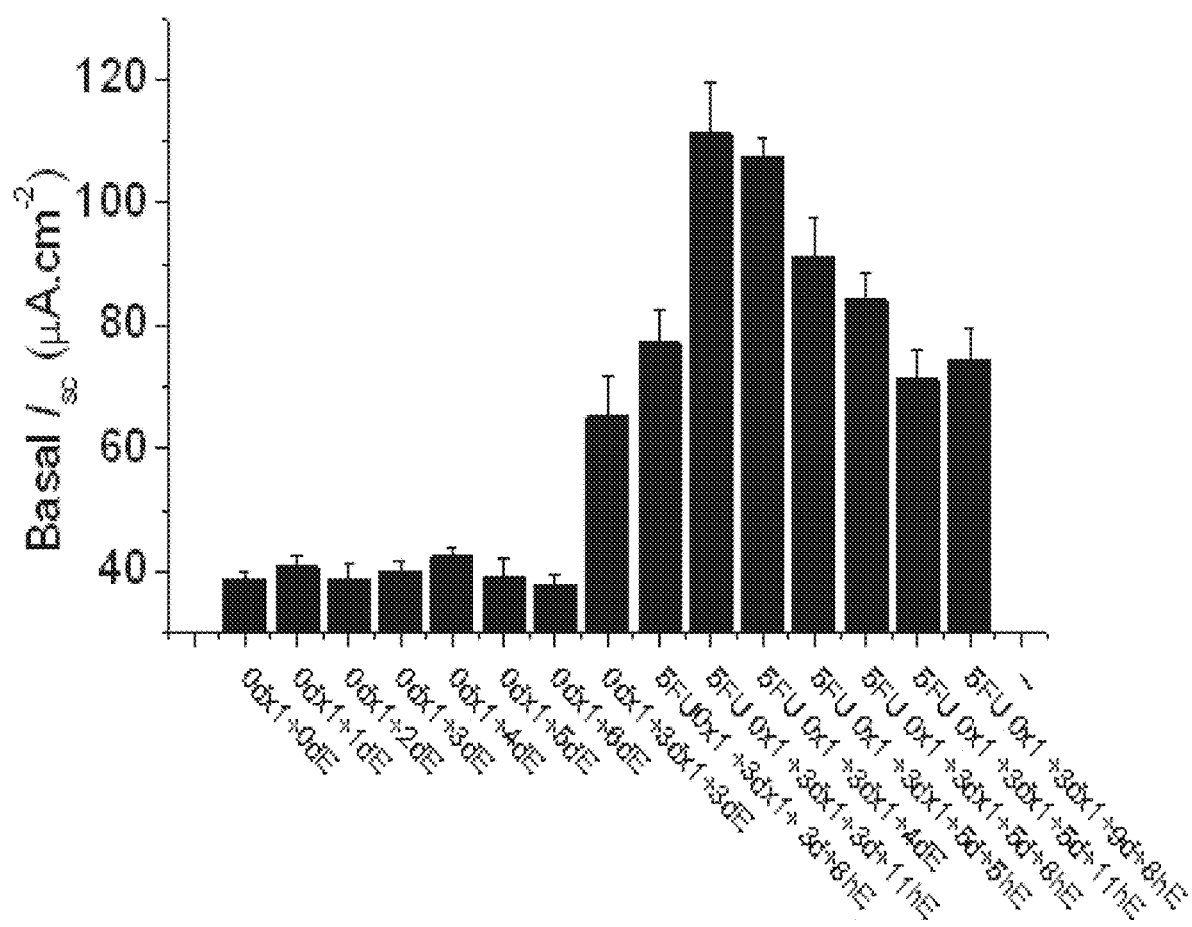

The results show that there is a significant increase in net anion secretion on day 3 in mice injected with a single dose of cisplatin (FIG. 20B) or 5-FU (FIG. 20A). Also, mice injected with a second dose of the chemotherapeutic agent exhibit a significantly higher increase in net anion secretion than that of mice receiving a single dose.

In a Crohn's disease model, mice are injected with anti-CD3 mAb (acute inflammatory model to mimic conditions of Crohn's disease). There is also a significant increase in net anion secretion (determined based on paracellular conductance) and paracellular permeability of the small intestine. Also, alterations in nutrient and electrolyte absorptive capacity are observed.

The alterations of absorptive capacity of nutrients are determined using disease models with injury to small intestine mucosa, i.e., the radiation model, chemotherapy model, and the Crohn's disease model. Specifically, a candidate nutrient is orally administered to control mice and mice that received irradiation, chemotherapy, and anti-CD3 mAb, respectively. In addition, compositions containing various combinations of the candidate nutrients are orally administered.

The candidate nutrients are selected from lysine, histidine, valine, leucine, phenylalanine, cysteine, tyrosine, arginine, isoleucine, threonine, glycine, alanine, methionine, tryptophan, proline, serine, asparagine, glutamine, aspartic acid, glutamic acid, and glucose.

To determine the absorptive capacity of each nutrient, bioelectric measurements are performed using an Ussing chamber. The measurements include: a) the sodium coupled-amino acid current (Isc) and changes in conductance, b) changes in saturation kinetics of each nutrient and changes in the Isc following the administration of each nutrient; and c) the electrolyte absorption studies using isotope flux studies in the presence and absence of the specific candidate nutrient. The results show that, in the radiation model, chemotherapy model, and the Crohn's disease model, there is a similar pattern of alterations in absorptive capacity for all amino acids investigated and glucose. Specifically, the results show that the oral administration of each of the following amino acids selected from lysine, glycine, threonine, valine, tyrosine, aspartic acid, isoleucine, tryptophan, asparagine, and serine improve small intestine healing, reduces paracellular conductance (thereby improving small intestine mucosal barrier mechanism), increases absorption of electrolytes, and/or improves survival in animals. The results also show that the oral administration of glucose and/or glutamine impairs small intestine mucosa barrier, and has adverse effects on survival of mice in the radiation model, chemotherapy model, and the Crohn's disease model.

Example 14

Improvement of Small Intestine Function in Mice that have Received Chemotherapy

This Example shows that the therapeutic composition of the subject invention improves small intestine healing of mice that have received chemotherapy. Of all chemotherapy drugs studied, 5-FU shows maximum toxicity to small intestine. Therefore, 5-FU is used to characterize the alterations of electrolyte and nutrient transport in the chemotherapy model.

NIH Swiss mice were injected with 5-FU. Five or six days after injection, The intestinal tissues from the mice were isolated and studied in an Ussing chamber, exposing to either Ringer solutions or the therapeutic composition of the subject invention. The therapeutic composition contains lysine, glycine, threonine, valine, tyrosine, aspartic acid, isoleucine, tryptophan, asparagine, and serine; water; and therapeutically acceptable carriers, electrolytes, and buffering agents. The therapeutic composition is slightly alkaline (pH 7.4). The therapeutic composition does not contain glucose, glutamine, or methionine.

Figure 21A:
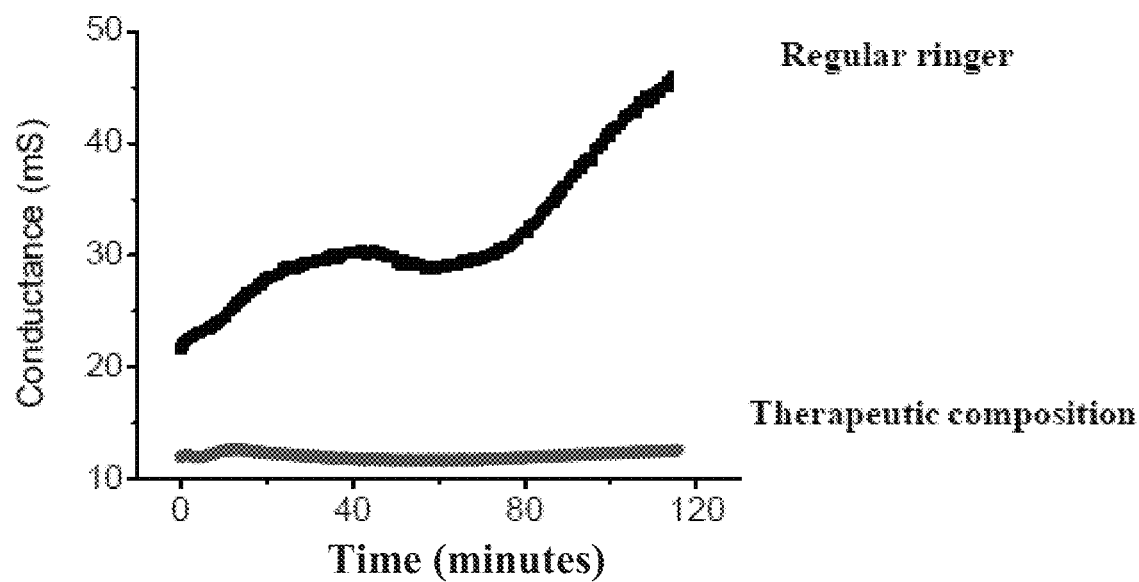
FIGS. 21A-21B show that the administration of with the therapeutic composition of the subject invention improves small intestine function of mice that have received 5-FU.
Figure 21B:
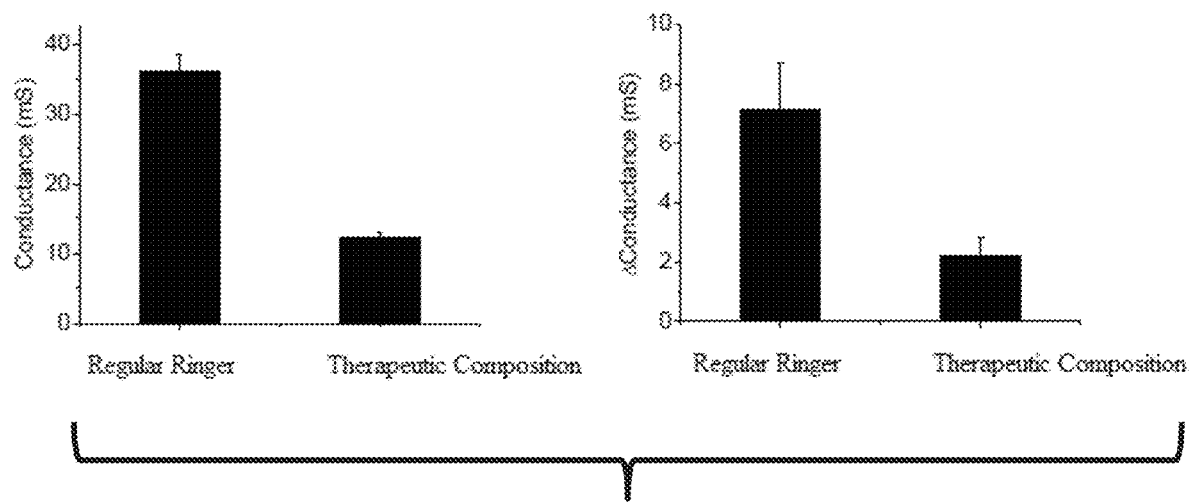

The results show that the therapeutic composition significantly improves small intestine function of mice that have received 5-FU. Specifically, the therapeutic composition significantly reduces the pathological increase in transepithelial $I_{sc}$ (FIG. 21A) and transepithelial conductance in the small intestine of the 5-FU injected mice.

Example 15

Determination of Changes in GI Function Due to Irradiation

The major GI function includes absorption of nutrients, electrolytes and water, and such absorption occurs in well-differentiated and mature villous epithelial cells. 80% of the fluid and electrolyte absorption occurs in the small intestine. As illustrated herein, IR results in selective loss of villous and/or crypt depending on the IR dose, and thereby leads to decreased absorption of $Na^+$, $Cl^-$ and nutrients. This Example illustrates experimental designs for determining alterations in GI function caused by various dosages over time IR.

Methods

C57BL/6 mice (8 weeks old, male) from NCI are used. Physical observations, cytology, immunohistochemistry, Western analysis, plasma surrogate markers, and functional studies are determined as specific indices for IR-induced GI toxicity. Mice were randomly divided into groups and the abdomen irradiated with a Shepherd Mark-I using a Cs source delivering IR at 1.84 Gy/min dose rate to the abdomen. Mice are subject to IR at 0, 1, 3, 5, 7 and 9 Gy. Changes in glucose and amino acid transport are examined on day 0, 1, 2, 4, 6, 8, 10, 12, 14, 16, 18, 20, 25 and 30 with 10 mice in each group. Plasma samples are collected before harvesting the tissue. Ileum and jejunum tissues are harvested for histopathology, Western blot, immunohistochemistry and Ussing chamber studies (subjected to separate evaluation).

A) Determination of Functional Alterations in Electrolytes ($Na^+$, $Cl^-$ & $HCO_3^-$)

This Example illustrates experimental designs for determining the alteration in transport protein function associated with electrolyte absorption following IR. The alterations in electrolyte transport function are then correlated to plasma markers, cytology, and physical observations such as daily activity, body weight, stool formation and fecal occult blood. Cytology examinations are performed using crypt assay, H&E staining, BrdU staining, immunohistochemistry and Western blot analysis.

First, transepithelial flux of $Na^+$ and $Cl^-$ is examined in an Ussing chamber to evaluate electrolyte absorption after IR. Mice are sacrificed, and the changes in the basal ion transport in the non-IR mice and mice treated with IR at various doses are examined. Na$^+$ and Cl$^-$ absorption is electroneutral in regular epithelium.

In this Example, isotope ($^{22}$Na and $^{36}$Cl) substitution studies are performed to determine the basal Na$^-$ and Cl$^-$ movement. Briefly, $^{22}$Na and $^{36}$Cl are added either to the mucosal or to the serosal side. 0.5 ml samples are collected from the cold side at the end of every 30 minutes. Unidirectional fluxes are calculated using standard formula, and expressed as $\mu mol \cdot h^{-1} \cdot cm^{-2}$. Net flux ($J_{Net}$) is calculated as the difference between $J_{ms}$ and $J_{sm}$ fluxes across tissue pairs. Experiments are performed under short-circuit conditions.

In addition, pH stat techniques are used to measure changes in HCO$_3^-$ secretion. As illustrated herein, IR decreased HCO$_3^-$ secretion in jejunum. HCO$_3^-$ secretion is critical for acid base balance and acid neutralization in the upper segments of gut[72-74]. These experiments suggest the possible mechanism of HCO$_3^-$ secretion and indicate 1) lumen Cl-dependent HCO$_3^-$ secretion and 2) lumen Cl$^-$-independent HCO$_3^-$ secretion in normal mice and in irradiated mice. Bicarbonate secretion is expressed as follows:

$$\text{Total bicarbonate secretion } (\mu eq/h/cm^2) = \frac{(D2 - D1) \times 0.025 \times 2 \times 60}{1.13 \times (t)}$$

where D2 and D1 are the difference between the total acid added between two time points, 0.025 represents the normality of the acid added, 2 the valency of H$_2$SO$_4$ and 60 represents the time in minutes to finally express secretion per hour. 1.13 represents the surface area of the tissue used in the Ussing chamber and t time. HCO$_3^-$ secretion studied using pH stat technique will complement transepithelial Na$^+$ and Cl$^-$ flux measurements.

Ion flux experiments, pH stat studies, and trans-epithelial electrical measurements can elucidate the transport process in the non-IR and IR mice.

B) Determination of Functional Alterations in Nutrient Absorption Due to Irradiation Intestinal malabsorption of nutrients affects nutritional status following IR. As illustrated herein, selective absorption of nutrients occurs following IR. The presence of unabsorbed nutrients in the gut leads to osmotic diarrhea, which further complicates injury caused by irradiation. This Example illustrates the experimental design for determining the nutrients that are absorbed from the intestine after IR.

Easily-absorbed nutrients can be included into the therapeutic/dietary composition of the subject invention to examine the effect of various IR doses on glucose absorption over time.

Specifically, changes in glucose transport are determined in Ussing chambers following IR. The time required for glucose transport proteins to return to their normal function (non-IR levels) is also investigated. The formulation (ORD) is derived according to the ability of the mice to tolerate oral glucose. Glucose is withheld from the oral supportive regimen until glucose transport begins to improve.

In addition, changes in amino acid (a.a) transport following IR are examined. Electrogenic amino acid transport can be detected in an Ussing chamber as the net charge movement that occurs when the amino acid is transported. There is no charge movement associated with electroneutral a.a and, therefore, these transports are studied in brush border membrane vesicle studies (BBMV). Both electrogenic and electroneutral a.a are studied in BBMV for comparison between different experimental methods.

Specifically, the four major types of amino acid transport system are studied by testing the uptake of representative amino acids L-leucine (neutral amino acid), L-proline (IMINO acid), L-glutamic acid (acidic amino acid), and L-cysteine (sulfurate amino acid) in brush-border membrane vesicles (BBMV) from non-IR and IR mice.

Changes in Electrogenic a.a Transport Due to IR

Amino acids are broadly classified into neutral, cationic and anionic as their transport characteristics are largely based on charge (Table 4). Electrogenic a.a transport can occur via B$^{0/+}$ (neutral and cationic a.a) or X$^-_{AG}$. Na-coupled and Na-independent a.a transport are determined by experiments in the presence and absence of lumen Na$^+$. In addition, electroneutral a.a transport is studied in BBMV using $^{14}$C labeled amino acids.

TABLE 4

Amino acid transport system in the brush-border membrane of the small intestine

| Transport system | Molecular identfty | Alternate identity | Substrates | Dependence on Na | Involvement of other ions |
|---|---|---|---|---|---|
| B$^0$ | B$^0$AT1 | SLC6A19 | Neutral a.a | Yes | No |
| B$^{0/+}$ | AT1B$^{0/+}$ | SLC6A14 | Neutral a.a, cationic a.a | Yes | Cl$^-$ |
| b$^{0/+}$ | b$^{0/+}$AT | SLC7A9 | Neutral a.a, cationic a.a, cystine | No | No |
|  | rBAT | SLC3A1 | No transport function of its own, it influences the kinetic parameters of the transport function of b$^{0/+}$ AT |  |  |
| PAT | PAT1 | SLC26A6 | Neutral short chain a.a (glycine, alanine and proline) | No | H$^+$ |
| X$^-_{AG}$ | EAAT3 | SLC1A1 | Anionic a.a (aspartate, glutamate) | Yes | K$^+$, H$^+$ |

Preparation of BBMV to Study a.a Transport and Western Blot

BBMVs are isolated using the magnesium precipitation method[75]. The total protein content of BBMVs is determined using the Bradford method[76]. Vesicles are stored in liquid N$_2$ or at −80° C.

Assessment of Amino Acid Uptake by BBMVs

Amino acid uptake by BBMVs is performed at 25° C. using the rapid filtration technique described by Hopfer et al.[75] with slight modifications. BBMV suspensions (5 μl) are added to the incubation medium (45 μl) containing 1 mmol/l of unlabeled amino acid, 25 μCi/ml of radiolabeled substrate L-[U-$^{14}$C]leucine, L-[U-$^{14}$C]proline, L-[U-$^{14}$C]glutamic acid, or L-[$^{35}$S]cysteine, 100 mmol/l NaSCN or KSCN, 100 mmol/l mannitol, 0.1 mmol/l MgSO$_4$ and 10 mmol/l HEPES (pH 7.4). The time courses of the uptake of amino acids are measured in the presence of Na$^+$ gradient (using medium containing NaSCN) and in the absence of Na$^+$ gradient (medium containing KSCN). At specific time intervals, the uptake process is ended by adding 5 ml of ice-cold stop solution containing 150 mmol/l KSCN and 10 mmol/l Tris-HEPES (pH 7.4). The suspension is immediately poured onto a pre-wetted Millipore filter that is washed three times with 3 ml of ice-cold stop solution and immersed in 5 ml of scintillator Hisafe 3 fluid (LKB Products, Bromma, Sweden). The filter is then counted in a Liquid Scintillation Counter. Nonspecific binding to the filter is previously measured and subtracted from the total uptake. Results are expressed as picomoles of amino acid uptake per milligram ofprotein.

C) Determination of Changes in Paracellular Permeability Due to IR

Alterations in paracellular permeability are determined using the following techniques. i) Dilution potential; ii) TEER; iii) permeation of large non ionic solutes of different sizes; FITC-conjugated dextran and Rhodamine B isothionateDextran.

Changes in Dilution Potential with Mitigation Following IR

Dilution potential measurements are used for determining the changes in the permeability ratio between the Na$^+$ and Cl$^-$ using the Nernst equation. The results from these experiments are compared between non-IR and IR mice groups. The results from paracellular permeability and plasma endotoxin studies are correlated with the electrophysiology data and survival data.

Dilution potentials are induced by mucosal perfusion with Ringer solutions containing various concentrations of Na$^+$ and total osmolarity is adjusted with mannitol to maintain equal osmolarity between experiments. The contribution of other ions to the conductance is estimated to be less than 5% and therefore is neglected. The potential difference across the membrane is measured using AgCl-AgCl electrodes and a multimeter (VCC MC8, Physiologic instruments Inc.). Dilution potentials are corrected for changes in junction potential (usually less than 1 mV). These experiments permit calculation of chloride and sodium conductance of the paracellular pathway using the following formula.

$$Em = RT/F * 2.303 \log 10\{Pna[Na]_o + PCl[Cl]/Pna[Na]_L + PCl[Cl]_o\}$$

R=8.314472 (J/K/mol); F=96.48531(KJ/mol); Permeability ration (β)=PCl/PNa; T=310(Kelvin)

Changes in Non-Ionic Solute Permeation Through Paracellular Spaces Following IR

Paracellular permeability to water-soluble, uncharged solutes of various sizes is studied in small intestine tissues mounted in an Ussing chamber using FITC-conjugated dextran and Rhodamine B isothionateDextran (Sigma). These studies allow for the determination of paracellular permeability changes due to IR.

Intercellular barrier formed by tight junctions is highly regulated and is size and ion-selective. Therefore, this intercellular barrier represents a semi-permeable diffusion barrier. Experiments are designed to determine the paracellular permeability to water-soluble, uncharged solutes of various sizes in ileal or jejunal tissues mounted in Ussing chamber under basal conditions in both regular epithelium and epithelium exposed to radiation.

FITC-conjugated dextran and Rhodamine B isothionateDextran (Sigma) at a concentration of 3mg/ml dissolved in Ringer solution is added to the mucosal side of the Ussing chamber and maintained at 37° C. for 60 min. The solution in the basolateral bath solution is sampled to quantify fluorescently labeled dextran. FITC-Dextran: Exc 485 nm and Em: 544 nm and Rhodamine B isothionateDextran: Exc 520 nm and Em 590 nm. Standard curves are obtained from mice ileal or jejunal tissue mounted in Ussing chamber to check for any change in permeability with time. These values are then compared with tissues from IR- and non-IR mice.

D) Determination of Irradiation Effects

Tissues from mice sacrificed for an Ussing chamber and pH stat studies are used for H&E staining, BrdU, stool formation, occult blood, body weight, immunohistochemistry and Western analysis. These results are then compared to functional alterations in electrolyte, nutrient and paracellular permeability changes in non-IR and IR mice.

Pathological Analysis by Crypt Assay, H&E, BrdU Staining a) Crypt Assay/Microcolony Survival Assay Objective curves were fitted to the data, using a model for cell killing, which assumes that clonogenic ('structure-rescuing') cells in a multicellular structure behave in accordance with Poisson statistics. It is assumed that the structure remains intact until, on average, fewer than three cells survive per structure; that survival of cells is exponential over the range of doses being analyzed; and that the structure may regrow from one or more surviving cells. Each epithelial focus is thought to represent survival of one or more clonogenic stem cell able to give rise to the regenerative crypt.

Mice are sacrificed at 3.5 days after IR for crypt microcolony assay. This interval is at or near the peak of mitotic recovery in crypts after IR. It is used to study the acute effects of IR.

For the biological response to radiation, Do and Dio values are calculated. Studies have shown that despite lack of statistically significant differences between the $D_0$ values, the variance about $D_0$ greatly depended on the number of mice and sections per datum point. Decreased values of the coefficient of variance (~5%) could not be obtained by increasing the number of sections above two and the number of mice above four. Thus, the studies were designed with 3 sections per mouse and six mice per datum point.

b) BrdU Staining to Detect Mitotic Activity after IR

The mice are injected with BrdU (30 mg/kg body weight) and animals are sacrificed at hours 12, 24, 48 or 72, when the tissues are also harvested for functional studies. BrdU injections are repeated once every 24 hrs, when BrdU labeling studies continue beyond 24 hrs after their injection. After BrdU labeling, paraffin sections from mouse small intestines are prepared and stained with anti-BrdU antibody (Ab). Cells were scored per entire crypt and villous unit. At least 60 crypts and corresponding villi were analyzed per mouse. BrdU-labeled cells were normalized to total cell number per crypt or villous. The resulting percentage is then plotted against the induction time. These studies allow for the determination of the rate at which crypt progenitor cells transit into the postmitotic villous compartment, a direct correlation to the rate of cell division in the crypt and kinetics of the migrating crypt cells[77].

Changes in Physical Parameters with IR

Body weight, stool formation and fecal occult blood are studied in mice to detect the changes in the nutritional status of the animals with IR. For daily activity and signs of sickness, all of the mice are observed once a day for diarrhea, lack of grooming, ruffled hair, decreased eating and drinking habits, lethargy, etc, and recorded carefully.

Findings from these studies are compared to plasma analysis for surrogate markers, pathological observations, Western blots, immunohistochemistry and functions studies.

Western Blot Analysis for Determining Molecular Alterations of Transport Processes Involved in Electrolyte and Nutrient Transport Changes in activities of the following transport proteins, which are directly or indirectly involved in electrolyte and nutrient absorption, are examined. The transport proteins include CFTR activity (correlating with electrogenic Cl$^-$ secretion), NHE3 activity (correlates with Na$^+$ absorption), NBCe1-A/B activity in the villous (correlates with $HCO_3^-$ secretion), NKCC1 (basolateral uptake to Na$^+$, K$^+$ and Cl$^-$ into the cell), SGLT-1 (glucose absorption), B$^0$, B$^{0/+}$, b$^{0/+}$, PAT (proton-couled electrogenic transport system) and X$^-_{AG}$ (Table 2). These studies are compared to functional data in non-IR, IR and after treating with ORD.

Immunohistochemistry for Detection of Changes in the Expression Pattern of Transport Proteins, Crypt and Villous Cell Markers Frozen sections are made when the animals are sacrificed for functional studies and for immuno-staining using various antibodies that are specific to various transporters (CFTR, NHE3, NKCC, NBCe1-A/B, SGLT, B$^0$, B$^{0/+}$, b$^{0/+}$, PAT1, and X$^-_{AG}$). In addition, cell surface marker expression patterns are examined to provide insights for crypt and villous cell ratio. These studies allow for the determination of alteration in the expression pattern of transporters with IR and ORD treatment.

E) Identification of Surrogate Marker(s) for Radiation Effects

Although there are several studies trying to identify surrogate marker(s) to determine the radiation dose and time since radiation for determining the onset of GI toxicity, these studies have been largely unsuccessful. This Example illustrates experimental designs allowing for the identification of surrogate marker(s) to predict the onset of GI toxicity, which may also prove useful in scenarios where multiple organs are involved.

Specifically, plasma is collected when the animals are sacrificed for functional evaluation (Ussing chambers). After exposure to an IR dose of 0, 1, 3, 5, 7 or 9 Gy, the mice are sacrificed on day 1, 2, 3, 6, or 9. In order to identify surrogate markers, gut peptides, cytokines, and endotoxin are studied.

Plasma Analysis for Endotoxin

Plasma endotoxin levels are measured. Changes in plasma endotoxin levels are correlated to changes in paracellular permeability, plasma gut peptide levels, sickness and survival rate.

Plasma Analysis for Cytokines

Changes in plasma cytokine levels are examined using LUMINEX multiplex bead array technique in IR and non-IR mice.

Plasma Analysis for Gut Peptides

The gut-specific peptides, including insulin, glucagon, secretin, cholecystokinin, citrullin, somatostatin, peptide YY, ghrelin, NPY, and GLP-2, are investigated. All of the gut peptide kits were purchased from Phoenix Pharmaceuticals, Inc. (CA, USA). Experiments are performed according to manufacture's instruction.

Statistical Analysis

Functional difference among the normal and IR tissues are compared. The statistical significance is calculated using the analysis of variance (ANOVA). The data are compared among the assays. The correlation coefficient (R) is analyzed to determine the best functional marker. All statistical analyses are conducted using Version 9.1 of the SAS System for Windows (Copyright© 2002-2003 SAS Institute Inc., Cary, N.C., USA.). If distributional assumptions associated with a particular statistical procedure are violated, appropriate transformations or non-parametric alternatives are used. Receiver Operating Characteristic (ROC) curves are constructed and the areas under the ROC curves (AUCs) are compared among the various functional tests using the non-parametric method of DeLong et al. (1988). The family-wise Type 1 error rate is controlled at 0.05 using Tukey's method for multiple comparisons. The Pearson correlation coefficients with associated p-value and 95% confidence interval are reported.

Example 16

Development of Ideal Oral Regimens for Treatment of Ir-Induced Gastrointestinal Injury This Example illustrates experimental designs for developing oral therapeutic compositions for treatment or amelioration of radiation-induced GI toxicity. It also determines the time when the oral rehydration diet (ORD) should start and how long the composition should be administered after exposure to various doses of IR. The time for which ORD needs to be administered depends on the time needed for the $K_m$ to return to the basal levels.

Methods

C57BL/6 mice (8 weeks old, male) from NCI are used. To determine the affinity of the transporter, saturation kinetics is calculated by using increasing concentration of the respective nutrients. Preliminary studies have shown that some a.a have increased absorption while some showed decreased absorption, with changes in $K_m$ and $V_{max}$ after IR. Increasing concentration of the a.a are added to ileum or jejunum (subjected to separate evaluation) elicit an increase in $I_{sc}$. Plotting known concentration of a.a against $I_{sc}$ allows for the determination of the saturation kinetics. Administering the a.a selectively absorbed after IR via gastric lavage increases mice survival. $K_m$ and $V_{max}$ for the nutrients are determined in mice IR with 0, 1, 3, 5, 7 or 9 Gy on 0, 1, 2, 4, 6, 8, 10, 12, 14, 16, 18, 20, 25 and 30 days with 10 mice in each group.

A) Determination of $K_m$ and $V_{max}$ of Essential Amino Acids and Glucose for Development of Ideal Oral Radiation Diet (ORD)

As illustrated herein, irradiation causes changes in transport kinetics of nutrients, indicating altered affinity to respective transporters. The affinity for the glucose transporter determined using this technique showed significant decrease and took approximately two weeks to return to the base level. The presence of unabsorbed glucose or nutrients in the gut lumen is known to cause diarrhea. $K_m$ and $V_{max}$ for the nutrients are determined in mice exposed to different doses of IR and followed up for a period up to 30 day after IR. These studies are useful for formulating an ORD based on their absorption pattern with time and radiation dose. In addition, the nutrients that show increased absorption after IR may be utilized as alternate sources of energy for the system. The formulation (ORD) will then be used in survival studies.

Changes in $K_m$ and $V_{max}$ for Glucose Transport in Ussing Chambers Following IR Glucose transport is studied. Specifically, $K_m$ and $V_{max}$ for glucose are studied. Increasing concentrations of glucose are added to the lumen side in Ussing chamber experiments and increase in $I_{sc}$ recorded. Glucose is withheld from the oral supportive regimen until glucose transport begins to improve. The formulation is based on the ability of the mice to tolerate oral glucose.

Changes in $K_m$ and $V_{max}$ for Amino Acid (a.a) Transport Following IR

The kinetic pattern of amino acids based on the IR dose and time following IR is studied by determining the $K_m$ and $V_{max}$ for each a.a. Kinetic indices of electrogenic a.a are determined in Ussing chamber setting as described. Briefly, increasing the concentration of the a.a added to the lumen solution results in increasing $I_{sc}$ response, with saturation at particular a.a concentration. $K_m$ and $V_{max}$ are calculated from the saturation curve.

Electroneutral a.a are studied using BBMV. Amino acid uptake by BBMV is performed in the presence of different concentrations of substrate, from 0.025 to 7 mmol/l, at a fixed transport time of 3 s (19). Each assay is performed in triplicate using the pool of BBMV (n=12) from each experimental group. Maximal velocity ($V_{max}$) is expressed as picomoles of substrate per milligram of protein in 3 s, and the transporter affinity constant ($K_m$) is expressed as millimoles per liter.

Optimize the ORD Therapy to Mitigate GI Toxicity and Improve Survival

It is discovered that lysine at a dose range of 20 mg/mice/day can increase survival in mice. To optimize the ORD treatment regimen by selecting a proper administration dose, frequency and interval, the analysis of the effects of ORD on survival at 7 days, stool formation, occult blood and body weight is performed. ORD is initiated as early as 3 hours after a lethal dose of IR (15.6 Gy=1.2×LD50/7 value) at a dose range determined from $K_m$ values of respective a.a or glucose. The concentration of glucose or a.a used for gastric lavage is calculated from $K_m$ based on recommended daily amounts currently in use for glucose and essential amino acids in adult humans. The dose translation from human to mice is based on the $K_m$ factors[78]. Thus, an inverse relationship exists between the $K_m$ and the daily dose for the nutrients. If IR increased the $K_m$ (suggesting decreased affinity for the transporter), then there is a proportionate decrease in daily dose for the respective nutrient. Two additional ORDs are formulated with doses, i.e., 3 times above and below the calculated dose. The best ORD dosage is determined based on the survival studies.

The gastric lavage is repeated once daily for 7 days. The dose frequency and interval of ORD gastric lavage are subject to change according to the results of the survival studies. GI toxicity peaks around day 2-3 after IR and then gradually recovers by 7 days if the ORD is effective. The mice are observed daily up to 7 days after IR to monitor their survival.

All the mice receiving regular diet die or are sacrificed (moribund; defined as a combination of 20% weight loss, failure to groom, reduced activity and decreased inquisitiveness) within 7 days after IR. If the mice receiving ORD treatment are protected from IR-induced lethality, then the survival experiment will be repeated with an additional 10 mice/group with same treatment to ensure the results are reproducible. The survival data will be analyzed by the Fisher's exact test.

The sample size of 10 animals per group ensures sufficiently high power (>80%) to detect survival differences between close to 0% for the vehicle group and 60% or higher for each of the intervention (in a pair-wise comparison carried out at the adjusted alpha level of 0.017≈0.05/3) to ensure an overall alpha level of 5%. In the event that a statistically significant difference is not observed or only partial mitigation is achieved by the ORD treatment, a new cycle of regimen optimization will be undertaken as described earlier to ensure maximal mitigating efficacy against IR-induced lethality. After selection of an optimal dose, whether more frequent (twice daily) ORD gastric lavage is required is evaluated to achieve greater radiation mitigation and more rapid crypt recovery.

Determining the DMF and the Window of Effectiveness of ORD for Post-IR Therapy

Dose modification factor (DMF) is one of the most important parameters to measure the effectiveness of a radiation mitigator, which is defined by $DMF=LD_{50}^T/LD_{50}^C$ where T is ORD treatment group and C denotes the control group on regular diet[51]. To determine the efficacy of ORD treatment in mitigating IR-induced lethality, groups of average 10 C57BL/6 mice (10-20 mice/group varying with IR dose) are treated with vehicle or ORD using the optimal regimen defined by the previous experiments. The vehicle-treated mice are exposed to 11 Gy to 13 Gy IR using 0.5 to 1 Gy increments. The survival of these mice is recorded during a 7-day observation period after IR. Mice are euthanized at the end of the observation period or when they become moribund.

Small intestine and plasma are collected after euthanasia. Blood samples are used for gut peptide analysis, while the small intestine tissue specimens are used for investigating IR-induced intestinal damage. The LDson value is a good indicator of IR-induced GI toxicity. LDson for the vehicle-treated mice is close to 13 Gy, based on previous observation in our laboratory. The ORD treated groups are exposed to IR ranging from 14.5 to 16.5 Gy IR with 0.5 to 1 Gy increments, observed and examined as described above for vehicle-treated mice. If substantial numbers of mice in ORD treatment groups survive even after exposed to 16.5 Gy, higher IR doses are given to mice in a subsequent study. The LDson value is calculated for ORD-treated animals based on their survival curves and then, the DMF for ORD is calculated. ORD-treated mice have a DMF for LDson greater than 1.2.

To determine how soon the ORD treatment should be given after IR, five groups of animals are administered with ORD at 0, 1, 3, 5, 7, 9, 12 and 24 hours post-IR and followed up with scheduled ORD treatment and observed for 7 days, along with a positive control (3 h post-IR treatment) and a negative control (saline vehicle). Survival of the animals is compared based on survival at the 7-day time point.

In this model, a number of logistic-regression models (outcome variable dead/alive at 7 days) and various time trends in the eight groups having administered ORD after IR are considered. Both linear (most likely decreasing survival as treatment delay increases) and non-linear (exponential survival decreases) models are considered.

Comparisons versus 3 h post-IR administration and vehicle are performed in a pair-wise fashion using the Fisher's exact test. There is a pair-wise comparison (different timing groups vs. the 3 h post-IR, ORD group and vs. vehicle) and the individual test alpha level will be maintained at 0.005 (≈0.05/10).

a) Survival Rate:

A major index for the treatment effect of ORD is to determine survival rate. It is recorded twice a day and a survival curve created.

b) Daily Activity or Signs of Sickness

All of the mice are observed once a day for the signs of sickness, such as diarrhea, lack of grooming, ruffled hair, decreased eating and drinking habits, lethargy, etc, and recorded carefully.

c) Body Weight, Stool Formation and Occult Blood

To determine if the ORD could reverse some of the effects from IR-induced GI toxicity, the colon will be removed and pictured for stool formation and feces analyzed for occult blood, when those animals are sacrificed for functional studies as described herein. These studies allows for determining if the mitigation agents are able to maintain the integrity of GI mucosa and their function that are visible to the naked eye.

d) Immunohistochemistry

Inflammatory cell infiltration in the lamina propria is analyzed using H&E stained sections from jejunum or ileum. Care will be taken to determine the distribution frequency of lymphoid follicles.

The optimal dose, starting time and schedule of ORD for acute GI toxicity are determined in a sequence. Mice are treated with different dose formulation of ORD after IR exposure. The optimal dose is determined in logistic regression models by determining survival over 7 days (yes versus no) as the response variable and dose level as the explanatory variable. Due to the uncertainty of the dose-response curve, several plausible dose-response models are proposed. After the model of dose-response is determined, the minimum effective dose (MED) is calculated. Starting Time and optimal duration of the therapy are answered by equivalence tests using the estimated mean responses and variance in the ANOVA model.

Example 17

Determination of Functional Improvement in GI Function

In this Example, electrophysiology experiments are performed to determine how ORD helps restore IR-injured gut mucosa to absorb electrolytes and nutrients. Functional changes are correlated to plasma surrogate marker(s), cytology, and physical observations such as daily activity, body weight, and stool formation. Fecal occult blood, cytology such as crypt assay, H&E staining, BrdU staining, immunohistochemistry and Western blot analysis. These studies allow for the determination of the protective effects of ORD on GI function at molecular, cellular and functional level.

Methods

C57BL/6 mice (8 weeks old, male) from NCI are used. Functional studies, physical observations, cytology, immunohistochemistry, Western analysis are performed and plasma surrogate markers are used as specific indices for IR-induced GI toxicity. Mice were randomly divided into groups and the abdomen irradiated with a Shepherd Mark-I using a Cs source delivering IR at 1.84 Gy/min dose rate. Mice are irradiated with 1, 3, 5, 7 or 9 Gy and then are administered ORD. Mice are treated with ORD. Mice are sacrificed on day 6 and tissues are used for functional, histopathology, Western blot and immunohistochemistry.

A) Correlation of Effects of ORD with Functional Improvement in Electrolyte and Nutrient Absorption A set of indices are used to evaluate the treatment effect: 1) the mice are weighted daily and closely observed for any sickness signs; 2) blood samples and physical parameters are analyzed when the animals are sacrificed for functional studies (electrolyte and nutrient absorption), crypt assay, immunohistochemistry and western blot analysis. Blood samples are used for measuring plasma endotoxin (an index for gut barrier dysfunction), cytokines, gut peptides (insulin, Glucagon, secretin, cholecystokinin, citrullin, somatostatin, peptide YY, Ghrelin, NPY and GLP2), citrulline, glucose and insulin.

Determination of Transepithelial Flux of $Na^+$ and $Cl^-$ in Ussing Chamber Studies To investigate functional improvement of ORD, jejunum and ileum sheets (subjected to separate evaluation) obtained from mice are mounted in Ussing chamber and experiments are performed as described in Example 15. $Na^+$ and $Cl^-$ absorption are compared between non-IR, IR and ORD treated mice groups.

Determination of $HCO_3^-$ Secretion using pH Stat Techniques

Experiments are performed as described in Example 15. Restoration of $HCO_3^-$ secretion with ORD treatment suggests functional improvement. $HCO_3^-$ secretion is compared between non-IR, IR and ORD treated mice groups.

Determination of Nutrient Absorption in Ussing Chamber and Vesicle Studies

As described in Example 15, glucose, electrogenic a.a and electroneutral a.a absorption is determined. Results from these studies are compared between non-IR, IR and ORD treated mice groups.

Determination of Changes in Paracellular Permeability with Mitigation Following IR A decrease in paracellular permeability with ORD treatment suggests improvement in epithelial integrity. These changes will indicate concomitant improvement in plasma endotoxin level.

Correlate Effects of ORD with Crypt Assay, H&E Staining, BrdU, Stool Formation, Occult Blood, Body Weight, Immunohistochemistry and Western Analysis The studies will be similar to that described earlier in Example 15 and the results will be compared between non-IR, IR and ORD treated mice groups.

Histopathological Analysis to Determine Anatomical Improvement

Specimens will be processed for H&E staining and pathological analysis, including the crypt assay, BrdU staining as described in Example 15. Briefly, the tissues will be fixed in formalin, processed in paraffin blocks and stained with H & E.

Immunohistochemistry to Detect Changes in the Expression Pattern of Transport Proteins, Crypt and Villous Cell Marker The tissues harvested will be used for immuno-staining using various antibodies that are specific to various transporters (NHE3, NBCe1-A/B, SGLT, $B^{0/+}$, $b^{0/+}$, $X^-_{AG}$) and cell surface markers (Lgr5, EphB2 and EphB3). The method will be similar to that described in Example 15.

These studies will help determine the extent of villous and crypt cell formation following treatment with ORD.

Western Blot Analysis to Study Molecular Alterations of Transport Processes Involved in Electrolyte and Nutrient Transport The method will be similar to that described in Example 15. CFTR activity (correlating with electrogenic $Cl^-$ secretion), NHE3 activity (correlates with $Na^+$ absorption), NBCe1-A/B activity in the villous (correlates with $HCO_3^-$ secretion), SGLT-1, $B^{0/+}$, $b^{0/+}$ or $X^-_{AG}$ will be examined.

Correlate Effects of ORD using Plasma Analysis of Surrogate Marker(s)

Preliminary studies have shown changes in gut peptides following IR in mice. Changes in surrogate marker levels toward basal levels are examined and the results will indicate systemic improvement with ORD treatment.

Statistical Analysis

The mean and standard deviation of the raw data are calculated and graphical techniques such as bar chart will be applied. The main approach to comparing these two groups (treatment vs. vehicle) utilizes mixed effect models (linear or non-linear) based on longitudinal data.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENCES

1. Wolfe, B. M., et al. Experience with home parenteral nutrition. Am J Surg 146, 7-14 (1983).
2. Beer, W. H., Fan, A. & Halsted, C. H. Clinical and nutritional implications of radiation enteritis. Am J Clin Nutr 41, 85-91 (1985).
3. Donaldson, S. S. Nutritional consequences of radiotherapy. Cancer Res 37, 2407-2413 (1977).
4. Theis, V. S., Sripadam, R., Ramani, V. & Lal, S. Chronic Radiation Enteritis. Clin Oncol (R Coll Radiol) (2009).
5. Gunnlaugsson, A., et al. Dose-volume relationships between enteritis and irradiated bowel volumes during 5-fluorouracil and oxaliplatin based chemoradiotherapy in locally advanced rectal cancer. Acta Oncol 46, 937-944 (2007).
6. Dickerson, J. W. Nutrition in the cancer patient: a review. J R Soc Med 77, 309-315 (1984).
7. Bounous, G., et al. Dietary protection during radiation therapy. Strahlentherapie 149, 476-483 (1975).
8. Alpers, D. H. Glutamine: do the data support the cause for glutamine supplementation in humans? Gastroenterology 130, S106-116 (2006).
9. Hauer-Jensen, M., Wang, J., Boerma, M., Fu, Q. & Denham, J. W. Radiation damage to the gastrointestinal tract: mechanisms, diagnosis, and management. Curr Opin Support Palliat Care 1, 23-29 (2007).
10. Tankel, H. I., Clark, D. H. & Lee, F. D. Radiation enteritis with malabsorption. Gut 6, 560-569 (1965).
11. Yeoh, E. K., et al. Gastrointestinal function in chronic radiation enteritis-effects of loperamide-N-oxide. Gut 34, 476-482 (1993).
12. Gavazzi, C., Bhoori, S., Lovullo, S., Cozzi, G. & Mariani, L. Role of home parenteral nutrition in chronic radiation enteritis. Am J Gastroenterol 101, 374-379 (2006).
13. Traber, P. G., Yu, L., Wu, G. D. & Judge, T. A. Sucrase-isomaltase gene expression along crypt-villous axis of human small intestine is regulated at level of mRNA abundance. Am J Physiol 262, G123-130 (1992).
14. Minhas, B. S. & Field, M. Localization of bicarbonate transport along the crypt-villous axis in rabbit ileum. Gastroenterology 106, 1562-1567. (1994).
15. Welsh, M. J., Smith, P. L., Fromm, M. & Frizzell, R. A. Crypts are the site of intestinal fluid and electrolyte secretion. Science 218, 1219-1221. (1982).
16. Rijke, R. P., van der Meer-Fieggen, W. & Galjaard, H. Effect of villous length on cell proliferation and migration in small intestinal epithelium. Cell Tissue Kinet 7, 577-586 (1974).
17. Wright, N. A. & Irwin, M. The kinetics of villous cell populations in the mouse small intestine. I. Normal villi: the steady state requirement. Cell Tissue Kinet 15, 595-609 (1982).
18. Roberts, S. A., Hendry, J. H. & Potten, C. S. Intestinal crypt clonogens: a new interpretation of radiation survival curve shape and clonogenic cell number. Cell Prolif 36, 215-231 (2003).
19. Roberts, S. A. & Potten, C. S. Clonogen content of intestinal crypts: its deduction using a microcolony assay on whole mount preparations and its dependence on radiation dose. Int J Radiat Biol 65, 477-481 (1994).
20. Potten, C. S., Owen, G. & Roberts, S. A. The temporal and spatial changes in cell proliferation within the irradiated crypts of the murine small intestine. Int J Radiat Biol 57, 185-199 (1990).
21. MacNaughton, W. K. Review article: new insights into the pathogenesis of radiation-induced intestinal dysfunction. Aliment Pharmacol Ther 14, 523-528 (2000).
22. Rodier, J. F. Radiation enteropathy-incidence, aetiology, risk factors, pathology and symptoms. Tumori 81, 122-125 (1995).
23. Pia de la Maza, M., et al. Acute nutritional and intestinal changes after pelvic radiation. J Am Coll Nutr 20, 637-642 (2001).
24. Leiper, K. & Morris, A. I. Treatment of radiation proctitis. Clin Oncol (R Coll Radiol) 19, 724-729 (2007).

25. Denton, A. S., Andreyev, H. J., Forbes, A. & Maher, E. J. Systematic review for non-surgical interventions for the management of late radiation proctitis. Br J Cancer 87, 134-143 (2002).
26. Andreyev, J. Gastrointestinal complications of pelvic radiotherapy: are they of any importance? Gut 54, 1051-1054 (2005).
27. DeCosse, J. J., et al. The natural history and management of radiation induced injury of the gastrointestinal tract. Ann Surg 170, 369-384 (1969).
28. Libotte, F., et al. Survival of patients with radiation enteritis of the small and the large intestine. Acta Chir Belg 95, 190-194 (1995).
29. Galland, R. B. & Spencer, J. The natural history of clinically established radiation enteritis. Lancet 1, 1257-1258 (1985).
30. Classen, J., et al. Radiation-induced gastrointestinal toxicity. Pathophysiology, approaches to treatment and prophylaxis. Strahlenther Onkol 174 Suppl 3, 82-84 (1998).
31. Donaldson, S. S., et al. Radiation enteritis in children. A retrospective review, clinicopathologic correlation, and dietary management. Cancer 35, 1167-1178 (1975).
32. Voitk, A. J., Brown, R. A., McArdle, A. H., Hinchey, E. J. & Gurd, F. N. Clinical uses of an elemental diet: preliminary studies. Can Med Assoc J 107, 123-129 (1972).
33. Klimberg, V. S., et al. Prophylactic glutamine protects the intestinal mucosa from radiation injury. Cancer 66, 62-68 (1990).
34. Klimberg, V. S., et al. Oral glutamine accelerates healing of the small intestine and improves outcome after whole abdominal radiation. Arch Surg 125, 1040-1045 (1990).
35. Jensen, J. C., et al. Prevention of chronic radiation enteropathy by dietary glutamine. Ann Surg Onkol 1, 157-163 (1994).
36. Kozelsky, T. F., et al. Phase III double-blind study of glutamine versus placebo for the prevention of acute diarrhea in patients receiving pelvic radiation therapy. J Clin Oncol 21, 1669-1674 (2003).
37. Silvain, C., et al. Long-term outcome of severe radiation enteritis treated by total parenteral nutrition. Dig Dis Sci 37, 1065-1071 (1992).
38. Ekelund, M., Kristensson, E. & Ekblad, E. Total parenteral nutrition causes circumferential intestinal atrophy, remodeling of the intestinal wall, and redistribution of eosinophils in the rat gastrointestinal tract. Dig Dis Sci 52, 1833-1839 (2007).
39. Jackson, W. D. & Grand, R. J. The human intestinal response to enteral nutrients: a review. J Am Coll Nutr 10, 500-509 (1991).
40. Burrin, D. G., et al. Minimal enteral nutrient requirements for intestinal growth in neonatal piglets: how much is enough? Am J Clin Nutr 71, 1603-1610 (2000).
41. Drucker, D. J., et al. Biologic properties and therapeutic potential of glucagon-like peptide-2. JPEN J Parenter Enteral Nutr 23, S98-100 (1999).
42. Niinikoski, H., et al. Onset of small intestinal atrophy is associated with reduced intestinal blood flow in TPN-fed neonatal piglets. J Nutr 134, 1467-1474 (2004).
43. Matheson, P. J., Wilson, M. A. & Garrison, R. N. Regulation of intestinal blood flow. J Surg Res 93, 182-196 (2000).
44. Nowicki, P. T., Stonestreet, B. S., Hansen, N. B., Yao, A. C. & Oh, W. Gastrointestinal blood flow and oxygen consumption in awake newborn piglets: effect of feeding. Am J Physiol 245, G697-702 (1983).
45. van Goudoever, J.B., et al. Secretion of trophic gut peptides is not different in bolus- and continuously fed piglets. J Nutr 131, 729-732 (2001).
46. Knickelbein, R., Aronson, P. S., Schron, C. M., Seifter, J. & Dobbins, J. W. Sodium and chloride transport across rabbit ileal brush border. II. Evidence for Cl—HCO3 exchange and mechanism of coupling. The American Journal of Physiology 249, G236-245 (1985).
47. Field, M., Fromm, D. & McColl, I. Ion transport in rabbit ileal mucosa. I. Na and Cl fluxes and short-circuit current. Am J Physiol 220, 1388-1396 (1971).
48. Sellin, J. . & DeSoignie, R. Rabbit proximal colon: a distinct transport epithelium. Am J Physiol 246, G603-610 (1984).
49. Turnberg, L. A, Bieberdorf, F. A, Morawski, S. G & Fordtran, J. S. Interrelationships of chloride, bicarbonate, sodium, and hydrogen transport in the human ileum. J Clin Invest 49, 557-567 (1970).
50. Bach, S. P., Renehan, A. G. & Potten, C. S. Stem cells: the intestinal stem cell as a paradigm. Carcinogenesis 21, 469-476 (2000).
51. Kaur, P. & Potten, C. S. Cell migration velocities in the crypts of the small intestine after cytotoxic insult are not dependent on mitotic activity. Cell Tissue Kinet 19, 601-610 (1986).
52. Qiu, J. M., Roberts, S. A. & Potten, C. S. Cell migration in the small and large bowel shows a strong circadian rhythm. Epithelial Cell Biol 3, 137-148 (1994).
53. Al-Dewachi, H. S., Wright, N. A., Appleton, D. R. & Watson, A.J. The effect of a single injection of hydroxyurea on cell population kinetics in the small bowel mucosa of the rat. Cell Tissue Kinet 10, 203-213 (1977).
54. Hendry, J. H., et al. The response of murine intestinal crypts to short-range promethium-147 beta irradiation: deductions concerning clonogenic cell numbers and positions. Radiat Res 118, 364-374 (1989).
55. Okine, E. K., Glimm, D. R., Thompson, J. R. & Kennelly, J. J. Influence of stage of lactation on glucose and glutamine metabolism in isolated enterocytes from dairy cattle. Metabolism 44, 325-331 (1995).
56. Alpers, D. H. Is glutamine a unique fuel for small intestinal cells? Curr Opin Gastroenterol 16, 155 (2000).
57. Wu, G. Intestinal mucosal amino acid catabolism. J Nutr 128, 1249-1252 (1998).
58. Tome, D. & Bos, C. Lysine requirement through the human life cycle. J Nutr 137, 1642S-1645S (2007).
59. Vayro, S., Lo, B. & Silverman, M. Functional studies of the rabbit intestinal Na+/glucose carrier (SGLT1) expressed in COS-7 cells: evaluation of the mutant A166C indicates this region is important for Na+-activation of the carrier. Biochem J 332 (Pt 1), 119-125 (1998).
60. Loo, D. D., Zeuthen, T., Chandy, G. & Wright, E. M. Cotransport of water by the Na+/glucose cotransporter. Proc Natl Acad Sci USA 93, 13367-13370 (1996).
61. Benson, A. B., 3rd, et al. Recommended guidelines for the treatment of cancer treatment-induced diarrhea. J Clin Oncol 22, 2918-2926 (2004).
62. Mehta, D. I., Horvath, K., Chanasongcram, S., Hill, I. D. & Panigrahi, P. Epidermal growth factor up-regulates sodium-glucose cotransport in enterocyte models in the presence of cholera toxin. JPEN J Parenter Enteral Nutr 21, 185-191 (1997).
63. Thomson, A. B., Cheeseman, C. I. & Walker, K. Late effects of abdominal radiation on intestinal uptake of nutrients. Radiat Res 107, 344-353 (1986).
64. Porteous, J. W. Intestinal metabolism. Environ Health Perspect 33, 25-35 (1979).
65. Balda, M. S. & Matter, K. The tight junction protein ZO-1 and an interacting transcription factor regulate ErbB-2 expression. Embo J 19, 2024-2033 (2000).

66. Stefani, E. & Cereijido, M. Electrical properties of cultured epithelioid cells (MDCK). J Membr Biol 73, 177-184 (1983).
67. Gonzalez-Mariscal, L., Chavez de Ramirez, B., Lazaro, A. & Cereijido, M. Establishment of tight junctions between cells from different animal species and different sealing capacities. J Membr Biol 107, 43-56 (1989).
68. Souba, W. W., Scott, T. E. & Wilmore, D. W. Intestinal consumption of intravenously administered fuels. JPEN J Parenter Enteral Nutr 9, 18-22 (1985).
69. Cardona Pera, D. [Administration of glutamine and its dipeptides in parenteral nutrition. Which patients are candidates?]. Nutr Hosp 13, 8-20 (1998).
70. Joiner, W.J., et al. Active K+secretion through multiple KCa-type channels and regulation by IKCa channels in rat proximal colon. Am J Physiol Gastrointest Liver Physiol 285, G185-196 (2003).
71. Vidyasagar, S. & Ramakrishna, B.S. Effects of butyrate on active sodium and chloride transport in rat and rabbit distal colon. J Physiol (Lond) 539, 163-173 (2002).
72. Vidyasagar, S., Barmeyer, C., Geibel, J., Binder, H. J. & Rajendran, V. M. Role of Short-Chain Fatty Acids in Colonic HCO3 Secretion. Am J Physiol Gastrointest Liver Physiol 288, G1217-1226 (2005).
73. Vidyasagar, S., Rajendran, V. M. & Binder, H. J. Three distinct mechanisms of HCO3-secretion in rat distal colon. Am J Physiol Cell Physiol 287, C612-621 (2004).
74. Zhang, H., Ameen, N., Melvin, J. E. & Vidyasagar, S. Acute inflammation alters bicarbonate transport in mouse ileum. J Physiol 581, 1221-1233 (2007).
75. Hopfer, U., Nelson, K., Perrotto, J. & Isselbacher, K. J. Glucose transport in isolated brush border membrane from rat small intestine. J Biol Chem 248, 25-32 (1973).
76. Bradford, M. M. A rapid and sensitive method for the quantitation of microgram quantities of protein utilizing the principle of protein-dye binding. Anal Biochem 72, 248-254 (1976).
77. Heath, J. P. Epithelial cell migration in the intestine. Cell Biol Int 20, 139-146 (1996).
78. Reagan-Shaw, S., Nihal, M. & Ahmad, N. Dose translation from animal to human studies revisited. FASEB J 22, 659-661 (2008).

We claim:

1. A formulation for enteral administration comprising:
    as free amino acids, a therapeutically effective amount of serine and valine; and
    a therapeutically effective amount of at least one additional free amino acid of threonine, lysine, glycine, aspartic acid, isoleucine, tryptophan, or tyrosine, or any combination thereof;
    wherein the therapeutically effective amount of the serine and valine and the therapeutically effective amount of the at least one additional free amino acid mitigates symptoms of diarrhea;
    wherein the formulation does not comprise glucose, or when the formulation does comprise glucose, the glucose is present in a concentration equal to or less than 10 mM;
    wherein the formulation does not comprise:
        free amino acid glutamine;
        a glutamine-containing dipeptide;
        or any combination thereof;
    wherein the formulation does not comprise:
        free amino acid methionine;
        a methionine-containing dipeptide;
        or any combination thereof;
    wherein the formulation does not comprise riboflavin; and
    wherein a therapeutically effective amount of the formulation mitigates symptoms of diarrhea.

2. The formulation of claim 1, wherein serine is present at a concentration of about 420 to 3784 mg/l and valine is present at a concentration of about 469 to 4217 mg/l.

3. The formulation of claim 1 or 2, wherein threonine if present is at a concentration of about 476 to 4288 mg/l; lysine if present is at a concentration of about 730 to 6575 mg/l; glycine if present is at a concentration of about 300 to 2703 mg/l; aspartic acid if present is at a concentration of about 532 to 4792 mg/l; isoleucine if present is at a concentration of about 525 to 4722 mg/l;
    tryptophan if present is at a concentration of about 817 to 7352 mg/l; and tyrosine if present is at a concentration of about 725 to 6523 mg/l.

4. The formulation of claim 1 or 2, wherein threonine if present is at 19-29 mosm; lysine if present is at 11-21 mosm; glycine if present is at 19-29 mosm; aspartic acid if present is at 3-13 mosm; isoleucine if present is at 19-29 mosm; tryptophan if present is at 5-20 mosm; and tyrosine if present is at 0.5-5 mosm.

5. The formulation of claim 3, wherein the total osmolarity of the composition is from about 240 mosm to 280 mosm.

6. The formulation of claim 1, wherein the formulation does not comprise fructose.

7. The formulation of claim 1, wherein the formulation further comprises water.

8. The formulation of claim 1, wherein the formulation further comprises electrolytes, vitamins, and/or minerals, wherein the vitamins do not comprise riboflavin.

9. The formulation of claim 1, which is sterile.

10. The formulation of claim 1, wherein the glucose concentration is less than 4 mM.

11. The formulation of claim 1, wherein the free amino acids consist essentially of:
    serine;
    valine; and
    at least one of: threonine, lysine, glycine, aspartic acid, isoleucine, tryptophan, tyrosine, or any combination thereof.

12. The formulation of claim 1, wherein the free amino acids consist of:
    serine;
    valine; and
    at least one of: threonine, lysine, glycine, aspartic acid, isoleucine, tryptophan, tyrosine, or any combination thereof.

13. A formulation for enteral administration comprising free amino acids:
    wherein the free amino acids consist essentially of a therapeutically effective amount of free amino acids of serine and valine; and
    a therapeutically effective amount of at least one additional free amino acid of threonine, lysine, glycine, aspartic acid, isoleucine, tryptophan, or tyrosine, or any combination thereof;
    wherein the therapeutically effective amount of the serine and valine and the therapeutically effective amount of the at least one additional free amino acid mitigates symptoms of diarrhea;
    wherein the formulation does not comprise glucose, or when the formulation does comprise glucose, the glucose is present in a concentration equal to or less than 10 mM; and
    wherein a therapeutically effective amount of the formulation mitigates symptoms of diarrhea.

14. A formulation for enteral administration comprising free amino acids:
- wherein the free amino acids consist of a therapeutically effective amount of free amino acids of serine and valine; and
- a therapeutically effective amount of at least one additional free amino acid of threonine, lysine, glycine, aspartic acid, isoleucine, tryptophan, or tyrosine, or any combination thereof;
- wherein the therapeutically effective amount of the serine and valine and the therapeutically effective amount of the at least one additional free amino acid mitigates symptoms of diarrhea;
- wherein the formulation does not comprise glucose, or when the formulation does comprise glucose, the glucose is present in a concentration equal to or less than 10 mM; and
- wherein a therapeutically effective amount of the formulation mitigates symptoms of diarrhea.

15. A formulation for enteral administration consisting of free amino acids:
- wherein the free amino acids consist of a therapeutically effective amount of free amino acids of serine and valine; and
- a therapeutically effective amount of at least one additional free amino acid of threonine, lysine, glycine, aspartic acid, isoleucine, tryptophan, or tyrosine, or any combination thereof;
- wherein the therapeutically effective amount of the serine and valine and the therapeutically effective amount of the at least one additional free amino acid mitigates symptoms of diarrhea;
- wherein the formulation does not comprise glucose, or when the formulation does comprise glucose, the glucose is present in a concentration equal to or less than 10 mM; and
- optionally, therapeutically acceptable carriers, electrolytes, vitamins, buffering agents, and/or minerals, wherein the formulation does not comprise riboflavin;
- wherein a therapeutically effective amount of the formulation mitigates symptoms of diarrhea.

16. A method for treating a subject having villous atrophy, wherein the method comprises administering to the subject, via enteral administration, the formulation of claim 1.

17. The method of claim 16, wherein the subject is a human.

18. The method of claim 16, wherein the subject has at least a 5% reduction in total number of small intestinal epithelial cells in the villous region, when compared to normal.

19. The method of claim 16, wherein the subject has at least a 5% loss in villous height in the small intestine, when compared to normal.

20. The method of claim 16, wherein the formulation comprises lysine, glycine, aspartic acid, and/or isoleucine.

21. The method of claim 16, wherein the villous atrophy is caused by disease, radiation, chemotherapy, proton therapy, abdominal surgery, and/or a cytotoxic agent.

22. The method of claim 21, wherein the formulation is administered for a period of 1 to 14 days after the subject receives radiation, chemotherapy, proton therapy, or a cytotoxic agent.

23. The method of claim 16, wherein the villous atrophy is caused by radiation enteritis.

24. The method of claim 22, wherein the chemotherapy or cytotoxic agents comprises treatment with cisplatin, 5-fluorouracil (5-FU), hydroxyurea, etoposide, arabinoside, 6-mercaptopurine, 6-thioguanine, fludarabine, methothexate, steroids, or a combination thereof.

25. The method of claim 21, wherein the villous atrophy is caused by inflammatory bowel disease (IBD), ulcerative colitis, duodenal ulcers, or Crohn's disease.

* * * * *